United States Patent
De Limon et al.

(10) Patent No.: US 9,149,225 B2
(45) Date of Patent: Oct. 6, 2015

(54) METHODS FOR DETERMINING THE RELATIVE SPATIAL CHANGE IN SUBSURFACE RESISTIVITIES ACROSS FREQUENCIES IN TISSUE

(71) Applicant: Intersection Medical, Inc., Carlsbad, CA (US)

(72) Inventors: Alfonso L. De Limon, Encinitas, CA (US); Scott M. Chetham, Del Mar, CA (US); Paul J. Erlinger, San Clemente, CA (US)

(73) Assignee: Intesection Medical, Inc., Carlsbad, CA (US)

( * ) Notice: Subject to any disclaimer, the term of this patent is extended or adjusted under 35 U.S.C. 154(b) by 0 days.

(21) Appl. No.: 13/715,788

(22) Filed: Dec. 14, 2012

(65) Prior Publication Data
US 2013/0165761 A1 Jun. 27, 2013

Related U.S. Application Data

(60) Provisional application No. 61/570,655, filed on Dec. 14, 2011, provisional application No. 61/696,705, filed on Sep. 4, 2012, provisional application No. 61/719,863, filed on Oct. 29, 2012.

(51) Int. Cl.
*A61B 5/00* (2006.01)
*A61B 5/04* (2006.01)
(Continued)

(52) U.S. Cl.
CPC ............... *A61B 5/4878* (2013.01); *A61B 5/04* (2013.01); *A61B 5/05* (2013.01); *A61B 5/0537* (2013.01);
(Continued)

(58) Field of Classification Search
CPC .. A61B 5/04002; A61B 5/053; A61B 5/0531; A61B 5/0535–5/0537; A61B 5/0809; A61B 5/4875; A61B 5/4878; A61B 5/4881; A61B 5/7282
USPC ........................................................ 600/547
See application file for complete search history.

(56) References Cited

U.S. PATENT DOCUMENTS 3,316,896 A 5/1967 Thomasset
3,851,641 A 12/1974 Toole et al.
(Continued)

FOREIGN PATENT DOCUMENTS

CN 1180513 A 5/1998
CN 1236597 A 12/1999
(Continued)

OTHER PUBLICATIONS

Bella et al., "Relations of left ventrical mass to fat-free and adipose body mass: the strong heart study," Circulation, vol. 98, pp. 2538-2544, Dec. 8, 1998.
Bernstein; "A new stroke volume equation for thoracic electrical bio impedance," Critical Care Medicine; Oct. 1986; vol. 14; pp. 904-909.
Edwards, L.S.; A modified pseudosection for resistivity and IP; Geophysics; vol. 42; No. 5; pp. 1020-1036; Aug. 1977.
(Continued)

*Primary Examiner* — Adam J Eiseman
(74) *Attorney, Agent, or Firm* — Shay Glenn LLP

(57) ABSTRACT

Non-invasive devices and systems to determine tissue wetness/hydration based on relative changes in subsurface resistivities in tissue below an electrode array applied to a human body across different frequencies. For example, these a sensor including arrays of current-injecting and voltage-sensing electrodes may be placed on a subject's back to determine lung wetness. Systems and methods for determining tissue water content, systems and methods for determining lung wetness, sensors for determining relative changes in subsurface resistivities across frequencies and systems and methods to determine which arrays of electrodes in a sensor to use to determine relative changes in subsurface resistivities across frequencies are all described.

19 Claims, 58 Drawing Sheets

(51) Int. Cl.
*A61B 5/05* (2006.01)
*A61B 5/053* (2006.01)
*A61B 5/08* (2006.01)

(52) U.S. Cl.
CPC ............ *A61B 5/0809* (2013.01); *A61B 5/4875* (2013.01); *A61B 5/6801* (2013.01); *A61B 5/6813* (2013.01); *A61B 5/6823* (2013.01); *A61B 5/6832* (2013.01); *A61B 5/6833* (2013.01); *A61B 5/7225* (2013.01); *A61B 5/7282* (2013.01); *A61B 5/08* (2013.01); *A61B 5/7203* (2013.01); *A61B 5/7271* (2013.01); *A61B 2562/043* (2013.01); *A61B 2562/164* (2013.01)

(56) References Cited

U.S. PATENT DOCUMENTS

| | | |
|---|---|---|
| 3,866,600 A | 2/1975 | Rey |
| 4,008,712 A | 2/1977 | Nyboer |
| 4,082,087 A | 4/1978 | Howson |
| RE30,101 E | 9/1979 | Kubicek et al. |
| 4,450,527 A | 5/1984 | Sramek |
| 4,486,835 A | 12/1984 | Bai et al. |
| 4,695,955 A | 9/1987 | Faisandier |
| 4,890,630 A | 1/1990 | Kroll et al. |
| 4,905,705 A | 3/1990 | Kizakevich et al. |
| 4,924,875 A | 5/1990 | Chamoun |
| 5,020,541 A | 6/1991 | Marriott |
| 5,063,937 A | 11/1991 | Ezenwa et al. |
| 5,086,781 A | 2/1992 | Bookspan |
| 5,101,828 A | 4/1992 | Welkowitz et al. |
| 5,184,624 A | 2/1993 | Brown et al. |
| 5,233,982 A | 8/1993 | Kohl |
| 5,272,624 A | 12/1993 | Gisser et al. |
| 5,280,429 A | 1/1994 | Withers |
| 5,284,142 A | 2/1994 | Goble et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,421,345 A | 6/1995 | Lekholm et al. |
| 5,423,326 A | 6/1995 | Wang et al. |
| 5,427,113 A | 6/1995 | Hiroshi et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek et al. |
| 5,505,209 A | 4/1996 | Reining |
| 5,526,808 A | 6/1996 | Kaminsky |
| 5,529,072 A | 6/1996 | Sramek |
| 5,544,662 A | 8/1996 | Saulnier et al. |
| 5,575,929 A | 11/1996 | Yu et al. |
| 5,588,429 A | 12/1996 | Isaacson et al. |
| 5,611,351 A | 3/1997 | Sato et al. |
| 5,615,689 A | 4/1997 | Kotler |
| 5,626,146 A | 5/1997 | Barber et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,807,272 A | 9/1998 | Kun et al. |
| 5,876,353 A | 3/1999 | Riff |
| 5,906,614 A | 5/1999 | Stern et al. |
| 5,919,142 A | 7/1999 | Boone et al. |
| 5,947,910 A | 9/1999 | Zimmet |
| 5,957,861 A | 9/1999 | Combs et al. |
| 5,964,703 A | 10/1999 | Goodman et al. |
| 6,018,677 A | 1/2000 | Vidrine et al. |
| 6,125,297 A | 9/2000 | Siconolfi |
| 6,129,666 A | 10/2000 | Deluca et al. |
| 6,142,949 A | 11/2000 | Ubby |
| 6,151,523 A | 11/2000 | Rosell Ferrer et al. |
| 6,167,300 A | 12/2000 | Cherepenin et al. |
| 6,208,890 B1 | 3/2001 | Sarrazin et al. |
| 6,236,886 B1 | 5/2001 | Cherepenin et al. |
| 6,253,100 B1 | 6/2001 | Zhdanov |
| 6,280,396 B1 | 8/2001 | Clark |
| 6,308,097 B1 | 10/2001 | Pearlman |
| 6,339,722 B1 | 1/2002 | Heethaar et al. |
| 6,376,023 B1 | 4/2002 | Mori |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda et al. |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,602,201 B1 | 8/2003 | Hepp et al. |
| 6,615,077 B1 | 9/2003 | Zhu et al. |
| 6,625,487 B2 | 9/2003 | Herleikson |
| 6,631,292 B1 | 10/2003 | Liedtke |
| 6,636,754 B1 | 10/2003 | Baura et al. |
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,724,200 B2 | 4/2004 | Fukuda |
| 6,725,089 B2 | 4/2004 | Komatsu et al. |
| 6,760,617 B2 | 7/2004 | Ward et al. |
| 6,763,263 B2 | 7/2004 | Gregory et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 7,065,399 B2 | 6/2006 | Nakada |
| 7,079,889 B2 | 7/2006 | Nakada |
| 7,096,061 B2 | 8/2006 | Arad |
| 7,122,012 B2 | 10/2006 | Bouton et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,233,823 B2 | 6/2007 | Simond et al. |
| 7,251,524 B1 | 7/2007 | Hepp et al. |
| 7,288,943 B2 | 10/2007 | Matthiessen et al. |
| 7,313,435 B2 | 12/2007 | Nakada et al. |
| 7,336,992 B2 | 2/2008 | Shiokawa |
| 7,440,796 B2 | 10/2008 | Woo et al. |
| 7,496,450 B2 | 2/2009 | Ortiz Aleman et al. |
| 7,603,158 B2 | 10/2009 | Nachman et al. |
| 7,603,171 B2 | 10/2009 | Eror et al. |
| 7,628,761 B2 | 12/2009 | Gozani et al. |
| 7,638,341 B2 | 12/2009 | Rubinsky et al. |
| 7,660,617 B2 | 2/2010 | Davis |
| 7,711,418 B2 | 5/2010 | Garber et al. |
| 7,729,756 B2 | 6/2010 | Mertelmeier et al. |
| 7,917,202 B2 | 3/2011 | Chamney et al. |
| 7,983,853 B2 | 7/2011 | Wang et al. |
| 8,055,335 B2 | 11/2011 | Stylos |
| 8,068,906 B2 | 11/2011 | Chetham |
| 8,172,762 B2 | 5/2012 | Robertson |
| 8,285,356 B2 | 10/2012 | Bly et al. |
| 2001/0051774 A1 | 12/2001 | Littrup et al. |
| 2002/0022773 A1 | 2/2002 | Drinan et al. |

(56) References Cited

U.S. PATENT DOCUMENTS

| | | |
|---|---|---|
| 2002/0106681 A1 | 8/2002 | Wexler et al. |
| 2002/0138019 A1 | 9/2002 | Wexler et al. |
| 2003/0004403 A1 | 1/2003 | Drinan et al. |
| 2003/0009111 A1 | 1/2003 | Cory et al. |
| 2003/0023184 A1 | 1/2003 | Pitts-crick et al. |
| 2003/0028221 A1 | 2/2003 | Zhu et al. |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0176808 A1 | 9/2003 | Masuo |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0054298 A1 | 3/2004 | Masuo et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0116819 A1 | 6/2004 | Alt et al. |
| 2004/0158167 A1 | 8/2004 | Smith et al. |
| 2004/0167423 A1 | 8/2004 | Pillon et al. |
| 2004/0181163 A1 | 9/2004 | Wong et al. |
| 2004/0220632 A1 | 11/2004 | Burnes |
| 2004/0234113 A1 | 11/2004 | Miga |
| 2004/0236202 A1 | 11/2004 | Burton |
| 2004/0242989 A1 | 12/2004 | Zhu et al. |
| 2004/0260167 A1 | 12/2004 | Leonhardt et al. |
| 2004/0267333 A1 | 12/2004 | Kronberg |
| 2005/0039763 A1 | 2/2005 | Kraemer et al. |
| 2005/0070778 A1 | 3/2005 | Lackey et al. |
| 2005/0080460 A1 | 4/2005 | Wang et al. |
| 2005/0101875 A1 | 5/2005 | Semler et al. |
| 2005/0107719 A1 | 5/2005 | Arad |
| 2005/0177061 A1 | 8/2005 | Alanen et al. |
| 2005/0177062 A1 | 8/2005 | Skrabal et al. |
| 2005/0192488 A1 | 9/2005 | Bryenton et al. |
| 2005/0201598 A1 | 9/2005 | Harel et al. |
| 2005/0203435 A1 | 9/2005 | Nakada |
| 2005/0215918 A1 | 9/2005 | Frantz et al. |
| 2005/0228309 A1 | 10/2005 | Fisher |
| 2005/0251062 A1 | 11/2005 | Choi |
| 2005/0261743 A1 | 11/2005 | Kroll et al. |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0052678 A1 | 3/2006 | Drinan et al. |
| 2006/0064029 A1 | 3/2006 | Arad |
| 2006/0085049 A1 | 4/2006 | Cory et al. |
| 2006/0122523 A1 | 6/2006 | Bonmassar et al. |
| 2006/0122540 A1 | 6/2006 | Zhu et al. |
| 2006/0135886 A1 | 6/2006 | Lippert et al. |
| 2006/0184060 A1 | 8/2006 | Belacazar et al. |
| 2006/0200033 A1 | 9/2006 | Keren et al. |
| 2006/0224079 A1 | 10/2006 | Washchuk |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2006/0293609 A1 | 12/2006 | Stahmann et al. |
| 2007/0007975 A1 | 1/2007 | Hawkins et al. |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2008/0001608 A1 | 1/2008 | Saulnier et al. |
| 2008/0009757 A1 | 1/2008 | Tsoglin et al. |
| 2008/0027350 A1 | 1/2008 | Webler |
| 2008/0051643 A1 | 2/2008 | Park et al. |
| 2008/0064981 A1 | 3/2008 | Gregory |
| 2008/0139957 A1 | 6/2008 | Hubbard et al. |
| 2008/0200802 A1 | 8/2008 | Bhavaraju et al. |
| 2008/0247502 A1 | 10/2008 | Liao |
| 2008/0252304 A1 | 10/2008 | Woo et al. |
| 2008/0287823 A1 | 11/2008 | Chetham |
| 2008/0319336 A1 | 12/2008 | Ward et al. |
| 2009/0018432 A1 | 1/2009 | He et al. |
| 2009/0043222 A1 | 2/2009 | Chetham |
| 2009/0069708 A1 | 3/2009 | Hatlestad et al. |
| 2009/0076410 A1 | 3/2009 | Libbus |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0143663 A1 | 6/2009 | Chetham |
| 2009/0209872 A1 | 8/2009 | Pop |
| 2009/0216140 A1 | 8/2009 | Skrabal |
| 2009/0216148 A1 | 8/2009 | Freed et al. |
| 2009/0234244 A1 | 9/2009 | Tanaka |
| 2009/0240163 A1 | 9/2009 | Webler |
| 2009/0264727 A1 | 10/2009 | Markowitz et al. |
| 2009/0264745 A1 | 10/2009 | Markowitz et al. |
| 2009/0264776 A1 | 10/2009 | Vardy |
| 2009/0264791 A1 | 10/2009 | Gregory et al. |
| 2009/0275854 A1 | 11/2009 | Zielinski et al. |
| 2009/0275855 A1 | 11/2009 | Zielinski et al. |
| 2009/0326408 A1 | 12/2009 | Moon |
| 2010/0007357 A1 | 1/2010 | Ammari et al. |
| 2010/0049077 A1 | 2/2010 | Sadleir et al. |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0106046 A1 | 4/2010 | Shochat et al. |
| 2010/0152605 A1 | 6/2010 | Ward |
| 2010/0191141 A1 | 7/2010 | Aberg |
| 2010/0228143 A1 | 9/2010 | Teschner et al. |
| 2011/0025348 A1 | 2/2011 | Chetham et al. |
| 2011/0034806 A1 | 2/2011 | Hartov et al. |
| 2011/0046505 A1 | 2/2011 | Cornish et al. |
| 2011/0054343 A1 | 3/2011 | Chetham et al. |
| 2011/0054344 A1 | 3/2011 | Slizynski et al. |
| 2011/0060239 A1 | 3/2011 | Gaw |
| 2011/0060241 A1 | 3/2011 | Martinsen et al. |
| 2011/0082383 A1 | 4/2011 | Cory et al. |
| 2011/0087129 A1 | 4/2011 | Chetham et al. |
| 2011/0208084 A1* | 8/2011 | Seoane Martinez et al. . 600/547 |
| 2011/0230784 A2 | 9/2011 | Slizynski et al. |
| 2011/0245712 A1 | 10/2011 | Patterson et al. |
| 2011/0251513 A1 | 10/2011 | Chetham et al. |
| 2011/0274327 A1 | 11/2011 | Wehnes et al. |
| 2011/0282180 A1 | 11/2011 | Goldkuhl et al. |
| 2012/0071772 A1 | 3/2012 | Chetham |
| 2012/0165884 A1 | 6/2012 | Xi et al. |
| 2012/0238896 A1 | 9/2012 | Gärber et al. |
| 2013/0102873 A1 | 4/2013 | Hamaguchi et al. |
| 2014/0148721 A1 | 5/2014 | Erlinger et al. |

FOREIGN PATENT DOCUMENTS

| | | |
|---|---|---|
| CN | 1329875 A | 1/2002 |
| EP | 0581073 A2 | 2/1994 |
| EP | 0339471 B1 | 3/1997 |
| EP | 0865763 A2 | 9/1998 |
| EP | 1078597 A2 | 2/2001 |
| EP | 1112715 A1 | 7/2001 |
| EP | 1238630 A2 | 9/2002 |
| EP | 1247487 A1 | 10/2002 |
| EP | 1329190 A1 | 7/2003 |
| EP | 1080686 B1 | 3/2004 |
| FR | 2748928 A1 | 11/1997 |
| JP | 06-000168 A | 1/1994 |
| JP | 08-191808 A | 7/1996 |
| JP | 09-051884 A | 2/1997 |
| JP | 09-220209 A | 8/1997 |
| JP | 10-000185 A | 1/1998 |
| JP | 2002502274 | 10/1998 |

(56) References Cited

FOREIGN PATENT DOCUMENTS

| | | |
|---|---|---|
| JP | 2000-107138 A | 4/2000 |
| JP | 2000-139867 A | 5/2000 |
| JP | 2001037735 A | 2/2001 |
| JP | 2001061804 A | 3/2001 |
| JP | 2003-2116805 A | 4/2003 |
| JP | 2005-137683 | 6/2005 |
| NL | 1019789 C2 | 7/2003 |
| RU | 2112416 C1 | 6/1998 |
| RU | 2138193 C1 | 9/1999 |
| WO | WO 91/19454 A1 | 12/1991 |
| WO | WO 93/18821 A1 | 9/1993 |
| WO | WO 94/01040 A1 | 1/1994 |
| WO | WO 94/10922 A1 | 5/1994 |
| WO | WO 96/01586 A1 | 1/1996 |
| WO | WO 96/12439 A1 | 5/1996 |
| WO | WO 97/11638 A2 | 4/1997 |
| WO | WO 98/06328 A1 | 2/1998 |
| WO | WO 98/33553 A1 | 8/1998 |
| WO | WO 98/51211 A1 | 11/1998 |
| WO | WO 99/42034 A2 | 8/1999 |
| WO | WO 99/48422 A1 | 9/1999 |
| WO | WO 00/19886 A1 | 4/2000 |
| WO | WO 00/40955 A1 | 7/2000 |
| WO | WO 00/79255 A1 | 12/2000 |
| WO | WO 01/27605 A1 | 4/2001 |
| WO | WO 01/52733 A1 | 7/2001 |
| WO | WO 02/053028 A2 | 7/2002 |
| WO | WO 2004/021880 A1 | 3/2004 |
| WO | WO 2004/030535 A1 | 4/2004 |
| WO | WO 2004/032738 A1 | 4/2004 |
| WO | WO 2004/047638 A1 | 6/2004 |
| WO | WO 2004/084087 A1 | 9/2004 |
| WO | WO 2004/084723 A1 | 10/2004 |
| WO | WO 2005/018432 A2 | 3/2005 |
| WO | WO 2005/051163 A2 | 6/2005 |
| WO | WO 2005/122888 A1 | 12/2005 |
| WO | WO 2006/045051 A1 | 4/2006 |
| WO | WO 2006/056074 A1 | 6/2006 |
| WO | WO 2007/070997 A1 | 6/2007 |
| WO | WO 2007/128952 A1 | 11/2007 |
| WO | WO 2008/011716 A1 | 1/2008 |
| WO | WO 2009/027812 A2 | 3/2009 |
| WO | WO 2009/068961 A2 | 6/2009 |
| WO | WO 2009/112965 A1 | 9/2009 |
| WO | WO 2010/003162 A1 | 1/2010 |
| WO | WO 2010/029465 A2 | 3/2010 |
| WO | WO 2010/069023 A2 | 6/2010 |
| WO | WO 2010/076719 A1 | 7/2010 |
| WO | WO 2011/018744 A1 | 2/2011 |
| WO | WO 2011/113169 A1 | 9/2011 |
| WO | WO 2011/136867 A1 | 11/2011 |
| WO | WO2012/149471 A2 | 11/2012 |

OTHER PUBLICATIONS

Ellis, K.J. et al., "Human hydrometry: comparison of multifrequency bioelectrical impedance with 2H2O and bromine dilution," Journal of Applied Physiology, vol. 85, No. 3, pp. 1056-1062, Sep. 1998.

Hansen, E.; On the influence of shape and variations in conductivity of the sample on four-point measurements; Applied Scientific Research, Section B; vol. 8; Issue 1; pp. 93-104; Dec. 1960.

Iacobellis et al., "Influence of excess fat on cardiac morphology and function: study in uncomplicated obesity," Obesity Research, vol. 10, No. 8, pp. 767-773, Aug. 8, 2002.

Igel, J.; On the Small-Scale Variability of Electrical Soil Properties and Its Influence on Geophysical Measurements; Ph.D. Thesis, Frankfurt University, Germany, Hannover; total 188 pages; Apr. 2007.

Jones, C.H. et al., "Extracellular fluid volume determined by bioelectric impedance and serum albumin in CAPD Patients," Nephrology Dialysis Transplantation, vol. 13, pp. 393-397, Feb. 1998.

Karason et al., "Impact of blood pressure and insulin on the relationship between body fat and left ventricular structure," European Heart Journal, vol. 24, pp. 1500-1505, May 2003.

Loke et al.; Least?squares deconvolution of apparent resistivity pseudosections; Geophysics; vol. 60, No. 6; pp. 1682-1690; Nov.-Dec. 1995.

McAdams et al.; Tissue impedance: a historical overview; Physiological Measurement, Institute of Physics Publishing, Bristol, GB; 16 (3A); pp. A1-A13; Aug. 1, 1995.

McEwan et al.; Battery powered and wireless Electrical Impedance Tomography Spectroscopy Imaging using Bluetooth; Medicon 2007; IFMBE Proceedings; vol. 16, pp. 798-801; Jun. 26-30, 2007.

Roy, A.; Depth of investigation in direct current methods; Geophysics; vol. 36; pp. 943-959; Oct. 1971.

Thomas, B.J., "Future Technologies," Asia Pacific Journal Clinical Nutrition, vol. 4, No. 1, pp. 157-159, Mar. 1995.

Thomas, et al.; "Bioimpedance spectrometer in the determination of body water compartments: Accuracy and clinical significance;" Appl. Radiation. Isotopes; vol. 49, No. 5/6; pp. 447-455; Jun. 1998.

Woodrow, G. et al., "Effects of icodextrin in automated peritoneal dialysis on blood pressure and bioelectrical impedance analysis," Nephrology Dialysis Transplantation, vol. 15, pp. 862-866, Jun. 2000.

Yoshinaga et al., "Effect of total adipose weight and systemic hypertension on left ventrical mass in children," American Journal of Cardiology, vol. 76, pp. 785-787, Oct. 15, 1995.

Erlinger et al.; U.S. Appl. No. 13/715,722 entitled "Devices for Determining the Relative Spatial Change in Subsurface Resistivities Across Frequencies in Tissue," filed Dec. 14, 2012.

\* cited by examiner

| | | Small Tank h=0.216m of Saline | Small Tank h=0.356m of Saline | Large Tank h=0.216m of Saline | Large Tank h=0.356m of Saline |
|---|---|---|---|---|---|
| Resistivity of the saline tank | $\rho_{saline}$ | 5.45 mΩ | 10.0345 mΩ | 5.4545 mΩ | 9.8745 mΩ |
| Current | $I$ | 6.12E-03 A | 4.25E-03 A | 6.21E-03 A | 4.34E-03 A |
| Hansen boundary model coefficient for rectangular box | $F_\alpha$ | 1.34 | 1.28 | 1.175 | 1.11 |
| Point model geometric factor | $k_{point}$ | 0.488m | 0.488m | 0.488m | 0.488m |
| Summerfeld line charge coefficient | $k_{ellipse}$ | 0.514m | 0.514m | 0.514m | 0.514m |
| Measured Voltage | $\Delta V_{measured}$ | 0.089V | 0.107V | 0.076V | 0.097V |
| $\Delta V_{point} = \dfrac{I \cdot \rho_{saline}}{k_{point}}$ | $\Delta V_{point}$ | 0.068V | 0.087V | 0.069V | 0.088V |
| $\Delta V_{line} = \dfrac{I \cdot \rho_{saline}}{k_{ellipse}}$ | $\Delta V_{line}$ | 0.065V | 0.083V | 0.066V | 0.083V |
| $\Delta V_{complete} = \dfrac{I \cdot F_\alpha \cdot \rho_{saline}}{k_{ellipse}}$ | $\Delta V_{complete}$ | 0.087V | 0.102V | 0.077V | 0.093V |

FIG. 1F

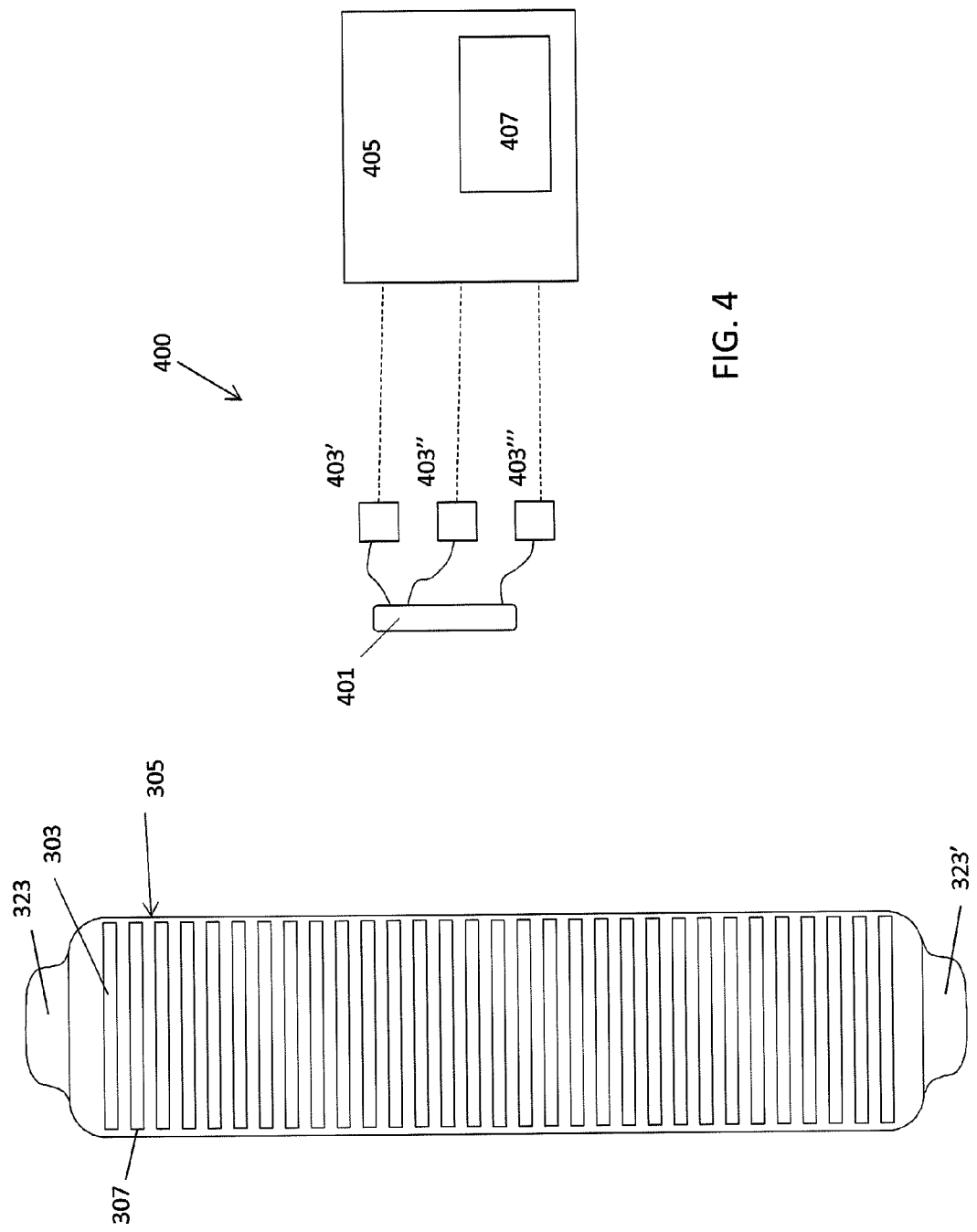

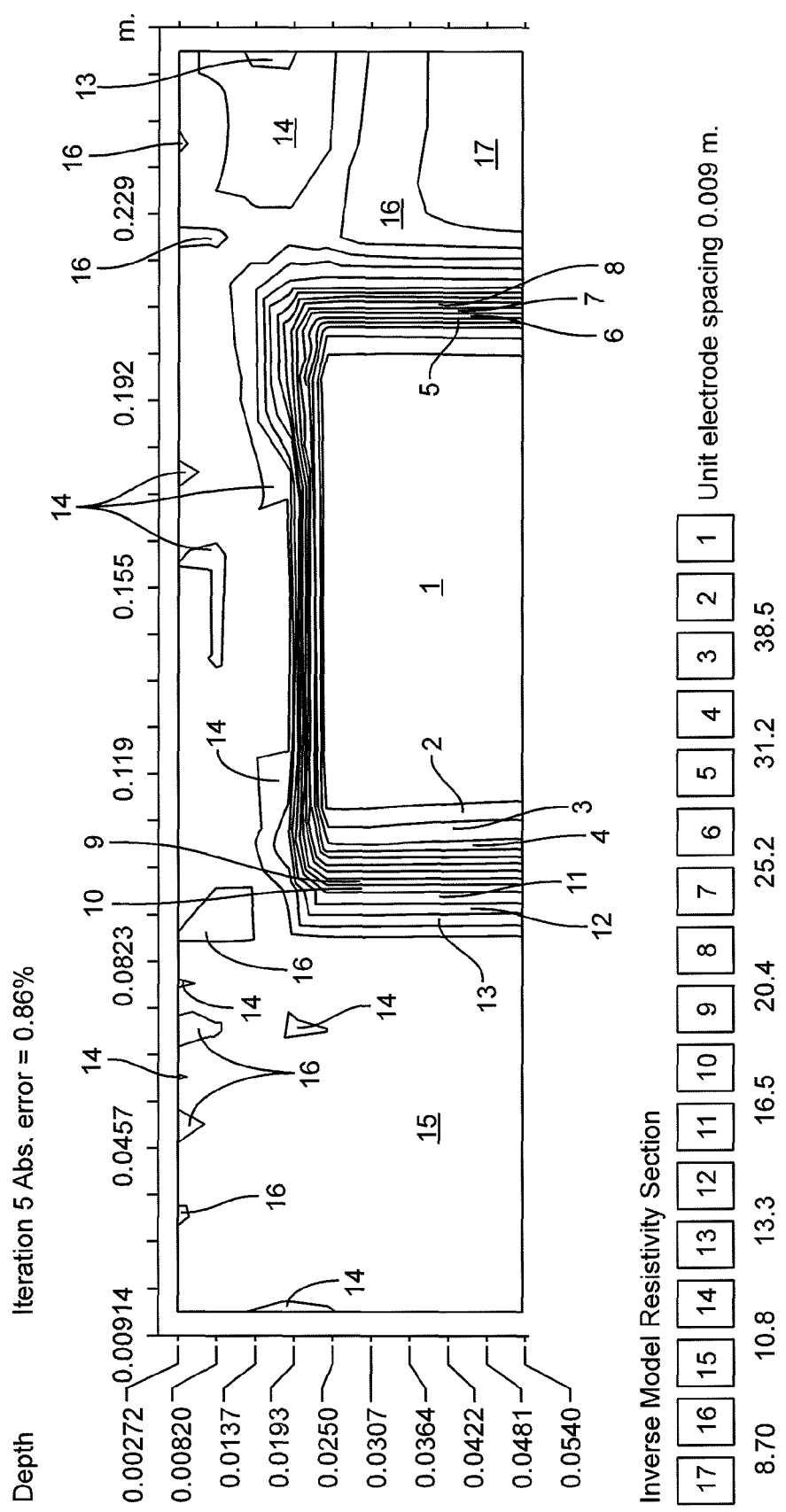

Optimizing each resistivity value
1309

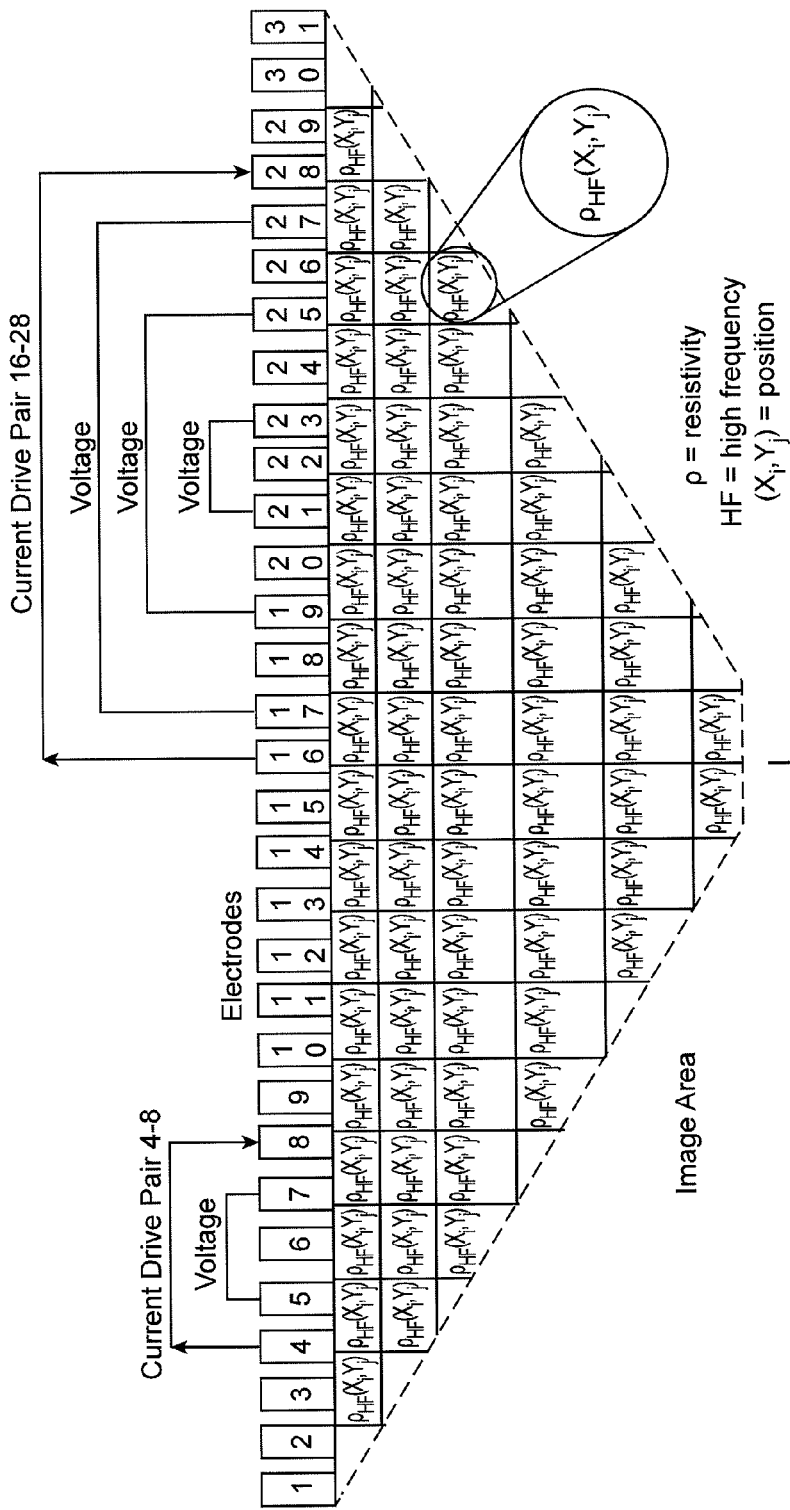
FIG. 14 (Cont. 1)

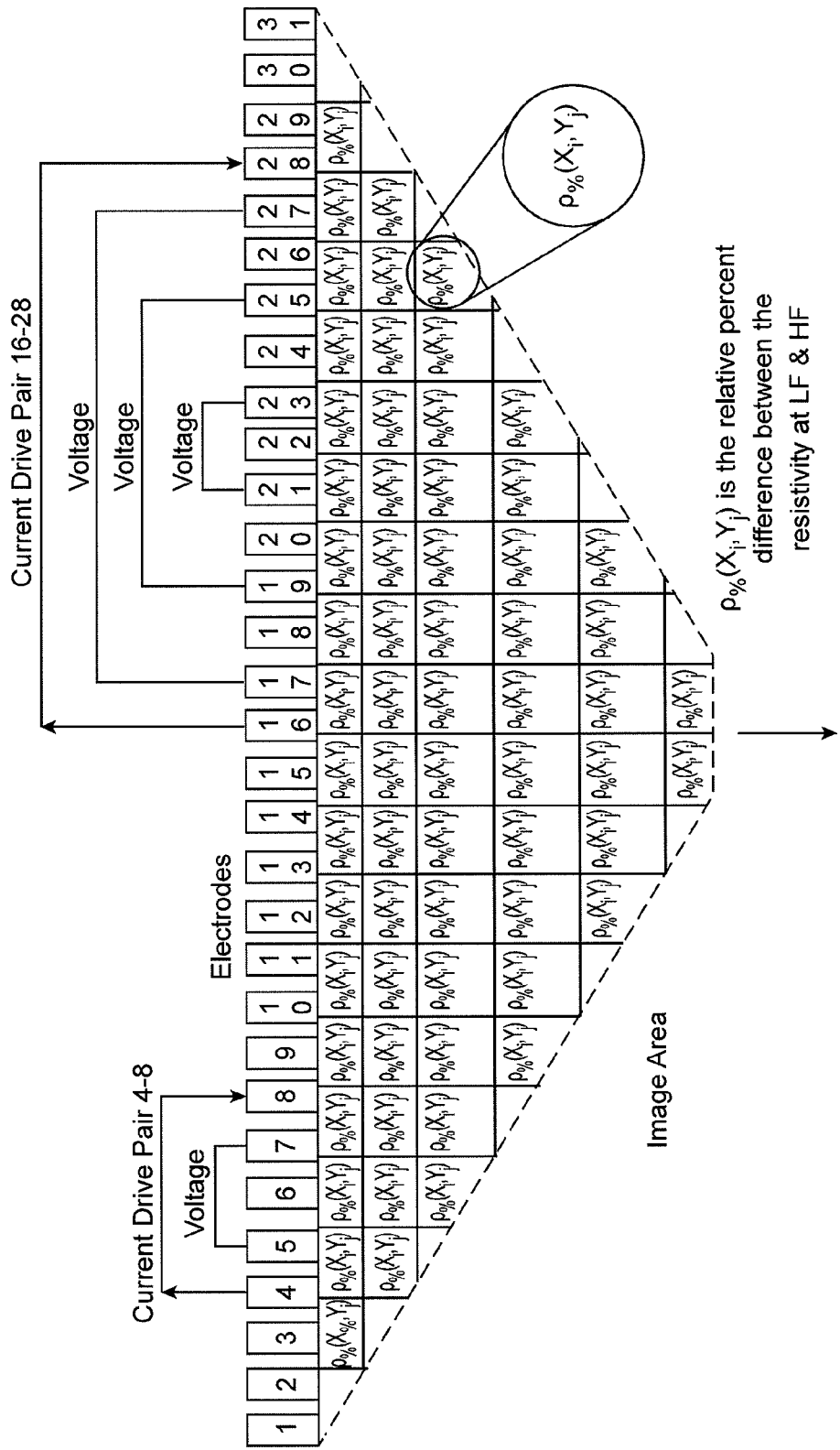
FIG. 14 (Cont. 2)

| # | Array Type, C1, C2, P1, P1 | Depth of Investigation (in) |
|---|---|---|
| 1 | 'RightSidedDipoleDipole' 18 20 1 3 | 1.52 |
| 2 | 'RightSidedDipoleDipole' 20 22 1 3 | 1.70 |
| 3 | 'RightSidedDipoleDipole' 20 22 3 5 | 1.52 |
| 4 | 'RightSidedDipoleDipole' 22 24 1 3 | 1.88 |
| 5 | 'RightSidedDipoleDipole' 22 24 3 5 | 1.70 |
| 6 | 'RightSidedDipoleDipole' 22 24 5 7 | 1.52 |
| 7 | 'RightSidedDipoleDipole' 24 26 1 3 | 2.06 |
| 8 | 'RightSidedDipoleDipole' 24 26 3 5 | 1.88 |
| 9 | 'RightSidedDipoleDipole' 24 26 5 7 | 1.70 |
| 10 | 'RightSidedDipoleDipole' 24 26 7 9 | 1.52 |
| 11 | 'RightSidedDipoleDipole' 26 28 3 5 | 2.06 |
| 12 | 'RightSidedDipoleDipole' 26 28 5 7 | 1.88 |
| 13 | 'RightSidedDipoleDipole' 26 28 7 9 | 1.70 |
| 14 | 'RightSidedDipoleDipole' 26 28 9 11 | 1.52 |
| 15 | 'RightSidedDipoleDipole' 28 30 1 3 | 2.43 |
| 16 | 'RightSidedDipoleDipole' 28 30 5 7 | 2.06 |
| 17 | 'RightSidedDipoleDipole' 28 30 7 9 | 1.88 |
| 18 | 'RightSidedDipoleDipole' 28 30 9 11 | 1.70 |
| 19 | 'RightSidedDipoleDipole' 28 30 11 13 | 1.52 |
| 20 | 'RightSidedDipoleDipole' 18 22 1 5 | 1.48 |
| 21 | 'RightSidedDipoleDipole' 20 24 1 5 | 1.66 |
| 22 | 'RightSidedDipoleDipole' 20 24 3 7 | 1.48 |
| 23 | 'RightSidedDipoleDipole' 22 26 1 5 | 1.85 |
| 24 | 'RightSidedDipoleDipole' 22 26 3 7 | 1.66 |
| 25 | 'RightSidedDipoleDipole' 22 26 5 9 | 1.48 |
| 26 | 'RightSidedDipoleDipole' 24 28 1 5 | 2.03 |
| 27 | 'RightSidedDipoleDipole' 24 28 3 7 | 1.85 |
| 28 | 'RightSidedDipoleDipole' 24 28 5 9 | 1.66 |
| 29 | 'RightSidedDipoleDipole' 24 28 7 11 | 1.48 |
| 30 | 'RightSidedDipoleDipole' 26 30 1 5 | 2.22 |
| 31 | 'RightSidedDipoleDipole' 26 30 3 7 | 2.03 |
| 32 | 'RightSidedDipoleDipole' 26 30 5 9 | 1.85 |
| 33 | 'RightSidedDipoleDipole' 26 30 7 11 | 1.66 |
| 34 | 'RightSidedDipoleDipole' 26 30 9 13 | 1.48 |
| 35 | 'RightSidedDipoleDipole' 20 26 1 7 | 1.60 |
| 36 | 'RightSidedDipoleDipole' 22 28 1 7 | 1.79 |
| 37 | 'RightSidedDipoleDipole' 22 28 3 9 | 1.60 |
| 38 | 'RightSidedDipoleDipole' 24 30 1 7 | 1.98 |
| 39 | 'RightSidedDipoleDipole' 24 30 3 9 | 1.79 |
| 40 | 'RightSidedDipoleDipole' 24 30 5 11 | 1.60 |
| 41 | 'RightSidedDipoleDipole' 22 30 1 9 | 1.71 |

FIG. 22A (Cont. 1)

| #  | Array Type, C1, C2, P1, P1            | Depth of Investigation (in) |
|----|---------------------------------------|-----------------------------|
| 42 | 'LeftSidedDipoleDipole' 2 4 19 21     | 1.52                        |
| 43 | 'LeftSidedDipoleDipole' 2 4 21 23     | 1.70                        |
| 44 | 'LeftSidedDipoleDipole' 2 4 23 25     | 1.88                        |
| 45 | 'LeftSidedDipoleDipole' 2 4 25 27     | 2.06                        |
| 46 | 'LeftSidedDipoleDipole' 2 4 29 31     | 2.43                        |
| 47 | 'LeftSidedDipoleDipole' 4 6 21 23     | 1.52                        |
| 48 | 'LeftSidedDipoleDipole' 4 6 23 25     | 1.70                        |
| 49 | 'LeftSidedDipoleDipole' 4 6 25 27     | 1.88                        |
| 50 | 'LeftSidedDipoleDipole' 4 6 27 29     | 2.06                        |
| 51 | 'LeftSidedDipoleDipole' 6 8 23 25     | 1.52                        |
| 52 | 'LeftSidedDipoleDipole' 6 8 25 27     | 1.70                        |
| 53 | 'LeftSidedDipoleDipole' 6 8 27 29     | 1.88                        |
| 54 | 'LeftSidedDipoleDipole' 6 8 29 31     | 2.06                        |
| 55 | 'LeftSidedDipoleDipole' 8 10 25 27    | 1.52                        |
| 56 | 'LeftSidedDipoleDipole' 8 10 27 29    | 1.70                        |
| 57 | 'LeftSidedDipoleDipole' 8 10 29 31    | 1.88                        |
| 58 | 'LeftSidedDipoleDipole' 10 12 27 29   | 1.52                        |
| 59 | 'LeftSidedDipoleDipole' 10 12 29 31   | 1.70                        |
| 60 | 'LeftSidedDipoleDipole' 12 14 29 31   | 1.52                        |
| 61 | 'LeftSidedDipoleDipole' 2 6 19 23     | 1.48                        |
| 62 | 'LeftSidedDipoleDipole' 2 6 21 25     | 1.66                        |
| 63 | 'LeftSidedDipoleDipole' 2 6 23 27     | 1.85                        |
| 64 | 'LeftSidedDipoleDipole' 2 6 25 29     | 2.03                        |
| 65 | 'LeftSidedDipoleDipole' 2 6 27 31     | 2.22                        |
| 66 | 'LeftSidedDipoleDipole' 4 8 21 25     | 1.48                        |
| 67 | 'LeftSidedDipoleDipole' 4 8 23 27     | 1.66                        |
| 68 | 'LeftSidedDipoleDipole' 4 8 25 29     | 1.85                        |
| 69 | 'LeftSidedDipoleDipole' 4 8 27 31     | 2.03                        |
| 70 | 'LeftSidedDipoleDipole' 6 10 23 27    | 1.48                        |
| 71 | 'LeftSidedDipoleDipole' 6 10 25 29    | 1.66                        |
| 72 | 'LeftSidedDipoleDipole' 6 10 27 31    | 1.85                        |
| 73 | 'LeftSidedDipoleDipole' 8 12 25 29    | 1.48                        |
| 74 | 'LeftSidedDipoleDipole' 8 12 27 31    | 1.66                        |
| 75 | 'LeftSidedDipoleDipole' 10 14 27 31   | 1.48                        |
| 76 | 'LeftSidedDipoleDipole' 2 8 21 27     | 1.60                        |
| 77 | 'LeftSidedDipoleDipole' 2 8 23 29     | 1.79                        |
| 78 | 'LeftSidedDipoleDipole' 2 8 25 31     | 1.98                        |
| 79 | 'LeftSidedDipoleDipole' 4 10 23 29    | 1.60                        |
| 80 | 'LeftSidedDipoleDipole' 4 10 25 31    | 1.79                        |
| 81 | 'LeftSidedDipoleDipole' 6 12 25 31    | 1.60                        |
| 82 | 'LeftSidedDipoleDipole' 2 10 23 31    | 1.71                        |

FIG. 22A (Cont. 2)

| # | Array Type, C1, C2, P1, P1 | Depth of Investigation (in) |
|---|---|---|
| 83 | 'GradientArray' 2 20 9 11 | 1.19 |
| 84 | 'GradientArray' 2 20 11 13 | 1.19 |
| 85 | 'GradientArray' 4 22 11 13 | 1.19 |
| 86 | 'GradientArray' 4 22 13 15 | 1.19 |
| 87 | 'GradientArray' 6 24 13 15 | 1.19 |
| 88 | 'GradientArray' 6 24 15 17 | 1.19 |
| 89 | 'GradientArray' 8 26 15 17 | 1.19 |
| 90 | 'GradientArray' 8 26 17 19 | 1.19 |
| 91 | 'GradientArray' 10 28 17 19 | 1.19 |
| 92 | 'GradientArray' 10 28 19 21 | 1.19 |
| 93 | 'GradientArray' 12 30 19 21 | 1.19 |
| 94 | 'GradientArray' 12 30 21 23 | 1.19 |
| 95 | 'GradientArray' 2 22 9 13 | 1.29 |
| 96 | 'GradientArray' 2 22 11 15 | 1.29 |
| 97 | 'GradientArray' 4 24 11 15 | 1.29 |
| 98 | 'GradientArray' 4 24 13 17 | 1.29 |
| 99 | 'GradientArray' 6 26 13 17 | 1.29 |
| 100 | 'GradientArray' 6 26 15 19 | 1.29 |
| 101 | 'GradientArray' 8 28 15 19 | 1.29 |
| 102 | 'GradientArray' 8 28 17 21 | 1.29 |
| 103 | 'GradientArray' 10 30 17 21 | 1.29 |
| 104 | 'GradientArray' 10 30 19 23 | 1.29 |
| 105 | 'GradientArray' 2 24 9 15 | 1.38 |
| 106 | 'GradientArray' 2 24 11 13 | 1.47 |
| 107 | 'GradientArray' 2 24 11 17 | 1.38 |
| 108 | 'GradientArray' 2 24 13 15 | 1.47 |
| 109 | 'GradientArray' 4 26 11 17 | 1.38 |
| 110 | 'GradientArray' 4 26 13 15 | 1.47 |
| 111 | 'GradientArray' 4 26 13 19 | 1.38 |
| 112 | 'GradientArray' 4 26 15 17 | 1.47 |
| 113 | 'GradientArray' 6 28 13 19 | 1.38 |
| 114 | 'GradientArray' 6 28 15 17 | 1.47 |
| 115 | 'GradientArray' 6 28 15 21 | 1.38 |
| 116 | 'GradientArray' 6 28 17 19 | 1.47 |
| 117 | 'GradientArray' 8 30 15 21 | 1.38 |
| 118 | 'GradientArray' 8 30 17 19 | 1.47 |
| 119 | 'GradientArray' 8 30 17 23 | 1.38 |
| 120 | 'GradientArray' 8 30 19 21 | 1.47 |
| 121 | 'GradientArray' 2 26 9 17 | 1.46 |
| 122 | 'GradientArray' 2 26 11 15 | 1.58 |
| 123 | 'GradientArray' 2 26 11 19 | 1.46 |

FIG. 22B (Cont. 1)

| # | Array Type, C1, C2, P1, P1 | Depth of Investigation (in) |
|---|---|---|
| 124 | 'GradientArray' 2 26 13 17 | 1.58 |
| 125 | 'GradientArray' 4 28 11 19 | 1.46 |
| 126 | 'GradientArray' 4 28 13 17 | 1.58 |
| 127 | 'GradientArray' 4 28 13 21 | 1.46 |
| 128 | 'GradientArray' 4 28 15 19 | 1.58 |
| 129 | 'GradientArray' 6 30 13 21 | 1.46 |
| 130 | 'GradientArray' 6 30 15 19 | 1.58 |
| 131 | 'GradientArray' 6 30 15 23 | 1.46 |
| 132 | 'GradientArray' 6 30 17 21 | 1.58 |
| 133 | 'GradientArray' 2 28 9 19 | 1.52 |
| 134 | 'GradientArray' 2 28 11 15 | 1.65 |
| 135 | 'GradientArray' 2 28 11 17 | 1.68 |
| 136 | 'GradientArray' 2 28 11 21 | 1.52 |
| 137 | 'GradientArray' 2 28 13 15 | 1.76 |
| 138 | 'GradientArray' 2 28 13 19 | 1.68 |
| 139 | 'GradientArray' 2 28 15 17 | 1.76 |
| 140 | 'GradientArray' 2 28 15 19 | 1.65 |
| 141 | 'GradientArray' 4 30 11 21 | 1.52 |
| 142 | 'GradientArray' 4 30 13 17 | 1.65 |
| 143 | 'GradientArray' 4 30 13 19 | 1.68 |
| 144 | 'GradientArray' 4 30 13 23 | 1.52 |
| 145 | 'GradientArray' 4 30 15 17 | 1.76 |
| 146 | 'GradientArray' 4 30 15 21 | 1.68 |
| 147 | 'GradientArray' 4 30 17 19 | 1.76 |
| 148 | 'GradientArray' 4 30 17 21 | 1.65 |
| 149 | 'GradientArray' 2 30 9 21 | 1.58 |
| 150 | 'GradientArray' 2 30 11 17 | 1.75 |
| 151 | 'GradientArray' 2 30 11 19 | 1.76 |
| 152 | 'GradientArray' 2 30 11 23 | 1.58 |
| 153 | 'GradientArray' 2 30 13 15 | 1.82 |
| 154 | 'GradientArray' 2 30 13 17 | 1.87 |
| 155 | 'GradientArray' 2 30 13 21 | 1.76 |
| 156 | 'GradientArray' 2 30 15 19 | 1.87 |
| 157 | 'GradientArray' 2 30 15 21 | 1.75 |
| 158 | 'GradientArray' 2 30 17 19 | 1.82 |
| 159 | 'RightSidedGeneralDipoleDipole' 18 20 1 5 | 1.41 |
| 160 | 'RightSidedGeneralDipoleDipole' 20 22 1 5 | 1.59 |
| 161 | 'RightSidedGeneralDipoleDipole' 20 22 1 7 | 1.47 |
| 162 | 'RightSidedGeneralDipoleDipole' 20 22 3 7 | 1.41 |
| 163 | 'RightSidedGeneralDipoleDipole' 22 24 1 5 | 1.77 |
| 164 | 'RightSidedGeneralDipoleDipole' 22 24 1 7 | 1.65 |

FIG. 22B (Cont. 2)

| # | Array Type, C1, C2, P1, P1 | Depth of Investigation (in) |
|---|---|---|
| 165 | 'RightSidedGeneralDipoleDipole' 22 24 1 9 | 1.52 |
| 166 | 'RightSidedGeneralDipoleDipole' 22 24 3 7 | 1.59 |
| 167 | 'RightSidedGeneralDipoleDipole' 22 24 3 9 | 1.47 |
| 168 | 'RightSidedGeneralDipoleDipole' 22 24 5 9 | 1.41 |
| 169 | 'RightSidedGeneralDipoleDipole' 24 26 1 5 | 1.96 |
| 170 | 'RightSidedGeneralDipoleDipole' 24 26 1 7 | 1.84 |
| 171 | 'RightSidedGeneralDipoleDipole' 24 26 1 9 | 1.71 |
| 172 | 'RightSidedGeneralDipoleDipole' 24 26 1 11 | 1.56 |
| 173 | 'RightSidedGeneralDipoleDipole' 24 26 3 7 | 1.77 |
| 174 | 'RightSidedGeneralDipoleDipole' 24 26 3 9 | 1.65 |
| 175 | 'RightSidedGeneralDipoleDipole' 24 26 3 11 | 1.52 |
| 176 | 'RightSidedGeneralDipoleDipole' 24 26 5 9 | 1.59 |
| 177 | 'RightSidedGeneralDipoleDipole' 24 26 5 11 | 1.47 |
| 178 | 'RightSidedGeneralDipoleDipole' 24 26 7 11 | 1.41 |
| 179 | 'RightSidedGeneralDipoleDipole' 26 28 1 5 | 2.14 |
| 180 | 'RightSidedGeneralDipoleDipole' 26 28 1 7 | 2.02 |
| 181 | 'RightSidedGeneralDipoleDipole' 26 28 1 9 | 1.90 |
| 182 | 'RightSidedGeneralDipoleDipole' 26 28 1 11 | 1.75 |
| 183 | 'RightSidedGeneralDipoleDipole' 26 28 1 13 | 1.60 |
| 184 | 'RightSidedGeneralDipoleDipole' 26 28 3 7 | 1.96 |
| 185 | 'RightSidedGeneralDipoleDipole' 26 28 3 9 | 1.84 |
| 186 | 'RightSidedGeneralDipoleDipole' 26 28 3 11 | 1.71 |
| 187 | 'RightSidedGeneralDipoleDipole' 26 28 3 13 | 1.56 |
| 188 | 'RightSidedGeneralDipoleDipole' 26 28 5 9 | 1.77 |
| 189 | 'RightSidedGeneralDipoleDipole' 26 28 5 11 | 1.65 |
| 190 | 'RightSidedGeneralDipoleDipole' 26 28 5 13 | 1.52 |
| 191 | 'RightSidedGeneralDipoleDipole' 26 28 7 11 | 1.59 |
| 192 | 'RightSidedGeneralDipoleDipole' 26 28 7 13 | 1.47 |
| 193 | 'RightSidedGeneralDipoleDipole' 26 28 9 13 | 1.41 |
| 194 | 'RightSidedGeneralDipoleDipole' 28 30 1 5 | 2.32 |
| 195 | 'RightSidedGeneralDipoleDipole' 28 30 1 7 | 2.21 |
| 196 | 'RightSidedGeneralDipoleDipole' 28 30 1 9 | 2.08 |
| 197 | 'RightSidedGeneralDipoleDipole' 28 30 1 11 | 1.95 |
| 198 | 'RightSidedGeneralDipoleDipole' 28 30 1 13 | 1.80 |
| 199 | 'RightSidedGeneralDipoleDipole' 28 30 1 15 | 1.63 |
| 200 | 'RightSidedGeneralDipoleDipole' 28 30 3 7 | 2.14 |
| 201 | 'RightSidedGeneralDipoleDipole' 28 30 3 9 | 2.02 |
| 202 | 'RightSidedGeneralDipoleDipole' 28 30 3 11 | 1.90 |
| 203 | 'RightSidedGeneralDipoleDipole' 28 30 3 13 | 1.75 |
| 204 | 'RightSidedGeneralDipoleDipole' 28 30 3 15 | 1.60 |
| 205 | 'RightSidedGeneralDipoleDipole' 28 30 5 9 | 1.96 |

FIG. 22C (Cont. 1)

| # | Array Type, C1, C2, P1, P1 | Depth of Investigation (in) |
|---|---|---|
| 206 | 'RightSidedGeneralDipoleDipole' 28 30 5 11 | 1.84 |
| 207 | 'RightSidedGeneralDipoleDipole' 28 30 5 13 | 1.71 |
| 208 | 'RightSidedGeneralDipoleDipole' 28 30 5 15 | 1.56 |
| 209 | 'RightSidedGeneralDipoleDipole' 28 30 7 11 | 1.77 |
| 210 | 'RightSidedGeneralDipoleDipole' 28 30 7 13 | 1.65 |
| 211 | 'RightSidedGeneralDipoleDipole' 28 30 7 15 | 1.52 |
| 212 | 'RightSidedGeneralDipoleDipole' 28 30 9 13 | 1.59 |
| 213 | 'RightSidedGeneralDipoleDipole' 28 30 9 15 | 1.47 |
| 214 | 'RightSidedGeneralDipoleDipole' 28 30 11 15 | 1.41 |
| 215 | 'RightSidedGeneralDipoleDipole' 16 20 1 3 | 1.41 |
| 216 | 'RightSidedGeneralDipoleDipole' 18 22 1 3 | 1.59 |
| 217 | 'RightSidedGeneralDipoleDipole' 18 22 3 5 | 1.41 |
| 218 | 'RightSidedGeneralDipoleDipole' 20 24 1 3 | 1.77 |
| 219 | 'RightSidedGeneralDipoleDipole' 20 24 1 7 | 1.54 |
| 220 | 'RightSidedGeneralDipoleDipole' 20 24 3 5 | 1.59 |
| 221 | 'RightSidedGeneralDipoleDipole' 20 24 5 7 | 1.41 |
| 222 | 'RightSidedGeneralDipoleDipole' 22 26 1 3 | 1.96 |
| 223 | 'RightSidedGeneralDipoleDipole' 22 26 1 7 | 1.73 |
| 224 | 'RightSidedGeneralDipoleDipole' 22 26 1 9 | 1.59 |
| 225 | 'RightSidedGeneralDipoleDipole' 22 26 3 5 | 1.77 |
| 226 | 'RightSidedGeneralDipoleDipole' 22 26 3 9 | 1.54 |
| 227 | 'RightSidedGeneralDipoleDipole' 22 26 5 7 | 1.59 |
| 228 | 'RightSidedGeneralDipoleDipole' 22 26 7 9 | 1.41 |
| 229 | 'RightSidedGeneralDipoleDipole' 24 28 1 3 | 2.14 |
| 230 | 'RightSidedGeneralDipoleDipole' 24 28 1 7 | 1.92 |
| 231 | 'RightSidedGeneralDipoleDipole' 24 28 1 9 | 1.78 |
| 232 | 'RightSidedGeneralDipoleDipole' 24 28 1 11 | 1.64 |
| 233 | 'RightSidedGeneralDipoleDipole' 24 28 3 5 | 1.96 |
| 234 | 'RightSidedGeneralDipoleDipole' 24 28 3 9 | 1.73 |
| 235 | 'RightSidedGeneralDipoleDipole' 24 28 3 11 | 1.59 |
| 236 | 'RightSidedGeneralDipoleDipole' 24 28 5 7 | 1.77 |
| 237 | 'RightSidedGeneralDipoleDipole' 24 28 5 11 | 1.54 |
| 238 | 'RightSidedGeneralDipoleDipole' 24 28 7 9 | 1.59 |
| 239 | 'RightSidedGeneralDipoleDipole' 24 28 9 11 | 1.41 |
| 240 | 'RightSidedGeneralDipoleDipole' 26 30 1 3 | 2.32 |
| 241 | 'RightSidedGeneralDipoleDipole' 26 30 1 7 | 2.10 |
| 242 | 'RightSidedGeneralDipoleDipole' 26 30 1 9 | 1.97 |
| 243 | 'RightSidedGeneralDipoleDipole' 26 30 1 11 | 1.83 |
| 244 | 'RightSidedGeneralDipoleDipole' 26 30 1 13 | 1.68 |
| 245 | 'RightSidedGeneralDipoleDipole' 26 30 3 5 | 2.14 |

FIG. 22C (Cont. 2)

| # | Array Type, C1, C2, P1, P1 | Depth of Investigation (in) |
|---|---|---|
| 246 | 'RightSidedGeneralDipoleDipole' 26 30 3 9 | 1.92 |
| 247 | 'RightSidedGeneralDipoleDipole' 26 30 3 11 | 1.78 |
| 248 | 'RightSidedGeneralDipoleDipole' 26 30 3 13 | 1.64 |
| 249 | 'RightSidedGeneralDipoleDipole' 26 30 5 7 | 1.96 |
| 250 | 'RightSidedGeneralDipoleDipole' 26 30 5 11 | 1.73 |
| 251 | 'RightSidedGeneralDipoleDipole' 26 30 5 13 | 1.59 |
| 252 | 'RightSidedGeneralDipoleDipole' 26 30 7 9 | 1.77 |
| 253 | 'RightSidedGeneralDipoleDipole' 26 30 7 13 | 1.54 |
| 254 | 'RightSidedGeneralDipoleDipole' 26 30 9 11 | 1.59 |
| 255 | 'RightSidedGeneralDipoleDipole' 26 30 11 13 | 1.41 |
| 256 | 'RightSidedGeneralDipoleDipole' 16 22 1 3 | 1.47 |
| 257 | 'RightSidedGeneralDipoleDipole' 18 24 1 3 | 1.65 |
| 258 | 'RightSidedGeneralDipoleDipole' 18 24 1 5 | 1.54 |
| 259 | 'RightSidedGeneralDipoleDipole' 18 24 3 5 | 1.47 |
| 260 | 'RightSidedGeneralDipoleDipole' 20 26 1 3 | 1.84 |
| 261 | 'RightSidedGeneralDipoleDipole' 20 26 1 5 | 1.73 |
| 262 | 'RightSidedGeneralDipoleDipole' 20 26 3 5 | 1.65 |
| 263 | 'RightSidedGeneralDipoleDipole' 20 26 3 7 | 1.54 |
| 264 | 'RightSidedGeneralDipoleDipole' 20 26 5 7 | 1.47 |
| 265 | 'RightSidedGeneralDipoleDipole' 22 28 1 3 | 2.02 |
| 266 | 'RightSidedGeneralDipoleDipole' 22 28 1 5 | 1.92 |
| 267 | 'RightSidedGeneralDipoleDipole' 22 28 1 9 | 1.66 |
| 268 | 'RightSidedGeneralDipoleDipole' 22 28 3 5 | 1.84 |
| 269 | 'RightSidedGeneralDipoleDipole' 22 28 3 7 | 1.73 |
| 270 | 'RightSidedGeneralDipoleDipole' 22 28 5 7 | 1.65 |
| 271 | 'RightSidedGeneralDipoleDipole' 22 28 5 9 | 1.54 |
| 272 | 'RightSidedGeneralDipoleDipole' 22 28 7 9 | 1.47 |
| 273 | 'RightSidedGeneralDipoleDipole' 24 30 1 3 | 2.21 |
| 274 | 'RightSidedGeneralDipoleDipole' 24 30 1 5 | 2.10 |
| 275 | 'RightSidedGeneralDipoleDipole' 24 30 1 9 | 1.85 |
| 276 | 'RightSidedGeneralDipoleDipole' 24 30 1 11 | 1.70 |
| 277 | 'RightSidedGeneralDipoleDipole' 24 30 3 5 | 2.02 |
| 278 | 'RightSidedGeneralDipoleDipole' 24 30 3 7 | 1.92 |
| 279 | 'RightSidedGeneralDipoleDipole' 24 30 3 11 | 1.66 |
| 280 | 'RightSidedGeneralDipoleDipole' 24 30 5 7 | 1.84 |
| 281 | 'RightSidedGeneralDipoleDipole' 24 30 5 9 | 1.73 |
| 282 | 'RightSidedGeneralDipoleDipole' 24 30 7 9 | 1.65 |
| 283 | 'RightSidedGeneralDipoleDipole' 24 30 7 11 | 1.54 |
| 284 | 'RightSidedGeneralDipoleDipole' 24 30 9 11 | 1.47 |
| 285 | 'RightSidedGeneralDipoleDipole' 16 24 1 3 | 1.52 |

FIG. 22D (Cont. 1)

| # | Array Type, C1, C2, P1, P1 | Depth of Investigation (in) |
|---|---|---|
| 286 | 'RightSidedGeneralDipoleDipole' 18 26 1 3 | 1.71 |
| 287 | 'RightSidedGeneralDipoleDipole' 18 26 1 5 | 1.59 |
| 288 | 'RightSidedGeneralDipoleDipole' 18 26 3 5 | 1.52 |
| 289 | 'RightSidedGeneralDipoleDipole' 20 28 1 3 | 1.90 |
| 290 | 'RightSidedGeneralDipoleDipole' 20 28 1 5 | 1.78 |
| 291 | 'RightSidedGeneralDipoleDipole' 20 28 1 7 | 1.66 |
| 292 | 'RightSidedGeneralDipoleDipole' 20 28 3 5 | 1.71 |
| 293 | 'RightSidedGeneralDipoleDipole' 20 28 3 7 | 1.59 |
| 294 | 'RightSidedGeneralDipoleDipole' 20 28 5 7 | 1.52 |
| 295 | 'RightSidedGeneralDipoleDipole' 22 30 1 3 | 2.08 |
| 296 | 'RightSidedGeneralDipoleDipole' 22 30 1 5 | 1.97 |
| 297 | 'RightSidedGeneralDipoleDipole' 22 30 1 7 | 1.85 |
| 298 | 'RightSidedGeneralDipoleDipole' 22 30 3 5 | 1.90 |
| 299 | 'RightSidedGeneralDipoleDipole' 22 30 3 7 | 1.78 |
| 300 | 'RightSidedGeneralDipoleDipole' 22 30 3 9 | 1.66 |
| 301 | 'RightSidedGeneralDipoleDipole' 22 30 5 7 | 1.71 |
| 302 | 'RightSidedGeneralDipoleDipole' 22 30 5 9 | 1.59 |
| 303 | 'RightSidedGeneralDipoleDipole' 22 30 7 9 | 1.52 |
| 304 | 'RightSidedGeneralDipoleDipole' 16 26 1 3 | 1.56 |
| 305 | 'RightSidedGeneralDipoleDipole' 18 28 1 3 | 1.75 |
| 306 | 'RightSidedGeneralDipoleDipole' 18 28 1 5 | 1.64 |
| 307 | 'RightSidedGeneralDipoleDipole' 18 28 3 5 | 1.56 |
| 308 | 'RightSidedGeneralDipoleDipole' 20 30 1 3 | 1.95 |
| 309 | 'RightSidedGeneralDipoleDipole' 20 30 1 5 | 1.83 |
| 310 | 'RightSidedGeneralDipoleDipole' 20 30 1 7 | 1.70 |
| 311 | 'RightSidedGeneralDipoleDipole' 20 30 3 5 | 1.75 |
| 312 | 'RightSidedGeneralDipoleDipole' 20 30 3 7 | 1.64 |
| 313 | 'RightSidedGeneralDipoleDipole' 20 30 5 7 | 1.56 |
| 314 | 'RightSidedGeneralDipoleDipole' 16 28 1 3 | 1.60 |
| 315 | 'RightSidedGeneralDipoleDipole' 18 30 1 3 | 1.80 |
| 316 | 'RightSidedGeneralDipoleDipole' 18 30 1 5 | 1.68 |
| 317 | 'RightSidedGeneralDipoleDipole' 18 30 3 5 | 1.60 |
| 318 | 'RightSidedGeneralDipoleDipole' 16 30 1 3 | 1.63 |
| 319 | 'LeftSidedGeneralDipoleDipole' 2 4 17 21 | 1.41 |
| 320 | 'LeftSidedGeneralDipoleDipole' 2 4 17 23 | 1.47 |
| 321 | 'LeftSidedGeneralDipoleDipole' 2 4 17 25 | 1.52 |
| 322 | 'LeftSidedGeneralDipoleDipole' 2 4 17 27 | 1.56 |
| 323 | 'LeftSidedGeneralDipoleDipole' 2 4 17 29 | 1.60 |
| 324 | 'LeftSidedGeneralDipoleDipole' 2 4 17 31 | 1.63 |
| 325 | 'LeftSidedGeneralDipoleDipole' 2 4 19 23 | 1.59 |
| 326 | 'LeftSidedGeneralDipoleDipole' 2 4 19 25 | 1.65 |

FIG. 22D (Cont. 2)

| # | Array Type, C1, C2, P1, P1 | Depth of Investigation (in) |
|---|---|---|
| 327 | 'LeftSidedGeneralDipoleDipole' 2 4 19 27 | 1.71 |
| 328 | 'LeftSidedGeneralDipoleDipole' 2 4 19 29 | 1.75 |
| 329 | 'LeftSidedGeneralDipoleDipole' 2 4 19 31 | 1.80 |
| 330 | 'LeftSidedGeneralDipoleDipole' 2 4 21 25 | 1.77 |
| 331 | 'LeftSidedGeneralDipoleDipole' 2 4 21 27 | 1.84 |
| 332 | 'LeftSidedGeneralDipoleDipole' 2 4 21 29 | 1.90 |
| 333 | 'LeftSidedGeneralDipoleDipole' 2 4 21 31 | 1.95 |
| 334 | 'LeftSidedGeneralDipoleDipole' 2 4 23 27 | 1.96 |
| 335 | 'LeftSidedGeneralDipoleDipole' 2 4 23 29 | 2.02 |
| 336 | 'LeftSidedGeneralDipoleDipole' 2 4 23 31 | 2.08 |
| 337 | 'LeftSidedGeneralDipoleDipole' 2 4 25 29 | 2.14 |
| 338 | 'LeftSidedGeneralDipoleDipole' 2 4 25 31 | 2.21 |
| 339 | 'LeftSidedGeneralDipoleDipole' 2 4 27 31 | 2.32 |
| 340 | 'LeftSidedGeneralDipoleDipole' 4 6 19 23 | 1.41 |
| 341 | 'LeftSidedGeneralDipoleDipole' 4 6 19 25 | 1.47 |
| 342 | 'LeftSidedGeneralDipoleDipole' 4 6 19 27 | 1.52 |
| 343 | 'LeftSidedGeneralDipoleDipole' 4 6 19 29 | 1.56 |
| 344 | 'LeftSidedGeneralDipoleDipole' 4 6 19 31 | 1.60 |
| 345 | 'LeftSidedGeneralDipoleDipole' 4 6 21 25 | 1.59 |
| 346 | 'LeftSidedGeneralDipoleDipole' 4 6 21 27 | 1.65 |
| 347 | 'LeftSidedGeneralDipoleDipole' 4 6 21 29 | 1.71 |
| 348 | 'LeftSidedGeneralDipoleDipole' 4 6 21 31 | 1.75 |
| 349 | 'LeftSidedGeneralDipoleDipole' 4 6 23 27 | 1.77 |
| 350 | 'LeftSidedGeneralDipoleDipole' 4 6 23 29 | 1.84 |
| 351 | 'LeftSidedGeneralDipoleDipole' 4 6 23 31 | 1.90 |
| 352 | 'LeftSidedGeneralDipoleDipole' 4 6 25 29 | 1.96 |
| 353 | 'LeftSidedGeneralDipoleDipole' 4 6 25 31 | 2.02 |
| 354 | 'LeftSidedGeneralDipoleDipole' 4 6 27 31 | 2.14 |
| 355 | 'LeftSidedGeneralDipoleDipole' 6 8 21 25 | 1.41 |
| 356 | 'LeftSidedGeneralDipoleDipole' 6 8 21 27 | 1.47 |
| 357 | 'LeftSidedGeneralDipoleDipole' 6 8 21 29 | 1.52 |
| 358 | 'LeftSidedGeneralDipoleDipole' 6 8 21 31 | 1.56 |
| 359 | 'LeftSidedGeneralDipoleDipole' 6 8 23 27 | 1.59 |
| 360 | 'LeftSidedGeneralDipoleDipole' 6 8 23 29 | 1.65 |
| 361 | 'LeftSidedGeneralDipoleDipole' 6 8 23 31 | 1.71 |
| 362 | 'LeftSidedGeneralDipoleDipole' 6 8 25 29 | 1.77 |
| 363 | 'LeftSidedGeneralDipoleDipole' 6 8 25 31 | 1.84 |
| 364 | 'LeftSidedGeneralDipoleDipole' 6 8 27 31 | 1.96 |
| 365 | 'LeftSidedGeneralDipoleDipole' 8 10 23 27 | 1.41 |
| 366 | 'LeftSidedGeneralDipoleDipole' 8 10 23 29 | 1.47 |
| 367 | 'LeftSidedGeneralDipoleDipole' 8 10 23 31 | 1.52 |

FIG. 22E (Cont. 1)

| # | Array Type, C1, C2, P1, P1 | Depth of Investigation (in) |
|---|---|---|
| 368 | 'LeftSidedGeneralDipoleDipole' 8 10 25 29 | 1.59 |
| 369 | 'LeftSidedGeneralDipoleDipole' 8 10 25 31 | 1.65 |
| 370 | 'LeftSidedGeneralDipoleDipole' 8 10 27 31 | 1.77 |
| 371 | 'LeftSidedGeneralDipoleDipole' 10 12 25 29 | 1.41 |
| 372 | 'LeftSidedGeneralDipoleDipole' 10 12 25 31 | 1.47 |
| 373 | 'LeftSidedGeneralDipoleDipole' 10 12 27 31 | 1.59 |
| 374 | 'LeftSidedGeneralDipoleDipole' 12 14 27 31 | 1.41 |
| 375 | 'LeftSidedGeneralDipoleDipole' 2 6 19 21 | 1.41 |
| 376 | 'LeftSidedGeneralDipoleDipole' 2 6 19 25 | 1.54 |
| 377 | 'LeftSidedGeneralDipoleDipole' 2 6 19 27 | 1.59 |
| 378 | 'LeftSidedGeneralDipoleDipole' 2 6 19 29 | 1.64 |
| 379 | 'LeftSidedGeneralDipoleDipole' 2 6 19 31 | 1.68 |
| 380 | 'LeftSidedGeneralDipoleDipole' 2 6 21 23 | 1.59 |
| 381 | 'LeftSidedGeneralDipoleDipole' 2 6 21 27 | 1.73 |
| 382 | 'LeftSidedGeneralDipoleDipole' 2 6 21 29 | 1.78 |
| 383 | 'LeftSidedGeneralDipoleDipole' 2 6 21 31 | 1.83 |
| 384 | 'LeftSidedGeneralDipoleDipole' 2 6 23 25 | 1.77 |
| 385 | 'LeftSidedGeneralDipoleDipole' 2 6 23 29 | 1.92 |
| 386 | 'LeftSidedGeneralDipoleDipole' 2 6 23 31 | 1.97 |
| 387 | 'LeftSidedGeneralDipoleDipole' 2 6 25 27 | 1.96 |
| 388 | 'LeftSidedGeneralDipoleDipole' 2 6 25 31 | 2.10 |
| 389 | 'LeftSidedGeneralDipoleDipole' 2 6 27 29 | 2.14 |
| 390 | 'LeftSidedGeneralDipoleDipole' 2 6 29 31 | 2.32 |
| 391 | 'LeftSidedGeneralDipoleDipole' 4 8 21 23 | 1.41 |
| 392 | 'LeftSidedGeneralDipoleDipole' 4 8 21 27 | 1.54 |
| 393 | 'LeftSidedGeneralDipoleDipole' 4 8 21 29 | 1.59 |
| 394 | 'LeftSidedGeneralDipoleDipole' 4 8 21 31 | 1.64 |
| 395 | 'LeftSidedGeneralDipoleDipole' 4 8 23 25 | 1.59 |
| 396 | 'LeftSidedGeneralDipoleDipole' 4 8 23 29 | 1.73 |
| 397 | 'LeftSidedGeneralDipoleDipole' 4 8 23 31 | 1.78 |
| 398 | 'LeftSidedGeneralDipoleDipole' 4 8 25 27 | 1.77 |
| 399 | 'LeftSidedGeneralDipoleDipole' 4 8 25 31 | 1.92 |
| 400 | 'LeftSidedGeneralDipoleDipole' 4 8 27 29 | 1.96 |
| 401 | 'LeftSidedGeneralDipoleDipole' 4 8 29 31 | 2.14 |
| 402 | 'LeftSidedGeneralDipoleDipole' 6 10 23 25 | 1.41 |
| 403 | 'LeftSidedGeneralDipoleDipole' 6 10 23 29 | 1.54 |
| 404 | 'LeftSidedGeneralDipoleDipole' 6 10 23 31 | 1.59 |
| 405 | 'LeftSidedGeneralDipoleDipole' 6 10 25 27 | 1.59 |
| 406 | 'LeftSidedGeneralDipoleDipole' 6 10 25 31 | 1.73 |
| 407 | 'LeftSidedGeneralDipoleDipole' 6 10 27 29 | 1.77 |
| 408 | 'LeftSidedGeneralDipoleDipole' 6 10 29 31 | 1.96 |

FIG. 22E (Cont. 2)

| # | Array Type, C1, C2, P1, P1 | Depth of Investigation (in) |
|---|---|---|
| 409 | 'LeftSidedGeneralDipoleDipole' 8 12 25 27 | 1.41 |
| 410 | 'LeftSidedGeneralDipoleDipole' 8 12 25 31 | 1.54 |
| 411 | 'LeftSidedGeneralDipoleDipole' 8 12 27 29 | 1.59 |
| 412 | 'LeftSidedGeneralDipoleDipole' 8 12 29 31 | 1.77 |
| 413 | 'LeftSidedGeneralDipoleDipole' 10 14 27 29 | 1.41 |
| 414 | 'LeftSidedGeneralDipoleDipole' 10 14 29 31 | 1.59 |
| 415 | 'LeftSidedGeneralDipoleDipole' 12 16 29 31 | 1.41 |
| 416 | 'LeftSidedGeneralDipoleDipole' 2 8 21 23 | 1.47 |
| 417 | 'LeftSidedGeneralDipoleDipole' 2 8 21 25 | 1.54 |
| 418 | 'LeftSidedGeneralDipoleDipole' 2 8 21 29 | 1.66 |
| 419 | 'LeftSidedGeneralDipoleDipole' 2 8 21 31 | 1.70 |
| 420 | 'LeftSidedGeneralDipoleDipole' 2 8 23 25 | 1.65 |
| 421 | 'LeftSidedGeneralDipoleDipole' 2 8 23 27 | 1.73 |
| 422 | 'LeftSidedGeneralDipoleDipole' 2 8 23 31 | 1.85 |
| 423 | 'LeftSidedGeneralDipoleDipole' 2 8 25 27 | 1.84 |
| 424 | 'LeftSidedGeneralDipoleDipole' 2 8 25 29 | 1.92 |
| 425 | 'LeftSidedGeneralDipoleDipole' 2 8 27 29 | 2.02 |
| 426 | 'LeftSidedGeneralDipoleDipole' 2 8 27 31 | 2.10 |
| 427 | 'LeftSidedGeneralDipoleDipole' 2 8 29 31 | 2.21 |
| 428 | 'LeftSidedGeneralDipoleDipole' 4 10 23 25 | 1.47 |
| 429 | 'LeftSidedGeneralDipoleDipole' 4 10 23 27 | 1.54 |
| 430 | 'LeftSidedGeneralDipoleDipole' 4 10 23 31 | 1.66 |
| 431 | 'LeftSidedGeneralDipoleDipole' 4 10 25 27 | 1.65 |
| 432 | 'LeftSidedGeneralDipoleDipole' 4 10 25 29 | 1.73 |
| 433 | 'LeftSidedGeneralDipoleDipole' 4 10 27 29 | 1.84 |
| 434 | 'LeftSidedGeneralDipoleDipole' 4 10 27 31 | 1.92 |
| 435 | 'LeftSidedGeneralDipoleDipole' 4 10 29 31 | 2.02 |
| 436 | 'LeftSidedGeneralDipoleDipole' 6 12 25 27 | 1.47 |
| 437 | 'LeftSidedGeneralDipoleDipole' 6 12 25 29 | 1.54 |
| 438 | 'LeftSidedGeneralDipoleDipole' 6 12 27 29 | 1.65 |
| 439 | 'LeftSidedGeneralDipoleDipole' 6 12 27 31 | 1.73 |
| 440 | 'LeftSidedGeneralDipoleDipole' 6 12 29 31 | 1.84 |
| 441 | 'LeftSidedGeneralDipoleDipole' 8 14 27 29 | 1.47 |
| 442 | 'LeftSidedGeneralDipoleDipole' 8 14 27 31 | 1.54 |
| 443 | 'LeftSidedGeneralDipoleDipole' 8 14 29 31 | 1.65 |
| 444 | 'LeftSidedGeneralDipoleDipole' 10 16 29 31 | 1.47 |
| 445 | 'LeftSidedGeneralDipoleDipole' 2 10 23 25 | 1.52 |
| 446 | 'LeftSidedGeneralDipoleDipole' 2 10 23 27 | 1.59 |
| 447 | 'LeftSidedGeneralDipoleDipole' 2 10 23 29 | 1.66 |
| 448 | 'LeftSidedGeneralDipoleDipole' 2 10 25 27 | 1.71 |
| 449 | 'LeftSidedGeneralDipoleDipole' 2 10 25 29 | 1.78 |

FIG. 22F (Cont. 1)

| # | Array Type, C1, C2, P1, P1 | Depth of Investigation (in) |
|---|---|---|
| 450 | 'LeftSidedGeneralDipoleDipole' 2 10 25 31 | 1.85 |
| 451 | 'LeftSidedGeneralDipoleDipole' 2 10 27 29 | 1.90 |
| 452 | 'LeftSidedGeneralDipoleDipole' 2 10 27 31 | 1.97 |
| 453 | 'LeftSidedGeneralDipoleDipole' 2 10 29 31 | 2.08 |
| 454 | 'LeftSidedGeneralDipoleDipole' 4 12 25 27 | 1.52 |
| 455 | 'LeftSidedGeneralDipoleDipole' 4 12 25 29 | 1.59 |
| 456 | 'LeftSidedGeneralDipoleDipole' 4 12 25 31 | 1.66 |
| 457 | 'LeftSidedGeneralDipoleDipole' 4 12 27 29 | 1.71 |
| 458 | 'LeftSidedGeneralDipoleDipole' 4 12 27 31 | 1.78 |
| 459 | 'LeftSidedGeneralDipoleDipole' 4 12 29 31 | 1.90 |
| 460 | 'LeftSidedGeneralDipoleDipole' 6 14 27 29 | 1.52 |
| 461 | 'LeftSidedGeneralDipoleDipole' 6 14 27 31 | 1.59 |
| 462 | 'LeftSidedGeneralDipoleDipole' 6 14 29 31 | 1.71 |
| 463 | 'LeftSidedGeneralDipoleDipole' 8 16 29 31 | 1.52 |
| 464 | 'LeftSidedGeneralDipoleDipole' 2 12 25 27 | 1.56 |
| 465 | 'LeftSidedGeneralDipoleDipole' 2 12 25 29 | 1.64 |
| 466 | 'LeftSidedGeneralDipoleDipole' 2 12 25 31 | 1.70 |
| 467 | 'LeftSidedGeneralDipoleDipole' 2 12 27 29 | 1.75 |
| 468 | 'LeftSidedGeneralDipoleDipole' 2 12 27 31 | 1.83 |
| 469 | 'LeftSidedGeneralDipoleDipole' 2 12 29 31 | 1.95 |
| 470 | 'LeftSidedGeneralDipoleDipole' 4 14 27 29 | 1.56 |
| 471 | 'LeftSidedGeneralDipoleDipole' 4 14 27 31 | 1.64 |
| 472 | 'LeftSidedGeneralDipoleDipole' 4 14 29 31 | 1.75 |
| 473 | 'LeftSidedGeneralDipoleDipole' 6 16 29 31 | 1.56 |
| 474 | 'LeftSidedGeneralDipoleDipole' 2 14 27 29 | 1.60 |
| 475 | 'LeftSidedGeneralDipoleDipole' 2 14 27 31 | 1.68 |
| 476 | 'LeftSidedGeneralDipoleDipole' 2 14 29 31 | 1.80 |
| 477 | 'LeftSidedGeneralDipoleDipole' 4 16 29 31 | 1.60 |
| 478 | 'LeftSidedGeneralDipoleDipole' 2 16 29 31 | 1.63 |
| 479 | 'WennerSchlumberger' 2 10 5 7 | 0.52 |
| 480 | 'WennerSchlumberger' 4 12 7 9 | 0.52 |
| 481 | 'WennerSchlumberger' 6 14 9 11 | 0.52 |
| 482 | 'WennerSchlumberger' 8 16 11 13 | 0.52 |
| 483 | 'WennerSchlumberger' 10 18 13 15 | 0.52 |
| 484 | 'WennerSchlumberger' 12 20 15 17 | 0.52 |
| 485 | 'WennerSchlumberger' 14 22 17 19 | 0.52 |
| 486 | 'WennerSchlumberger' 16 24 19 21 | 0.52 |
| 487 | 'WennerSchlumberger' 18 26 21 23 | 0.52 |
| 488 | 'WennerSchlumberger' 20 28 23 25 | 0.52 |
| 489 | 'WennerSchlumberger' 22 30 25 27 | 0.52 |
| 490 | 'WennerSchlumberger' 2 12 5 9 | 0.59 |

FIG. 22F (Cont. 2)

| # | Array Type, C1, C2, P1, P1 | Depth of Investigation (in) |
|---|---|---|
| 491 | 'WennerSchlumberger' 4 14 7 11 | 0.59 |
| 492 | 'WennerSchlumberger' 6 16 9 13 | 0.59 |
| 493 | 'WennerSchlumberger' 8 18 11 15 | 0.59 |
| 494 | 'WennerSchlumberger' 10 20 13 17 | 0.59 |
| 495 | 'WennerSchlumberger' 12 22 15 19 | 0.59 |
| 496 | 'WennerSchlumberger' 14 24 17 21 | 0.59 |
| 497 | 'WennerSchlumberger' 16 26 19 23 | 0.59 |
| 498 | 'WennerSchlumberger' 18 28 21 25 | 0.59 |
| 499 | 'WennerSchlumberger' 20 30 23 27 | 0.59 |
| 500 | 'WennerSchlumberger' 2 14 5 11 | 0.64 |
| 501 | 'WennerSchlumberger' 2 14 7 9 | 0.81 |
| 502 | 'WennerSchlumberger' 4 16 7 13 | 0.64 |
| 503 | 'WennerSchlumberger' 4 16 9 11 | 0.81 |
| 504 | 'WennerSchlumberger' 6 18 9 15 | 0.64 |
| 505 | 'WennerSchlumberger' 6 18 11 13 | 0.81 |
| 506 | 'WennerSchlumberger' 8 20 11 17 | 0.64 |
| 507 | 'WennerSchlumberger' 8 20 13 15 | 0.81 |
| 508 | 'WennerSchlumberger' 10 22 13 19 | 0.64 |
| 509 | 'WennerSchlumberger' 10 22 15 17 | 0.81 |
| 510 | 'WennerSchlumberger' 12 24 15 21 | 0.64 |
| 511 | 'WennerSchlumberger' 12 24 17 19 | 0.81 |
| 512 | 'WennerSchlumberger' 14 26 17 23 | 0.64 |
| 513 | 'WennerSchlumberger' 14 26 19 21 | 0.81 |
| 514 | 'WennerSchlumberger' 16 28 19 25 | 0.64 |
| 515 | 'WennerSchlumberger' 16 28 21 23 | 0.81 |
| 516 | 'WennerSchlumberger' 18 30 21 27 | 0.64 |
| 517 | 'WennerSchlumberger' 18 30 23 25 | 0.81 |
| 518 | 'WennerSchlumberger' 2 16 5 13 | 0.68 |
| 519 | 'WennerSchlumberger' 2 16 7 11 | 0.90 |
| 520 | 'WennerSchlumberger' 4 18 7 15 | 0.68 |
| 521 | 'WennerSchlumberger' 4 18 9 13 | 0.90 |
| 522 | 'WennerSchlumberger' 6 20 9 17 | 0.68 |
| 523 | 'WennerSchlumberger' 6 20 11 15 | 0.90 |
| 524 | 'WennerSchlumberger' 8 22 11 19 | 0.68 |
| 525 | 'WennerSchlumberger' 8 22 13 17 | 0.90 |
| 526 | 'WennerSchlumberger' 10 24 13 21 | 0.68 |
| 527 | 'WennerSchlumberger' 10 24 15 19 | 0.90 |
| 528 | 'WennerSchlumberger' 12 26 15 23 | 0.68 |
| 529 | 'WennerSchlumberger' 12 26 17 21 | 0.90 |
| 530 | 'WennerSchlumberger' 14 28 17 25 | 0.68 |
| 531 | 'WennerSchlumberger' 14 28 19 23 | 0.90 |

FIG. 22G (Cont. 1)

| # | Array Type, C1, C2, P1, P1 | Depth of Investigation (in) |
|---|---|---|
| 532 | 'WennerSchlumberger' 16 30 19 27 | 0.68 |
| 533 | 'WennerSchlumberger' 16 30 21 25 | 0.90 |
| 534 | 'WennerSchlumberger' 2 18 5 15 | 0.71 |
| 535 | 'WennerSchlumberger' 2 18 7 13 | 0.97 |
| 536 | 'WennerSchlumberger' 2 18 9 11 | 1.09 |
| 537 | 'WennerSchlumberger' 4 20 7 17 | 0.71 |
| 538 | 'WennerSchlumberger' 4 20 9 15 | 0.97 |
| 539 | 'WennerSchlumberger' 4 20 11 13 | 1.09 |
| 540 | 'WennerSchlumberger' 6 22 9 19 | 0.71 |
| 541 | 'WennerSchlumberger' 6 22 11 17 | 0.97 |
| 542 | 'WennerSchlumberger' 6 22 13 15 | 1.09 |
| 543 | 'WennerSchlumberger' 8 24 11 21 | 0.71 |
| 544 | 'WennerSchlumberger' 8 24 13 19 | 0.97 |
| 545 | 'WennerSchlumberger' 8 24 15 17 | 1.09 |
| 546 | 'WennerSchlumberger' 10 26 13 23 | 0.71 |
| 547 | 'WennerSchlumberger' 10 26 15 21 | 0.97 |
| 548 | 'WennerSchlumberger' 10 26 17 19 | 1.09 |
| 549 | 'WennerSchlumberger' 12 28 15 25 | 0.71 |
| 550 | 'WennerSchlumberger' 12 28 17 23 | 0.97 |
| 551 | 'WennerSchlumberger' 12 28 19 21 | 1.09 |
| 552 | 'WennerSchlumberger' 14 30 17 27 | 0.71 |
| 553 | 'WennerSchlumberger' 14 30 19 25 | 0.97 |
| 554 | 'WennerSchlumberger' 14 30 21 23 | 1.09 |
| 555 | 'WennerSchlumberger' 2 20 5 17 | 0.73 |
| 556 | 'WennerSchlumberger' 2 20 7 15 | 1.02 |
| 557 | 'WennerSchlumberger' 2 20 9 13 | 1.19 |
| 558 | 'WennerSchlumberger' 4 22 7 19 | 0.73 |
| 559 | 'WennerSchlumberger' 4 22 9 17 | 1.02 |
| 560 | 'WennerSchlumberger' 4 22 11 15 | 1.19 |
| 561 | 'WennerSchlumberger' 6 24 9 21 | 0.73 |
| 562 | 'WennerSchlumberger' 6 24 11 19 | 1.02 |
| 563 | 'WennerSchlumberger' 6 24 13 17 | 1.19 |
| 564 | 'WennerSchlumberger' 8 26 11 23 | 0.73 |
| 565 | 'WennerSchlumberger' 8 26 13 21 | 1.02 |
| 566 | 'WennerSchlumberger' 8 26 15 19 | 1.19 |
| 567 | 'WennerSchlumberger' 10 28 13 25 | 0.73 |
| 568 | 'WennerSchlumberger' 10 28 15 23 | 1.02 |
| 569 | 'WennerSchlumberger' 10 28 17 21 | 1.19 |
| 570 | 'WennerSchlumberger' 12 30 15 27 | 0.73 |
| 571 | 'WennerSchlumberger' 12 30 17 25 | 1.02 |
| 572 | 'WennerSchlumberger' 12 30 19 23 | 1.19 |

FIG. 22G (Cont. 2)

| # | Array Type, C1, C2, P1, P1 | Depth of Investigation (in) |
|---|---|---|
| 573 | 'WennerSchlumberger' 2 22 5 19 | 0.75 |
| 574 | 'WennerSchlumberger' 2 22 7 17 | 1.07 |
| 575 | 'WennerSchlumberger' 2 22 9 15 | 1.27 |
| 576 | 'WennerSchlumberger' 2 22 11 13 | 1.37 |
| 577 | 'WennerSchlumberger' 4 24 7 21 | 0.75 |
| 578 | 'WennerSchlumberger' 4 24 9 19 | 1.07 |
| 579 | 'WennerSchlumberger' 4 24 11 17 | 1.27 |
| 580 | 'WennerSchlumberger' 4 24 13 15 | 1.37 |
| 581 | 'WennerSchlumberger' 6 26 9 23 | 0.75 |
| 582 | 'WennerSchlumberger' 6 26 11 21 | 1.07 |
| 583 | 'WennerSchlumberger' 6 26 13 19 | 1.27 |
| 584 | 'WennerSchlumberger' 6 26 15 17 | 1.37 |
| 585 | 'WennerSchlumberger' 8 28 11 25 | 0.75 |
| 586 | 'WennerSchlumberger' 8 28 13 23 | 1.07 |
| 587 | 'WennerSchlumberger' 8 28 15 21 | 1.27 |
| 588 | 'WennerSchlumberger' 8 28 17 19 | 1.37 |
| 589 | 'WennerSchlumberger' 10 30 13 27 | 0.75 |
| 590 | 'WennerSchlumberger' 10 30 15 25 | 1.07 |
| 591 | 'WennerSchlumberger' 10 30 17 23 | 1.27 |
| 592 | 'WennerSchlumberger' 10 30 19 21 | 1.37 |
| 593 | 'WennerSchlumberger' 2 24 5 21 | 0.77 |
| 594 | 'WennerSchlumberger' 2 24 7 19 | 1.11 |
| 595 | 'WennerSchlumberger' 2 24 9 17 | 1.34 |
| 596 | 'WennerSchlumberger' 2 24 11 15 | 1.47 |
| 597 | 'WennerSchlumberger' 4 26 7 23 | 0.77 |
| 598 | 'WennerSchlumberger' 4 26 9 21 | 1.11 |
| 599 | 'WennerSchlumberger' 4 26 11 19 | 1.34 |
| 600 | 'WennerSchlumberger' 4 26 13 17 | 1.47 |
| 601 | 'WennerSchlumberger' 6 28 9 25 | 0.77 |
| 602 | 'WennerSchlumberger' 6 28 11 23 | 1.11 |
| 603 | 'WennerSchlumberger' 6 28 13 21 | 1.34 |
| 604 | 'WennerSchlumberger' 6 28 15 19 | 1.47 |
| 605 | 'WennerSchlumberger' 8 30 11 27 | 0.77 |
| 606 | 'WennerSchlumberger' 8 30 13 25 | 1.11 |
| 607 | 'WennerSchlumberger' 8 30 15 23 | 1.34 |
| 608 | 'WennerSchlumberger' 8 30 17 21 | 1.47 |
| 609 | 'WennerSchlumberger' 2 26 5 23 | 0.78 |
| 610 | 'WennerSchlumberger' 2 26 7 21 | 1.14 |
| 611 | 'WennerSchlumberger' 2 26 9 19 | 1.40 |
| 612 | 'WennerSchlumberger' 2 26 11 17 | 1.57 |
| 613 | 'WennerSchlumberger' 2 26 13 15 | 1.64 |

FIG. 22H (Cont. 1)

| # | Array Type, C1, C2, P1, P1 | Depth of Investigation (in) |
|---|---|---|
| 614 | 'WennerSchlumberger' 4 28 7 25 | 0.78 |
| 615 | 'WennerSchlumberger' 4 28 9 23 | 1.14 |
| 616 | 'WennerSchlumberger' 4 28 11 21 | 1.40 |
| 617 | 'WennerSchlumberger' 4 28 13 19 | 1.57 |
| 618 | 'WennerSchlumberger' 4 28 15 17 | 1.64 |
| 619 | 'WennerSchlumberger' 6 30 9 27 | 0.78 |
| 620 | 'WennerSchlumberger' 6 30 11 25 | 1.14 |
| 621 | 'WennerSchlumberger' 6 30 13 25 | 1.40 |
| 622 | 'WennerSchlumberger' 6 30 15 21 | 1.57 |
| 623 | 'WennerSchlumberger' 6 30 17 19 | 1.64 |
| 624 | 'WennerSchlumberger' 2 28 5 25 | 0.79 |
| 625 | 'WennerSchlumberger' 2 28 7 23 | 1.17 |
| 626 | 'WennerSchlumberger' 2 28 9 21 | 1.45 |
| 627 | 'WennerSchlumberger' 2 28 11 19 | 1.64 |
| 628 | 'WennerSchlumberger' 2 28 13 17 | 1.76 |
| 629 | 'WennerSchlumberger' 4 30 7 27 | 0.79 |
| 630 | 'WennerSchlumberger' 4 30 9 25 | 1.17 |
| 631 | 'WennerSchlumberger' 4 30 11 23 | 1.45 |
| 632 | 'WennerSchlumberger' 4 30 13 21 | 1.64 |
| 633 | 'WennerSchlumberger' 4 30 15 19 | 1.76 |
| 634 | 'WennerSchlumberger' 2 30 5 27 | 0.80 |
| 635 | 'WennerSchlumberger' 2 30 7 25 | 1.20 |
| 636 | 'WennerSchlumberger' 2 30 9 23 | 1.50 |
| 637 | 'WennerSchlumberger' 2 30 11 21 | 1.72 |
| 638 | 'WennerSchlumberger' 2 30 13 19 | 1.85 |
| 639 | 'WennerSchlumberger' 2 30 15 17 | 1.92 |
| 640 | 'LeftSidedGamma' 2 10 7 25 | 0.45 |
| 641 | 'LeftSidedGamma' 2 10 7 27 | 0.46 |
| 642 | 'LeftSidedGamma' 2 10 7 29 | 0.47 |
| 643 | 'LeftSidedGamma' 2 10 7 31 | 0.48 |
| 644 | 'LeftSidedGamma' 4 12 9 27 | 0.45 |
| 645 | 'LeftSidedGamma' 4 12 9 29 | 0.46 |
| 646 | 'LeftSidedGamma' 4 12 9 31 | 0.47 |
| 647 | LeftSidedGamma' 6 14 11 29 | 0.45 |
| 648 | 'LeftSidedGamma' 6 14 11 31 | 0.46 |
| 649 | 'LeftSidedGamma' 8 16 13 31 | 0.45 |
| 650 | 'LeftSidedGamma' 2 12 9 21 | 0.45 |
| 651 | 'LeftSidedGamma' 2 12 9 23 | 0.48 |
| 652 | 'LeftSidedGamma' 2 12 9 25 | 0.51 |
| 653 | 'LeftSidedGamma' 2 12 9 27 | 0.52 |
| 654 | 'LeftSidedGamma' 4 14 11 23 | 0.45 |

FIG. 22H (Cont. 2)

| # | Array Type, C1, C2, P1, P1 | Depth of Investigation (in) |
|---|---|---|
| 655 | 'LeftSidedGamma' 4 14 11 25 | 0.48 |
| 656 | 'LeftSidedGamma' 4 14 11 27 | 0.51 |
| 657 | 'LeftSidedGamma' 4 14 11 29 | 0.52 |
| 658 | 'LeftSidedGamma' 6 16 13 25 | 0.45 |
| 659 | 'LeftSidedGamma' 6 16 13 27 | 0.48 |
| 660 | 'LeftSidedGamma' 6 16 13 29 | 0.51 |
| 661 | 'LeftSidedGamma' 6 16 13 31 | 0.52 |
| 662 | 'LeftSidedGamma' 8 18 15 27 | 0.45 |
| 663 | 'LeftSidedGamma' 8 18 15 29 | 0.48 |
| 664 | 'LeftSidedGamma' 8 18 15 31 | 0.51 |
| 665 | 'LeftSidedGamma' 10 20 17 29 | 0.45 |
| 666 | 'LeftSidedGamma' 10 20 17 31 | 0.48 |
| 667 | 'LeftSidedGamma' 12 22 19 31 | 0.45 |
| 668 | 'LeftSidedGamma' 2 14 11 21 | 0.45 |
| 669 | 'LeftSidedGamma' 2 14 11 23 | 0.50 |
| 670 | 'LeftSidedGamma' 2 14 11 25 | 0.53 |
| 671 | 'LeftSidedGamma' 4 16 13 23 | 0.45 |
| 672 | 'LeftSidedGamma' 4 16 13 25 | 0.50 |
| 673 | 'LeftSidedGamma' 4 16 13 27 | 0.53 |
| 674 | 'LeftSidedGamma' 6 18 15 25 | 0.45 |
| 675 | 'LeftSidedGamma' 6 18 15 27 | 0.50 |
| 676 | 'LeftSidedGamma' 6 18 15 29 | 0.53 |
| 677 | 'LeftSidedGamma' 8 20 17 27 | 0.45 |
| 678 | 'LeftSidedGamma' 8 20 17 29 | 0.50 |
| 679 | 'LeftSidedGamma' 8 20 17 31 | 0.53 |
| 680 | 'LeftSidedGamma' 10 22 19 29 | 0.45 |
| 681 | 'LeftSidedGamma' 10 22 19 31 | 0.50 |
| 682 | 'LeftSidedGamma' 12 24 21 31 | 0.45 |
| 683 | 'LeftSidedGamma' 2 16 13 23 | 0.48 |
| 684 | 'LeftSidedGamma' 2 16 13 25 | 0.53 |
| 685 | 'LeftSidedGamma' 4 18 15 25 | 0.48 |
| 686 | 'LeftSidedGamma' 4 18 15 27 | 0.53 |
| 687 | 'LeftSidedGamma' 6 20 17 27 | 0.48 |
| 688 | 'LeftSidedGamma' 6 20 17 29 | 0.53 |
| 689 | 'LeftSidedGamma' 8 22 19 29 | 0.48 |
| 690 | 'LeftSidedGamma' 8 22 19 31 | 0.53 |
| 691 | 'LeftSidedGamma' 10 24 21 31 | 0.48 |
| 692 | 'LeftSidedGamma' 2 18 15 25 | 0.51 |
| 693 | 'LeftSidedGamma' 4 20 17 27 | 0.51 |
| 694 | 'LeftSidedGamma' 6 22 19 29 | 0.51 |
| 695 | 'LeftSidedGamma' 8 24 21 31 | 0.51 |

FIG. 22I (Cont. 1)

| # | Array Type, C1, C2, P1, P1 | Depth of Investigation (in) |
|---|---|---|
| 696 | 'LeftSidedGamma' 2 20 17 25 | 0.45 |
| 697 | 'LeftSidedGamma' 2 20 17 27 | 0.52 |
| 698 | 'LeftSidedGamma' 4 22 19 27 | 0.45 |
| 699 | 'LeftSidedGamma' 4 22 19 29 | 0.52 |
| 700 | 'LeftSidedGamma' 6 24 21 29 | 0.45 |
| 701 | 'LeftSidedGamma' 6 24 21 31 | 0.52 |
| 702 | 'LeftSidedGamma' 8 26 23 31 | 0.45 |
| 703 | 'LeftSidedGamma' 2 22 19 27 | 0.46 |
| 704 | 'LeftSidedGamma' 4 24 21 29 | 0.46 |
| 705 | 'LeftSidedGamma' 6 26 23 31 | 0.46 |
| 706 | 'LeftSidedGamma' 2 24 21 29 | 0.47 |
| 707 | 'LeftSidedGamma' 4 26 23 31 | 0.47 |
| 708 | 'LeftSidedGamma' 2 26 23 31 | 0.48 |
| 709 | 'RightSidedGamma' 16 24 1 19 | 0.45 |
| 710 | 'RightSidedGamma' 18 26 1 21 | 0.46 |
| 711 | 'RightSidedGamma' 18 26 3 21 | 0.45 |
| 712 | 'RightSidedGamma' 20 28 1 23 | 0.47 |
| 713 | 'RightSidedGamma' 20 28 3 23 | 0.46 |
| 714 | 'RightSidedGamma' 20 28 5 23 | 0.45 |
| 715 | 'RightSidedGamma' 22 30 1 25 | 0.48 |
| 716 | 'RightSidedGamma' 22 30 3 25 | 0.47 |
| 717 | 'RightSidedGamma' 22 30 5 25 | 0.46 |
| 718 | 'RightSidedGamma' 22 30 7 25 | 0.45 |
| 719 | 'RightSidedGamma' 10 20 1 13 | 0.45 |
| 720 | 'RightSidedGamma' 12 22 1 15 | 0.48 |
| 721 | 'RightSidedGamma' 12 22 3 15 | 0.45 |
| 722 | 'RightSidedGamma' 14 24 1 17 | 0.51 |
| 723 | 'RightSidedGamma' 14 24 3 17 | 0.48 |
| 724 | 'RightSidedGamma' 14 24 5 17 | 0.45 |
| 725 | 'RightSidedGamma' 16 26 1 19 | 0.52 |
| 726 | 'RightSidedGamma' 16 26 3 19 | 0.51 |
| 727 | 'RightSidedGamma' 16 26 5 19 | 0.48 |
| 728 | 'RightSidedGamma' 16 26 7 19 | 0.45 |
| 729 | 'RightSidedGamma' 18 28 3 21 | 0.52 |
| 730 | 'RightSidedGamma' 18 28 5 21 | 0.51 |
| 731 | 'RightSidedGamma' 18 28 7 21 | 0.48 |
| 732 | 'RightSidedGamma' 18 28 9 21 | 0.45 |
| 733 | 'RightSidedGamma' 20 30 5 23 | 0.52 |
| 734 | 'RightSidedGamma' 20 30 7 23 | 0.51 |
| 735 | 'RightSidedGamma' 20 30 9 23 | 0.48 |
| 736 | 'RightSidedGamma' 20 30 11 23 | 0.45 |

FIG. 22I (Cont. 2)

| # | Array Type, C1, C2, P1, P1 | Depth of Investigation (in) |
|---|---|---|
| 737 | 'RightSidedGamma' 8 20 1 11 | 0.45 |
| 738 | 'RightSidedGamma' 10 22 1 13 | 0.50 |
| 739 | 'RightSidedGamma' 10 22 3 13 | 0.45 |
| 740 | 'RightSidedGamma' 12 24 1 15 | 0.53 |
| 741 | 'RightSidedGamma' 12 24 3 15 | 0.50 |
| 742 | 'RightSidedGamma' 12 24 5 15 | 0.45 |
| 743 | 'RightSidedGamma' 14 26 3 17 | 0.53 |
| 744 | 'RightSidedGamma' 14 26 5 17 | 0.50 |
| 745 | 'RightSidedGamma' 14 26 3 17 | 0.45 |
| 746 | 'RightSidedGamma' 14 26 5 19 | 0.53 |
| 747 | 'RightSidedGamma' 16 28 5 19 | 0.50 |
| 748 | 'RightSidedGamma' 16 28 7 19 | 0.45 |
| 749 | 'RightSidedGamma' 16 28 9 19 | 0.53 |
| 750 | 'RightSidedGamma' 18 30 9 21 | 0.50 |
| 751 | 'RightSidedGamma' 18 30 11 21 | 0.45 |
| 752 | 'RightSidedGamma' 8 22 1 11 | 0.48 |
| 753 | 'RightSidedGamma' 10 24 1 13 | 0.53 |
| 754 | 'RightSidedGamma' 10 24 3 13 | 0.48 |
| 755 | 'RightSidedGamma' 12 26 3 15 | 0.53 |
| 756 | 'RightSidedGamma' 12 26 5 15 | 0.48 |
| 757 | 'RightSidedGamma' 14 28 5 17 | 0.53 |
| 758 | 'RightSidedGamma' 14 28 7 17 | 0.48 |
| 759 | 'RightSidedGamma' 16 30 7 19 | 0.53 |
| 760 | 'RightSidedGamma' 16 30 7 19 | 0.48 |
| 761 | 'RightSidedGamma' 8 24 1 11 | 0.51 |
| 762 | 'RightSidedGamma' 10 26 3 13 | 0.51 |
| 763 | 'RightSidedGamma' 12 28 5 15 | 0.51 |
| 764 | 'RightSidedGamma' 14 30 7 17 | 0.51 |
| 765 | 'RightSidedGamma' 6 24 1 9 | 0.45 |
| 766 | 'RightSidedGamma' 8 26 1 11 | 0.52 |
| 767 | 'RightSidedGamma' 8 26 3 11 | 0.45 |
| 768 | 'RightSidedGamma' 10 28 3 13 | 0.52 |
| 769 | 'RightSidedGamma' 10 28 5 13 | 0.45 |
| 770 | 'RightSidedGamma' 12 30 5 15 | 0.52 |
| 771 | 'RightSidedGamma' 12 30 7 15 | 0.45 |
| 772 | 'RightSidedGamma' 6 26 1 9 | 0.46 |
| 773 | 'RightSidedGamma' 8 28 3 11 | 0.46 |
| 774 | 'RightSidedGamma' 10 30 5 13 | 0.46 |
| 775 | 'RightSidedGamma' 6 28 1 9 | 0.47 |
| 776 | 'RightSidedGamma' 8 30 3 11 | 0.47 |
| 777 | 'RightSidedGamma' 6 30 1 9 | 0.48 |

FIG. 22J

METHODS FOR DETERMINING THE RELATIVE SPATIAL CHANGE IN SUBSURFACE RESISTIVITIES ACROSS FREQUENCIES IN TISSUE

CROSS REFERENCE TO RELATED APPLICATIONS

This patent application claims priority to U.S. provisional patent application 61/570,655, filed Dec. 14, 2011, titled "ELECTRICAL RESISTIVITY DETECTION OF TISSUE WETNESS"; U.S. provisional patent application 61/696,705, filed Sep. 4, 2012, and titled "A COMBINED ELECTRICAL RESISTIVITY ARRAY USED TO DETERMINE THE SPATIAL RELATIONSHIP OF THE RELATIVE PERCENT DIFFERENCE OF RESISTIVITY BETWEEN MULTIPLE FREQUENCIES IN SOFT TISSUE"; and U.S. provisional patent application 61/719,863, filed Oct. 29, 2012, and titled "DEVICES, SYSTEMS AND METHODS FOR DETERMINING THE RELATIVE SPATIAL CHANGE IN SUBSURFACE RESISTIVITIES ACROSS FREQUENCIES IN TISSUE." Each of these patent applications is herein incorporated by reference in its entirety.

INCORPORATION BY REFERENCE

All publications, including patents and patent applications, mentioned in this specification are herein incorporated by reference in their entirety to the same extent as if each individual publication or patent application was specifically and individually indicated to be incorporated by reference.

FIELD

The inventions described herein relate to methods, devices and systems for non-invasively determining the relative spatial change in subsurface resistivities across frequencies for a region of tissue beneath an array of electrodes placed on the surface of a body. In particular, described herein are methods, devices and systems for determining tissue wetness by determining a distribution of a relative spatial change in subsurface resistivities across frequencies determined from currents applied at high and low frequencies. In one example, the devices, methods and systems may be configured to determine lung wetness; lung wetness determined this way may guide subject treatment, and particularly treatment of heart failure subjects.

BACKGROUND

Tissue water content is an important and informative diagnostic parameter. Dehydration decreases cognitive and physical work capabilities, while the excessive hydration (swelling, edema) is a common symptom of cardiac, hepatic or renal pathology, malnutrition and many other pathologies and diseases. Edema causes muscle aches and pains and may affect the brain, causing headaches and irritability. Edema is a major symptom for deep venous thrombosis. It may be caused by allergies or more serious disorders of the kidney, bladder, heart, and liver, as well as food intolerance, poor diet (high sugar & salt intake), pregnancy, abuse of laxatives, diuretics, drugs, the use of contraceptive pills, hormone replacement therapy, phlebitis, etc.

For example, muscle water content (MWC) is a clinically useful measure of health. Monitoring of muscle water content can serve as an important indicator of body hydration status in athletes during the training as well as in soldiers during deployment. It is generally known that body hypohydration causes severe complications, health and performance problems, and that increasing body water weight loss causes increasing problems: water weight loss of up to 1% causes thirst, 2% may cause vague discomfort and oppression, 4% may cause increased effort for physical work, 5% may cause difficulty concentrating, 6% may cause impairment in exercise temperature regulation, increases in pulse and respiratory rate; 10% may cause spastic muscles; and 15% may cause death. Soldiers commonly dehydrate 2%-5% of body weight due to high rate of water loss from environmental exposure and performing stressful physical work. Dehydration by modest amounts (2%) decreases cognitive and physical work capabilities, while larger water losses have devastating effects on performance and health. Numerous pathologic signs and symptoms due to body dehydration include digestion problems, high blood pressure, muscle cramps, etc. MWC monitoring by an objective instrument may help prevent hazard thresholds. This is important because subjective indicators like thirst can be inadequate.

Control of MWC in athletes and soldiers could help in monitoring total body hydration during long-term endurance exercise or performance in hot weather conditions. In addition, tissue wetness may be particularly helpful in assessing lung wetness, which may be an important metric for treating cardiac disorders such as congestive heart failure.

Congestive heart failure (CHF) causes difficulty breathing because oxygen exchange in the lung is impeded by pulmonary congestion. The vast majority of CHF hospital admissions are because of difficulty breathing. Further, the high rate of CHF readmission (by some estimates approximately 24% within 30 days) is due to re-accumulation or inadequate removal of pulmonary congestion resulting in difficulty breathing. Currently, there is no quantifiable method or metric to identify pulmonary congestion and better prevent difficulty breathing and hospital admission. This problem is growing. In 2010, there was an estimated of 5.8 million CHF cases in the US, with over 670,000 new cases each year.

A subject suffering from CHF may be diagnosed using a physical exam and various imaging techniques to image the subject's chest. Treatment typically includes the use of vasodilators (e.g., ACEI/ARB), beta blockers, and diuretic therapy (e.g., Lasix). Management of treatment often proves difficult and unsuccessful. In particular, diuretic therapy is difficult for subjects and physicians to optimally manage. For example, changes in diet may require frequent changes in the diuretic therapy. Overuse (an underuse) of diuretic therapy may negatively impact clinical outcomes.

Pulmonary congestion is typically the result of high pulmonary blood pressures that drive fluid into the extra-vascular "spongy" interstitial lung tissue. FIG. 1A illustrates a pair of lungs, and shows the interstitial lung space surrounding the alveoli. High pulmonary blood pressures are present in subjects with elevated intravascular filling pressures as a result of heart failure. This high pulmonary blood pressure may also lead to increased amounts of fluid entering the extravascular space. Congestion within the extra-vascular interstitial lung tissue may prevent gas exchange ultimately, leading to a difficulty breathing that may require hospitalization. Hospital therapies are typically directed at reducing the pulmonary blood pressure by removing intravascular fluid with diuretic therapy. Although subject symptoms may improve, significant extravascular interstitial fluid may still be present. Subjects may feel well enough for discharge, but only a small change in pulmonary blood pressures will cause fluid to quickly re-accumulate, requiring readmission. Thus, subject symptoms do not reflect adequate treatment for the extent of the disease. Therefore, there is a need to detect and monitor extravascular interstitial fluid (e.g., lung wetness) and to provide an index or measure of the level extravascular interstitial fluid both instantaneously, and over time.

There are several methods for assessing total body water, as the most prominent indicator of hydration status, including methods based on bioelectrical impedance and conductance. For example, U.S. Pat. No. 4,008,712 to Nyboer discloses method and apparatus for performing electrical measurement of body electrical impedances to determine changes in total body water in normal and deranged states of the body, U.S. Pat. No. 5,615,689 to Kotler discloses a method of predicting body cell mass using impedance analysis, U.S. Pat. No. 6,280,396 to Clark discloses an apparatus and method for measuring subject's total body water content by measuring the impedance of the body, and U.S. Pat. No. 6,459,930 to Takehara et al. discloses a dehydration condition judging apparatus by measuring bioelectric impedance. However, these methods and systems have proven unreliable and difficult to implement. The aqueous tissues of the body, due to their dissolved electrolytes, are the major conductors of an electrical current, whereas body fat and bone have relatively poor conductance properties. Significant technical problems have hampered many such electrical methods for in vivo body composition analyses; impedance spectroscopy is an attempt to refine bio-impedance measurements, which measures resistance and reactance over a wide range of frequencies. A technique based on this approach is described in U.S. Pat. No. 6,125,297 to Siconolfi which describes a method and apparatus for determining volumes of body fluids in a subject using bioelectrical response spectroscopy.

Although various systems for using electrical energy have been proposed and developed, many of these systems are complex and difficult and expensive to implement. For example, systems such as electrical impedance imaging/tomography (EII/EIT) and applied potential tomography have been described elsewhere. For example, a system such as the one described in US 2007/0246046 to Teschner et al. (and others owned by the Draeger corporation) uses an electrical impedance tomography (EIT) method for reconstituting impedance distributions. In such systems, a plurality of electrodes may be arranged for this purpose on the conductive surface of the body being examined, and a control unit, usually a digital signal processor, typically ensures that a pair of (preferably) adjacent electrodes are each supplied consecutively with an electric alternating current (for example, 5 mA at 50 kHz), and the electric voltages are detected at the remaining electrodes acting as measuring electrodes and are sent to the control unit. Typically, a ring-shaped, equidistant arrangement of 16 electrodes is used, and these electrodes can be placed around the body of a subject, for example, with a belt. Alternating currents may be fed into two adjacent electrodes each, and the voltages are measured between the remaining currentless electrode pairs acting as measuring electrodes and recorded by the control unit.

Other described EIT systems, such as those illustrated in U.S. Pat. No. 7,660,617, US 2010/0228143, and WO 91/019454, do not show evidence that measurements would not vary with subject habitus, e.g., body shape or geometry.

Unfortunately, electrical impedance methods have proven difficult to reliably and accurately implement for determining tissue wetness, and particularly lung wetness. Often, additional anthropometric terms (i.e., weight, age, gender, race, shoulder width, girth, waist-to-hip ratio, and body mass index) must be included in these previous prediction models to reduce the error of the estimate within acceptable boundaries. In addition, the reliability and reproducibility of the wetness estimates may vary depending on the geometry and placement of the electrodes. Thus, current methods and systems for assessing water content based on the bioimpedance of tissues may result in low accuracy, significant dependence of testing results on the anthropometrical features of the subject and on electrolyte balance.

There is therefore a need for a simple and highly accurate method and device for monitoring tissue hydration status that can be used in a broad range of field conditions.

Described herein are systems, devices and methods that may provide an objective measure of tissue wetness. In some specific variations, the systems, devices and methods may be configured to measure pulmonary congestion (e.g., extravascular interstitial fluid) in in-subject and/or out-subject settings, including home use. For example, the systems described herein may provide non-invasive, accurate, and reproducible measures of pulmonary congestion. These systems may be referred to as lung fluid assessment monitors. Any of the systems described herein may include executable logic to detect tissue wetness utilizing relative percent differences of apparent resistivities from the skin into the tissue derived from applying currents and measuring voltages in a specified geometric pattern of electrodes applied to the skin. The systems described herein may therefore be non-invasive, rapid, and do not use ionizing radiation.

Some variations of the systems described herein may be referred to as lung fluid assessment monitors, and may have executable logic configured to detect extravascular interstitial lung fluid utilizing determining relative spatial change in subsurface resistivities across frequencies from the skin to the lung region derived from applying currents and measuring voltages in a specified geometric pattern of electrodes applied to the skin. As mentioned, these systems may also provide an objective absolute measurement of pulmonary fluid status, such as an extravascular lung water (EVLW) index. The systems, devices and methods described herein may address many of the problems identified above, and may offer reliable and effective techniques for determining tissue wetness by determining a distribution of relative percent differences of the tissue regions beneath the electrodes to derive a value or distribution of values that are independent of the subject's body geometry. The resulting information may provide a map indicating the relative percent differences of spatial distributions of resistivities within the body across multiple frequencies. Also described herein are methods of interpreting the relative percent difference map to determine tissue wetness and, in particular, to monitor changes in tissue wetness.

SUMMARY OF THE DISCLOSURE

Described herein are non-invasive devices, systems and methods to determine tissue wetness. In general, the devices, methods and systems described herein determine the relative spatial change in subsurface resistivities across frequencies which are geometry independent and may be used to determine water content and/or tissue wetness for a region of tissue below a sensor having an array of current-injecting and voltage sensing electrodes.

In general, a relative spatial change in subsurface resistivities across frequencies refers to the relative change in resistivities between one or more frequencies for a designated spatial region below the surface on to which a sensor is placed. In the embodiments described herein, this may refer to the resistivity change in the region below a patch (of electrodes) relative to one or more measurements taken at different frequencies.

In general, the relative spatial change in subsurface resistivities across frequencies (which may also be referred to by the acronym RSCSRAF) refers to the relative spatial change in the region below (the subsurface region) the sensor, which may also be referred to as a patch or electrode patch. Thus, the relative spatial change refers to the change in resistivities for subsurface regions which are located beneath the sensor at various depths (z) and lengths (x). The subsurface resistivities have spatial locations within the mesh elements of the subsurface (i.e. in a finite difference or finite element analysis or analytic). As described in greater detail below, the subsurface resistivities for a region under a sensor may be determined as a set of unknown resistivity variables contained within a forward problem by which each subsurface resistivity variable can be solved at each frequency at which measurements are taken, using an iterative method by minimizing the error between measured values of the system and corresponding outputs of the forward problem. This technique is called an inverse problem. Each subsurface resistivity variable determined at a given frequency can be compared against its value determined at another frequency in a relative manner in which one value is divided by the other. Examples of relative spatial change values include ratios between two values or taking a relative percent difference between the two values, at high and low frequency values, i.e.

$$\frac{\rho_H}{\rho_L}, 100*\frac{\rho_H}{\rho_L}, 100*\frac{\rho_L-\rho_H}{\rho_L},$$

or $100\ (\rho_L-\rho_H)/\rho_H$. Thus, one example of relative spatial change in subsurface resistivities across frequencies the relative percent difference (RPD) in resistivity, e.g., at a low and high frequency. As described in detail below, the relative spatial change in subsurface resistivities across frequencies can surprisingly and robustly indicate the water content (e.g., hydration) of a tissue, and may be used to determine, track, or otherwise monitor hydration status. In some variations, an index of hydration may be determined from the relative spatial change in subsurface resistivities across frequencies.

For example, a relative spatial change in subsurface resistivities across frequencies may be estimated as a relative percent difference in resistivity at a high and low frequency. In some variations, the relative percent difference of resistivity between a low and high frequency is determined for each region in the spatial distribution by multiple applied currents and measured voltages and using mathematical inversion methods to construct a spatial image of the relative percent differences in resistivity within the subsurface spatial distribution. An electrode array can be configured to consist of typically four electrodes where two electrodes are used for measuring electric current and two electrodes are used to measure differential voltage. The sensor, applied to the subject, contains numerous fixed spaced electrodes of which thousands of electrode arrays can be configured. The sensor may be referred to as a patch.

The sensor described herein may be sized and configured to allow reliable detection of RSCSRAF for subsurface regions beneath the sensor. For example, the system may be configured to provide reliable detection of RSCSRAF as deep as three inches (e.g., 2" to 2.5") beneath the sensor.

Part I of this disclosure describes methods, devices and systems for determining tissue wetness. In general, the devices, methods and systems described herein may be used to determine RSCSRAF of a region within a body. In some variations, a map of the RSCSRAF in regions within the body may be created; this map may be displayed, or used internally and not displayed. Thus, in some variations the RSCSRAF may be used without producing an image. For example, the values may be stored as a vector or matrix of values that may be used to determine a physiological parameter, such as lung wetness. In one variation, these values may be used to determine one or more hydration index(es), ranking or output using the non-invasive technology described herein.

In general, the system uses an applied sensor consisting of multiple electrodes of which it can be configured to apply a series of electrical currents between drive (e.g. current-injecting) electrodes of multiple frequencies and measures the voltage between selected pair of electrodes. The RSCSRAF may be used by physicians to improve the medical management of subjects, including heart failure subjects, by enabling appropriate and timely interventions that reduce unnecessary hospitalizations and slows disease progression amongst a growing population of chronic heart failure subjects throughout the world.

Any of the systems, devices and methods described herein may be configured to determine a relative spatial change in subsurface resistivities across frequencies, and the resulting spatial distribution of relative changes in subsurface resistivities (relative the different frequencies examined) may be used to determine characteristics of tissue in the spatial region examined, which corresponds to the region of tissue beneath the sensor. For example, any of the systems/devices and methods described herein may be used to determine tissue water content.

Thus, described herein are methods of determining water content of a subject's tissue using a sensor comprising a plurality of electrodes that is placed on the subject, the method including: applying currents between a first pair of electrodes on the sensor and detecting voltages from a second pair of electrodes on the sensor at a plurality of current frequencies; determining a relative spatial change in subsurface resistivities across frequencies from the applied currents and detected voltages; and presenting a representation of water content for a region of tissue beneath the sensor based on the relative spatial change in subsurface resistivities.

Determining the relative spatial change in subsurface resistivities across frequencies may include determining a distribution of relative percent difference (RPD) in resistivities between the first frequency and the second frequency. As mentioned above, the relative percent difference in resistivities is one way to represent a relative change in subsurface resistivities across frequencies (e.g., $100\ (\rho_L-\rho_H)/\rho_H$).

Determining the relative spatial change in subsurface resistivities across frequencies may comprise estimating a spatial distribution of sub-surface resistivities for a region of tissue beneath the sensor based on the applied currents and detected voltages using an inverse problem to solve for the spatial distribution of subsurface resistivities by minimizing the error between detected values and those produced by a forward model calculating a change in subsurface resistivities.

Applying current between a first pair of electrodes and detecting voltages from a second pair of electrodes at a plurality of current frequencies may include applying current between a first pair of electrodes and detecting voltages from a second pair of electrodes at any appropriate frequencies, including a high frequency and a low frequency. In some variations, more than two frequencies may be examined. In other variations, only two frequencies are used. For example, current may be applied at a low frequency of less than about 100 kHz at a high frequency of greater than about 100 kHz. In some variations, currents may be applied at a low frequency of about 50 kHz or less and at a high frequency of about 200 kHz or more.

Any appropriate representation of water content may be presented. Appropriate representations may include visual, written, aural, pictorial, and/or alphanumeric, including indices that represent water content. For example, presenting a representation of water content may include generating an image representing the relative spatial change in subsurface resistivities for a region of tissue beneath the sensor. Presenting a representation of water content may include presenting an index representing water content for the region of tissue beneath the sensor.

In general, a sensor may be placed anywhere on a subject for which water content is to be measured. Thus, placing a sensor typically comprises placing a plurality of electrodes on a subject. Examples of sensors are provided herein. In some variations the sensor may be configured to conform to the region of the body onto which it is placed, so that the sensor does not have to change the relative positions of the electrodes while still contacting the subject's skin.

Any of the steps described herein may be performed by a computer or machine including a processor, and thus may be performed by the processor or processors, including general-purpose or customized processors. The methods may be encoded in logic (hardware, software or firmware) that controls and specifically configured the device/computer to perform these steps. For example, the relative spatial change in subsurface resistivities may be determined using a processor unit coupled to a plurality of electrodes.

In another example described herein of methods of determining water content of a subject's tissue using a sensor comprising a plurality of electrodes that is placed on the subject, the method may include: placing the sensor on the subjects skin against a region of tissue, wherein the sensor comprises a plurality of current-injecting electrode pair combinations and a plurality of voltage detection electrode pairs arranged across a subject-contacting surface of the sensor; independently applying current between at least some of the current-injecting electrode pairs while detecting voltages from at least some of the voltage detection electrode pairs, wherein currents are applied at a plurality of current frequencies to each current-injecting electrode pair; determining a relative spatial change in subsurface resistivities across frequencies from the applied currents and detected voltages; and presenting a representation of water content for a region of tissue beneath the sensor based on the relative spatial change in subsurface resistivities.

Another example of a method of determining water content of a subject's tissue using a sensor comprising a plurality of electrodes placed on the subject includes: placing the sensor on the subjects skin against a region of tissue, wherein the sensor comprises a plurality of four point electrode array combinations comprising a pair of current-injecting electrode pairs and a pair of voltage detection electrode pairs arranged across a subject-contacting surface of the sensor; separately applying current between the current-injecting electrode pairs of at least some of the four point electrode arrays while detecting voltages from the voltage detection electrode pairs, wherein current is applied to the current-injecting electrode pairs at a plurality of current frequencies; and determining a relative spatial change in subsurface resistivities across frequencies from the applied currents and detected voltages; and presenting a representation of water content for a region of tissue beneath the sensor based on the relative spatial change in subsurface resistivities.

Separately applying current may include applying current between the current-injecting electrode pairs of at least some of the four point electrode arrays at a high frequency and a low frequency. For example, separately applying current may include applying current between the current-injecting electrode pairs of at least some of the four point electrode arrays at a low frequency of less than about 100 kHz and applying a plurality of currents at a high frequency of greater than about 100 kHz. In some variations, separately applying current comprises applying current between the current-injecting electrode pairs of at least some of the four point electrode arrays at a low frequency of about 50 kHz or less and applying a plurality of currents at a high frequency of about 200 kHz or more.

Any combination of four point electrode arrays may be selected. In some variations of four point electrode arrays, the current-injecting electrode pairs are in-line (so all four electrodes form a straight line) with the voltage detection electrodes. In some variations the current-injecting electrodes bracket or surround voltage detection electrodes. Different four point electrode arrays may share up to three electrodes in common with any other four point electrode array on the sensor. Examples of sensors including a plurality of four point electrode arrays are described herein.

A system for determining a subject's tissue hydration may include: a controller configured to control the application of currents at a plurality of different frequencies between current-injecting electrode pairs on a sensor, and to concurrently receive resulting voltage information from pairs of voltage detection electrodes on the sensor; a processing unit in communication with the controller wherein the processing unit is configured to determine a relative spatial change in subsurface resistivities across frequencies based on stimulation parameters of the applied currents and the resulting voltages; and an output for outputting a representation of water content for a volume of the subject's tissue from the relative spatial change in subsurface resistivities.

Any of the systems described herein (which may also be configured as devices or apparatus) are adapted for use with a sensor including a plurality of current-injecting electrodes and voltage sensing electrodes. In some variations the electrodes are included with the system, though they do not need to be; a variety of different sensors may be used. The electrodes (sensor) may be provided separately from the controller and processor. Commercially, the system may be sold separately from the sensor, and the sensor element may be disposable or re-usable, as described in greater detail below. In some variations the system includes a sensor. For example, the system may include a sensor comprising a plurality pairs of current-injecting electrodes and a plurality of pairs of voltage detection electrodes, wherein the controller controls the application of currents at a plurality of different frequencies between the current-injecting electrodes pairs. In some variations the system includes a sensor comprising a plurality of four point electrode arrays each comprising one pair of current-injecting electrodes and one pair of voltage detection electrodes wherein the controller controls the application of currents at a plurality of different frequencies between the current-injecting electrodes pairs. In some variations the system includes a sensor comprising a plurality pairs of current-injecting electrodes and a plurality of pairs of voltage detection electrodes wherein the plurality of pairs of current-injecting electrodes and a plurality of pairs of voltage detection electrodes are arranged in a line, further wherein the controller controls the application of currents at a plurality of different frequencies between the current-injecting electrodes pairs. In some variations the system includes an adhesive patch sensor having a plurality pairs of current-injecting electrodes and a plurality of pairs of voltage detection electrodes wherein the controller controls the application of currents at a plurality of different frequencies between the current-injecting electrodes pairs.

The controller generally controls the application of current to electrodes and coordinates the acquisition of sensed voltage. For example, a controller may be configured to control the application of current between the current-injecting electrode pairs at a low frequency and a high frequency; for example, a low frequency of less than about 100 kHz and a high frequency of greater than about 100 kHz, a low frequency of about 50 kHz or less and a high frequency of about 200 kHz or more, etc.

The processing unit is generally configured to determine the relative spatial change in subsurface resistivities across frequencies. For example, the processing unit may be configured to (e.g., by applying processing logic) determine a distribution of relative percent difference (RPD) in resistivities between a first applied current frequency and a second applied current frequency over a volume of the subject's tissue. A processing unit may be configured to determine the relative spatial change in subsurface resistivities across frequencies by estimating a spatial distribution of sub-surface resistivities for a region of tissue based on the applied currents and resulting voltages using an inverse problem to solve for the spatial distribution of subsurface resistivities by minimizing the error between detected values and those produced by a forward model calculating a change in subsurface resistivities.

The system may be configured to provide any appropriate output. For example, an output may be a visual output (monitor, screen, printer, display, LEDs, etc.) an aural output (speaker, alarm, etc.), an electronic output (wireless, wired, etc.), or some combination of such outputs. In general, an output may be configured to present a representation of hydration (and/or water content) for a region of tissue beneath the sensor comprising an index of hydration (e.g., index of water content).

The system may be configured to apply current and take voltages sequentially (e.g., at different frequencies and/or at different electrode combinations of current-injecting and voltage sensing electrodes) or simultaneously, or some combination or mixture of the two. For example, the controller may be configured to control the application of currents at a plurality of different frequencies between current-injecting electrode pairs on the sensor so that the application of currents at a plurality of different frequencies is applied sequentially.

Also described herein are systems for determining a subject's tissue hydration, the system may include: a sensor comprising a plurality of electrodes arranged across a subject-contacting surface of the sensor, from which a plurality of pairs of current-injecting electrodes and a plurality of pairs of voltage detection electrodes are selectable; an energy source configured to apply current between current-injecting electrode pairs at a plurality of different current frequencies; a controller configured to drive the energy source to apply current to pairs of current-injecting electrodes on the sensor and to concurrently receive resulting voltage information from pairs of voltage detection electrodes on the sensor; and a processing unit configured to determine a relative spatial change in subsurface resistivities across frequencies based on stimulation parameters of the applied currents and the resulting voltages.

As mentioned, any of the systems described herein may include (or be configured for use with) a sensor having a plurality of four point electrode arrays each comprising one pair of current-injecting electrodes and one pair of voltage detection electrodes. The plurality of pairs of current-injecting electrodes and the plurality of pairs of voltage detection electrodes may be arranged along a line. Any of the sensors described herein may be configured as an adhesive patch sensor. For example, the adhesive may be a conductive material (e.g., conducive gel) that is positioned between the skin and the electrode(s).

Any of the systems described herein may be configured to determine the relative spatial change in subsurface resistivities across frequencies by determining a distribution of relative percent difference (RPD) in resistivities between a first applied current frequency and a second applied current frequency. For example, the processing unit may be configured to determine the relative spatial change in subsurface resistivities across frequencies by estimating a spatial distribution of sub-surface resistivities for a region of tissue based on the applied currents and detected voltages using an inverse problem to solve for the spatial distribution of subsurface resistivities by minimizing the error between detected values and those produced by a forward model calculating a change in subsurface resistivities.

Another example of a system for determining a subject's tissue hydration includes: a sensor comprising a plurality of four point electrode arrays, each four point electrode array having a pair of current-injecting electrodes and a pair of voltage detection electrodes, wherein the electrodes of the four point electrode arrays are arranged across a subject-contacting surface of the sensor in a fixed relation; an energy source configured to apply current between current-injecting electrode pairs of each of the four point electrode arrays at a plurality of different current frequencies; a controller configured to control the energy source to apply current sequentially to pairs of current-injecting electrodes of at least a plurality of the four point electrode arrays, and to concurrently receive resulting voltage information from the voltage detection electrodes; a processing unit in communication with the controller that is configured to determine a relative spatial change in subsurface resistivities across frequencies based at least in part on stimulation parameters of the applied currents and the resulting voltages; and an output configured to present a representation of water content for a region of tissue beneath the sensor based on the relative spatial change in subsurface resistivities.

Any of the devices, methods and systems described herein may be configured to detect and/or monitor lung wetness. For example, described herein are systems, including sensors for determining, detecting, monitoring, tracking, and/or treating lung wetness. In particular, described herein are implementations of the system and sensor specifically adapted for lung wetness applications.

For example, described herein are methods of non-invasively determining lung wetness including the steps of: placing a sensor comprising a plurality of electrodes arranged in a proximal to distal active region on the subject's back so that the proximal to distal axis of the sensor extends cranially to caudally along the subject's back, and wherein the active region of the sensor is positioned lateral to the subject's spine; using the sensor to determine a relative spatial change in subsurface resistivities across frequencies based on applied currents and detected voltages.

Any of these methods may include conforming the sensor the subject's skin as it extends along the length of the back. Placing the sensor may include positioning the active region of the sensor offset from the midline of the subject's back lateral to the spine. For example, placing the sensor may comprise placing the active region of the sensor offset from the midline of the subject's back lateral to the subject's spine by approximately an inch. In some variations, placing includes placing the active region of the sensor along the subject's back from a region in line with the top of the subject's scapula and extending caudally for approximately 8 or more inches. In some variations, placing comprises placing the center of the active region of the sensor along the subject's back from a region in line with the subject's lung. In addition (or alternatively), placing may include positioning a lateral edge of the active region of the sensor offset by approximately an inch from the midline of the subject's back. For example, placing may include placing the sensor so that the active region of the sensor extends laterally from about an inch from the midline of the subject's back to about 3 inches from the midline of the subject's back. In some variations, each electrode of the active region extends laterally from about an inch from the midline of the subject's back to about 3 inches from the midline of the subject's back.

Any appropriate sensor may be used. Appropriate sensors include those that may be placed along the subject's back while maintaining the relative positions of the electrodes and good skin contact with the subject's back. For example, a sensor may include a plurality of elongate electrodes arranged in parallel and oriented transverse to the proximal to distal axis of the sensor to form the active region. Placing may include placing the proximal portion of the active region of the sensor approximately in line with the top of the subject's scapula. In some variations, placing comprises placing a middle portion of the sensor approximately in line with the subject's lung.

In general, the relative spatial change in subsurface resistivities across frequencies may be determined using an inverse problem to solve for the spatial distribution of subsurface resistivities by minimizing the error between detected values and those produced by a forward model calculating a change in subsurface resistivities.

Applying may include applying a plurality of currents between pairs of at least some of the electrodes, wherein current is applied to pairs of electrodes while detecting voltage with other pairs of electrodes, further wherein a plurality of current frequencies are applied.

The step of using the sensor to determine a relative spatial change in subsurface resistivities across frequencies may include determining a spatial distribution of relative percent differences of apparent resistivities at a high and a low frequency.

Any of these methods may include presenting a representation of lung wetness based on the relative spatial change in subsurface resistivities across frequencies.

In some variations the method may include determining an index of lung wetness, or some other indicator of lung wetness. For example, the method may include determining a slope of the relative spatial change in subsurface resistivities across frequencies extending from a more superficial region of the subject's body to a deeper region of the subject's body and providing an output indicating that the lung is dry based on the slope. In general, the methods may include a step of providing an output indicating that the lung is dry when the slope is above a predetermined value.

Also described herein are methods of non-invasively determining lung wetness, the method comprising: applying currents at a plurality of frequencies from a sensor on a region of a subject's back; determining a spatial distribution of relative spatial change in subsurface resistivities across frequencies across the region of the subject's back; determining a slope of the spatial distribution of the relative spatial change in subsurface resistivities across frequencies from the spatial distribution across the region of the subject's back extending from more superficial regions to deeper regions; and indicating that the lung is dry based on the slope.

In general, the step of indicating may include indicating that the lung is dry when the slope is above a threshold. For example, indicating may comprise indicating that the lung is dry when the slope is positive. The method may include comparing an average of at least some of the values from the relative spatial change in subsurface resistivities across frequencies to a threshold value, and indicating that the lung is dry or wet based on the slope. Comparing an average may include comparing an average of values from the relative spatial change in subsurface resistivities across frequencies (RSCSRAF) from a central subsurface region beneath the sensor to the threshold value.

Determining a spatial distribution of relative spatial change in subsurface resistivities across frequencies may comprise determining a spatial distribution of relative percent differences in resistivities. For example, determining the spatial distribution of the relative spatial change in subsurface resistivities across frequencies may include determining the spatial distribution of relative percent differences between apparent resistivities at a high frequency and a low frequency from a region of a subject's back between the scapula and spine.

As mentioned above, any of these methods may include placing the sensor on the subject's back so that an active region of the sensor comprising electrodes extends cranially to caudally along the subject's back, lateral to the subject's spine.

Also described herein are methods of non-invasively determining lung wetness comprising: applying currents at a plurality of frequencies from a sensor on a region of a subject's back; determining a spatial distribution of relative spatial change in subsurface resistivities across frequencies across the region of the subject's back; and comparing an average of at least some of the values from the relative spatial change in subsurface resistivities across frequencies to a threshold value, and indicating that the lung is dry or wet based on this comparison. Comparing an average may comprise comparing an average of values from the relative spatial change in subsurface resistivities across frequencies (RSCSRAF) from a central subsurface region beneath the sensor to the threshold value. In some variations, comparing comprises indicating that the lung is dry or wet based on the comparison and based on a depth of a peak relative spatial change in subsurface resistivities across frequencies.

Also described herein are methods of non-invasively determining lung wetness including: applying currents at a plurality of frequencies from a sensor on a region of a subject's back; determining a spatial distribution of relative spatial change in subsurface resistivities across frequencies across the region of the subject's back; determining a slope of the spatial distribution of relative spatial change in subsurface resistivities across frequencies from the spatial distribution across the region of the subject's back extending from more superficial regions to deeper regions; indicating that the lung is dry when the slope is positive; and comparing an average of at least some of the values from the relative spatial change in subsurface resistivities across frequencies to a threshold value, and indicating that the lung is dry or wet based on this comparison and based on the slope. For example, comparing an average may comprise comparing an average of values from the relative spatial change in subsurface resistivities across frequencies (RSCSRAF) from a central subsurface region beneath the sensor to the threshold value.

Also described herein are methods of non-invasively determining lung wetness, the method comprising: applying currents at a plurality of frequencies from a sensor on a region of a subject's back; determining a spatial distribution of relative spatial change in subsurface resistivities across frequencies across the region of the subject's back; and comparing an average of values for the relative spatial change in subsurface resistivities across frequencies from a central subsurface region beneath the sensor to a threshold value, and indicating that the lung is dry or wet based on this comparison and based on a depth of a peak relative spatial change in subsurface resistivities across frequencies.

The methods described include methods of non-invasively determining lung wetness within a subject's body, the method comprising: placing a sensor comprising a plurality of electrodes from which pairs of current-injecting electrodes and pairs of voltage detection electrodes are selectable; applying currents between at least some of the pairs of current-injecting electrodes at a plurality of different frequencies while detecting voltages from pairs of voltage detection electrodes; and processing the applied currents and voltages to at the first and second frequencies to determine a relative spatial change in subsurface resistivities across frequencies.

Another method of non-invasively determining lung wetness within a subject's body includes: placing a sensor comprising a plurality of electrodes that are arranged in a line on the subject's back, so that the plurality of electrodes extend cranially to caudally along the subject's back offset from the midline of the subject's back lateral to the subject's spine, wherein the electrodes are configured to form a plurality of four-point electrode array combinations, each comprising a pair of current-injecting electrodes and voltage detection electrodes; applying a first frequency current between pairs of current-injecting electrodes of different four point electrode arrays while detecting voltages from the pair of voltage detection electrodes in each array; applying a second frequency current between pairs of current-injecting electrodes of different four point electrode arrays while detecting voltages from the pair of voltage detection electrodes in each array; and processing the applied currents and voltages at the first and second frequencies to determine a relative spatial change in subsurface resistivities across frequencies (RSCSRAF); and presenting a representation of lung wetness based on the relative spatial change in subsurface resistivities across frequencies.

Any of the systems, devices and apparatus described herein may also be configured to determine lung wetness. For example, described herein are systems for determining lung wetness including: a controller configured to control the application of currents at a plurality of different frequencies between current-injecting electrode pairs on a sensor, and to receive resulting voltage information from pairs of voltage detection electrodes on the sensor; a processing unit in communication with the controller that is configured to determine a relative spatial change in subsurface resistivities across frequencies based at least in part on parameters of the applied currents and the resulting voltages; and an output for outputting a representation of lung wetness from the relative spatial change in subsurface resistivities.

As with any of the systems and devices described herein, the systems may include a sensor or may not include a sensor but be configured for operation with a sensor. For example, a system may include a sensor comprising a plurality pairs of current-injecting electrodes and a plurality of pairs of voltage detection electrodes. In some variations, the sensor includes a plurality of four point electrode arrays each comprising one pair of current-injecting electrodes and one pair of voltage detection electrodes. The system may include a sensor comprising a plurality pairs of current-injecting electrodes and a plurality of pairs of voltage detection electrodes wherein the plurality of pairs of current-injecting electrodes and a plurality of pairs of voltage detection electrodes are arranged in a line along a tissue-contacting surface of the sensor. As mentioned above, the sensor may be configured as an adhesive patch sensor having a plurality pairs of current-injecting electrodes and a plurality of pairs of voltage detection electrodes.

In any of these systems/devices, the controller may control the application of current and the receipt of voltage to/from the subject's tissue. For example, a controller may be configured to control the application of current between the current-injecting electrode pairs at a low frequency and a high frequency, for example: a low frequency of less than about 100 kHz and a high frequency of greater than about 100 kH; a low frequency of about 50 kHz or less and a high frequency of about 200 kHz or more, etc.

The processing unit may be configured to determine the relative spatial change in subsurface resistivities across frequencies by determining a distribution of relative percent difference (RPD) in resistivities between a first applied current frequency and a second applied current frequency over a volume of the subject's tissue. The processing unit may be configured to determine the relative spatial change in subsurface resistivities across frequencies by estimating a spatial distribution of sub-surface resistivities for a region of tissue based on the applied currents and resulting voltages using an inverse problem to solve for the spatial distribution of sub-surface resistivities by minimizing the error between detected values and those produced by a forward model calculating a change in subsurface resistivities. In some variations, the processor is configured to determine an index of lung wetness from the relative spatial change in subsurface resistivities across frequencies, and further wherein the output is configured to output the index of lung wetness as the representation of lung wetness.

Another example of a system for non-invasively determining lung wetness may include: a controller configured to control the application of currents at a plurality of different frequencies to pairs of current-injecting electrodes on a sensor and to concurrently receive resulting voltage information from pairs of voltage detection electrodes on the sensor; a processing unit configured to process information about the applied current and resulting voltage and to calculate apparent resistivities at different frequencies, and to determine relative percent differences of the apparent resistivities determined across different frequencies; and an output configured to present a representation of lung wetness based on the relative percent differences of the apparent resistivities determined across different frequencies. As mentioned, the controller may be configured to control the sequential application of currents at a plurality of different frequencies.

As used herein, "apparent resistivities" may include those resistivities taken or estimated at the surface of the tissue. Subsurface resistivities are typically those estimated for regions within the tissue. Generally, the resistivities referred to herein are subsurface resistivities unless the context indicates otherwise.

In variations including a sensor, the sensor may include a plurality of elongate electrodes arranged in parallel and transverse to a proximal to distal axis of the sensor, wherein the electrodes comprise a plurality of voltage-sensing voltage detection electrodes and a plurality of current-applying current-injecting electrodes.

In variations including an output, the system output may be configured to provide an index of lung wetness. In some variations, the output is configured to provide a map of spatial resistivities, a map of the relative percent differences representing the region of the subject tissue beneath the electrode array, or both.

The processor may be configured to determine a slope of the spatial distribution of relative percent differences of the apparent resistivities; further wherein the output is configured to indicate that the lung is dry based on the slope. For example, the system may be configured to indicate that the lung is dry when the slope is above a threshold. The system may be configured to indicate that the lung is dry when the slope is positive.

As mentioned above, sensors for determining tissue hydration/wetness are also described. In particular, sensors for determining lung wetness are described. These sensors may be used with systems other than those explicitly described herein, though they are particularly useful for the systems/devices and methods described herein.

The configuration of the sensor may generally include a sufficient number of appropriately dimensioned (e.g., sized) stimulation/detection electrodes in a predetermined arrangement. In some variations, the sensor (and particularly a lung wetness sensor variations of the sensors generally described herein) is configured to extend cranially to caudally along an off-midline region of the subject's back while maintaining good contact along the entire region. For example, the sensor may include: a flexible support backing extending along a proximal to distal axis; a plurality of elongate electrodes arranged in parallel and transverse to the proximal to distal axis of the support backing to form an active region, wherein the active region extends between about 8 and about 14 inches along the proximal to distal axis; further wherein each of the electrodes is between about 1.5 and about 2.5 inches long and between about 0.1 and about 0.5 inches wide. This configuration may be an optimized variation for the determination of lung wetness.

From a sensor consisting of tens of electrodes, thousands of tetrapolar arrays, consisting of two current electrodes and two voltage measurement electrodes, are possible. The device is connected to the sensor from which it can select tetrapolar arrays that are advantageous in determining lung wetness. A device may use programmable logic connected to the sensor from which it can select tetrapolar array configurations and the frequency of the measurement. The tetrapolar arrays may be used by the device to determine the RSCSRAF in soft tissue. Many of the systems, devices and methods described herein are configured so that the sensor is applied to a region of the back that is just off the midline of the back, which may be particularly helpful for determining lung wetness. In some variations the sensor (or a variation of the sensor) may be applied to other body regions. For example, in some variations the sensor may be applied along the midaxillary line (e.g., a coronal line on the torso between the anterior axillary line and the posterior axillary line; the line may extend caudally from the subject's armpit). In applying the sensor, the sensor may be applied so that the tip of the sensor is as far in the subject's armpit as possible while maintaining good electrical contact. The electrodes may extend down the side of the body. In some variations, the same sensor configured as described herein for use down the off-midline region of the back may be used in midaxillary placement; in some variations a modified version of the sensor (e.g., having fewer electrodes and/or electrodes of different dimensions) may be used. The spacing of the electrodes may or may not be equally spaced. Other than the midaxillary placement, the system and method may otherwise be the same, such as determining the distribution of the RSCSRAF.

The sensor may be configured so that it extends down the subjects back without losing contact (e.g., without wrinkling, bending, buckling, or otherwise losing contact). Loss of contact over all or a portion of the sensor (and particularly the active region containing the electrodes) may result in inaccuracies in the measurements which, while they may be compensated by the other aspects of the system such as the circuitry and analysis logic, could increase the time required for the analysis or the decease the accuracy. Thus, in general, the sensor may be flexible, thin and have a small overall area yet still be large enough to take reasonable measurements. Towards this goal, the sensor may have a width that is less than 2.5 inches. In some variations, the active region extends substantially across the entire width of the flexible support backing, limiting the excess support backing region (particularly laterally from the width) which may otherwise lead to buckling or a loss of width. The support backing may comprise a polyester material and an anti-bacterial titanium oxide material (e.g., coating, etc.). Further, in some variations the sensor is conformable to the contour of a subject's back and has a thickness of less than about 5 mils.

In general, the sensor active region may include about 20 or more electrodes, about 25 or more electrodes, about 31 or more electrodes, or the like. The current-injecting electrodes may each be configured as current emitting electrodes and may be connected to a dedicated current-injecting lead for the application of current. The sensing electrodes may be configured for sensing voltage, and may each be connected to a dedicated sensing lead for sensing voltage. The leads are typically insulated connections between the surface of the electrodes applying current and/or sensing voltage and the rest of the system, including the processors and the like. In some variations the sensing electrodes and the current-injecting electrodes alternate, with the first and last electrodes in the sensor (at the proximal and distal ends, respectively) current-injecting electrodes. In some variation any electrode can be either a current drive electrode, voltage sense electrode, or both a current drive electrode and voltage sense electrode.

In some variations the sensor further comprises a proximal grip region extending proximally of the active region and a distal grip region extending distally of the active region. This grip region may be particularly useful when the electrodes extend laterally (transverse to the proximal/distal axis) across the entire width of the sensor.

In some variations the sensor further comprises a graphic print layer that may indicate how to align to anatomical landmarks.

Any appropriate conductive material may be used to form the electrodes, including silver/silver chloride. In some variations the sensor includes a conductive gel on the electrodes (or is compatible with a conductive gel). In some variations the conductive gel may include an adhesive. For example, some variations, the sensor is non-adhesive and the gel adheres it to the subject.

Any of the sensors described herein may be disposable (including single-use) or reusable. The sensors may be provided sealed and with pre-applied conductive gel. Other variations of sensor designs are described and illustrated below.

For example, described herein are non-invasive lung wetness sensors including: a support backing extending along a proximal to distal axis; a plurality of elongate electrodes each having a length of between about 1.5 and about 2.5 inches and a width of between about 0.1 and about 0.5 inches, wherein the electrodes are arranged with their lengths perpendicular to the proximal to distal axis on a subject-contacting surface of the support backing so that the electrodes extend in a line parallel to the proximal to distal axis of the support backing to form an active region that extends between about 6 and about 14 inches along the proximal to distal axis; and wherein the plurality of electrodes in the active region are configured to form a plurality of pairs of current-injecting electrodes and a plurality of pairs of voltage detection electrodes.

The support backing may be flexible and relatively inelastic, so that the spacing between each of the electrodes remains relatively fixed as the sensor is manipulated. In some variations, the support backing is less than about 5 mils thick. For example, the support backing may comprise a polyester material. The width of the support backing may be less than 2.5 inches. The support backing may comprise a polyester material and an anti-bacterial titanium oxide material.

In some variations the sensor includes an adhesive hydrogel. The adhesive may be included in the hydrogel, which may be conductive.

Any appropriate number of electrodes (e.g., >5) may be used. For example, the plurality of electrodes forming the sensor may comprise more than 6 electrodes, more than 10 electrodes, more than 25 electrodes, etc.

In some variations, the electrodes have a rectangular shape on the support backing. The sensor may also include a plurality of leads extending only from one side of the support backing. A proximal grip region may extend proximally of the active region and a distal grip region may extend distally of the active region of the sensor. The active region may extend substantially across the entire width of the flexible support backing. In some variations, the electrodes comprise silver/silver chloride electrodes. In some variations, the sensor has a thickness of less than about 5 mils. The electrodes may be separated by a fixed distance of between about 0.2 and about 0.5 inches on center down the proximal to distal length of the active region. The current-injecting electrodes and voltage detection electrodes may alternate along the proximal to distal length of the active region. In some variations, any electrode can be both a current-injecting electrode and a voltage detection electrode.

Another example of a non-invasive lung wetness sensors includes: a flexible and inelastic support backing extending in a proximal to distal axis; a plurality of six or more elongate electrodes, each having a length of between about 1.5 and about 2.5 inches and a width of between about 0.1 and about 0.5 inches, wherein the electrodes are arranged with their lengths perpendicular to the proximal to distal axis on a subject-contacting surface of the support backing so that the electrodes extend in a line parallel to the proximal to distal axis of the support backing to form an active region that extends between about 6 and about 14 inches along the proximal to distal axis; and an adhesive, conductive hydrogel on the subject-contacting surface that is configured to secure the sensor to a subject's back. The hydrogel may extend completely over the subject-contacting surface of the sensor; thus in some variations, the sensor does not include an additional adhesive gasket.

As mentioned above, the support backing may be sufficiently flexible and inelastic so that the spacing between each of the electrodes remains relatively fixed as the sensor is placed under tension of less than about two pounds of force; the support backing may be less than about 5 mils thick; the support backing may comprise a polyester material; the width of the support backing may be less than 2.5 inches; the support backing may comprise an anti-bacterial titanium oxide material.

Another variation of a non-invasive lung wetness sensor includes: a flexible and inelastic support backing of less than about 5 mils thickness extending in a proximal to distal axis; a plurality of six or more elongate electrodes, each having a length of between about 1.5 and about 2.5 inches and a width of between about 0.1 and about 0.5 inches, wherein the electrodes are arranged with their lengths perpendicular to the proximal to distal axis on a subject-contacting surface of the support backing so that the electrodes extend in a line parallel to the proximal to distal axis of the support backing to form an active region that extends between about 6 and about 14 inches along the proximal to distal axis; an adhesive, conductive hydrogel extending completely over the active region on the subject-contacting surface that is configured to secure the sensor to a subject's back; an anti-bacterial titanium oxide coating over at least a portion of the support backing; and a plurality of leads, wherein each electrode is connected with a lead extending from a first side of the support backing.

Also described herein are methods and systems for the use of the optimized tetrapolar arrays and device, including the optimized placement of the sensor along an off-midline in a cranial to caudal axis along the subject's back.

For example, in general a sensor with voltage sensing/current-injecting electrodes is applied to a specific region of a subject's body and the patch configuration described above and may be optimized for use in this body region. The sensor may also include, for example, instructions, diagrams or other indicators instructing, illustrating or confirming proper placement of the sensor on the subject's body. The proper placement of electrodes on the subject's body, for example, typically includes the placement down the cranial-to-caudal axis of the subject's back, just off of the midline of the subject's back (e.g., to the right or left of the subject's spine). This configuration may allow penetration of the electrical signal within the body to a depth sufficient to reach the subject's lung region between the spine and scapula.

For example, described herein are methods of applying a sensor to non-invasively determine lung wetness by determining within a subject's body. In general, the sensor may be any plurality of electrodes described herein, including comprising of elongated electrodes arranged in parallel and transverse to a proximal to distal axis of the patch to form an active region. The method may include the steps of: placing the sensor on the subject's back so that the proximal to distal axis of the sensor extends cranially to caudally along the subject's back, and wherein the active region of the sensor is positioned offset from the midline of the subject's back lateral to the subject's spine, further wherein the middle portion of the sensor is approximately in line with the lung; applying a plurality of currents from at least some of the electrodes at a plurality of frequencies and detecting voltages from at least some of the electrodes in the array; and calculating the RSC-SRAF based on the applied currents, detected voltages, forward modeling and solving inverse problems.

Also described herein is the analysis of relative spatial change in subsurface resistivities across frequencies (RSCS-RAF) data collected by applying a relative technique to normalize, allowing for accurate and reliable interpretation of the RSCSRAF, including methods and systems for difference techniques to determine lung wetness as mentioned above.

Also described herein is the use of various methods to interpret the RSCSRAF to accurately diagnose, monitor, treat, track, or otherwise identify lung wetness in one or more subjects. In particular, the methods described herein (as well as system specifically adapted to preform them or enable their performance) include methods of determining if a subject is experiencing lung wetness, even in the absence of other clinical manifestations.

In general, the systems and methods described herein may implement one, or more than one, process or tests for determining lung wetness from the normalized RSCSRAF. In some variations, the methods and systems may apply sequential processes or tests to determine lung wetness.

For example, described herein are methods of non-invasively determining lung wetness by determining a distribution of the RSCSRAF within a subject's body. In some variations this method includes: determining a spatial distribution of relative percent differences in resistivities at a high frequency and a low frequency; determining the slope of the relative percent differences from the spatial distribution extending from a more superficial region of the body to a deeper region of the body; and providing an output indicating that the lung is dry when the slope is positive.

In general, the step of determining the RSCSRAF may comprise determining the spatial subsurface resistivity at a high frequency and a low frequency from a region of a subject's back between the scapula and spine. For example, the method may include placing a sensor comprising a plurality of electrodes arranged in an active region of the patch on the subject's back so that the active region extends cranially to caudally along the subject's back offset from the midline of the subject's back lateral to the subject's spine. The method may also generally include applying a plurality of currents from a plurality of electrodes at a high frequency and a low frequency, and detecting voltages from at least some of the electrodes in the array for the high frequency and for the low frequency. These voltages may be used to determine the RSCSRAF from the low and high frequencies for a region of the subject beneath the sensor (e.g., through the back and into the lung). Thus, the method may include the step of calculating the RSCSRAF based on applied currents and detected voltages for a high frequency and a low frequency.

The method may also include the step of comparing an average from a region of the RSCSRAF to a threshold value and the slope being negative provides an output indicating that the lung is dry or wet. In any of the variations described herein the sum of the RSCSRAF may be used in place of the average.

The method may also include the step of comparing an average from the region of the RSCSRAF to a threshold value. In any of the variations described herein the sum of the RSCSRAF may be used in place of the average.

In general, any of the steps performed by these methods may be performed by a processor of a system for determining lung wetness. The processors described herein may include logic (software, hardware, firmware, etc.) for performing any of the steps, methods, and calculations described herein. For example, any of the systems descried herein may include a processor configured to receive electrical information (e.g., voltage, current, etc.) from the sensor (e.g., the applied electrodes) and determine a distribution of the RSCSRAF. The processor (or another processor) may also be configured to apply logic to determine a distribution of geometry-independent derived values from the RSCSRAF (e.g., relative percent differences, phase angle, etc.). The system may also include logic (e.g., modules, programs, etc.) configured to determine tissue (e.g., lung) wetness based on the derived values.

In another variation of a method of non-invasively determining lung wetness by determining a distribution of the RSCSRAF within a subject's body, the method includes the steps of: determining a spatial distribution of the RSCSRAF at a high frequency and a low frequency; determining an average of the RSCSRAF from a region of the spatial distribution; comparing the average to a threshold value; and providing an output indicating that the lung is dry or wet based on the comparison between the average RSCSRAF and the threshold. The step of determining the average may include determining an average from a central region of the spatial distribution of the RSCSRAF. Comparing the average to a threshold value may include comparing the average to an empirically determined threshold value; in some variations the threshold value is about 15.

The method may also include the step of determining the slope of the RSCSRAF from the spatial distribution over a region extending from a shallower portion of the body (e.g., skin, muscle, etc.) to a deeper region of the body (e.g., lung); and providing an output indicating that the lung is dry when the slope is positive.

As mentioned above, the step of determining the spatial distribution may comprise determining the distribution of the relative spatial change in subsurface resistivities between a high frequency and a low frequency from a region of a subject's back between the scapula and spine. For example, the method may include the step of placing a sensor comprising an array of electrodes arranged in an active region of the sensor on the subject's back so that the active region extends cranially to caudally along the subject's back offset from the midline of the subject's back lateral to the subject's spine. The method may also include applying a plurality of currents from a plurality of electrodes at a high frequency and a low frequency, and detecting voltages from at least some of the electrodes on the sensor. Resistivities may be calculated based on applied currents and detected voltages for a high frequency and a low frequency.

Also described herein are systems for non-invasively determining lung wetness by determining a distribution of the RSCSRAF within a subject's body. In some variations, the system comprises: a sensor with a plurality of elongate electrodes arranged in parallel and transverse to a proximal to distal axis of the sensor to form an active region, the sensor comprising a plurality of voltage sensing electrodes and a plurality of current-applying drive electrodes; a controller configured to apply a plurality of currents from at least some of the drive electrodes on the sensor at a plurality of frequencies; a processor configured to receive voltage information from the numerous electrodes and to calculate apparent resistivities based on the applied currents; wherein the controller is further configured to determine the RSCSRAF from a high frequency and a low frequency. In some variations, the system also includes an output configured to provide an indicator of lung wetness extracted from the RSCSRAF. For example, the system may include an output configured to provide a map of the spatial RSCSRAF and/or the relative percent differences representing the region of the subject tissue beneath the sensor.

Also described herein are methods, devices and systems for selecting which tetrapolar arrays within the sensor are to be used to determine tissue wetness/hydration, including lung wetness. When a tetrapolar array is used to measure apparent resistivity it is referred to as an electrical resistivity array. Different electrical resistivity arrays may provide better signals for determining tissue wetness, and the quality and sensitivity of the estimates for tissue wetness may be enhanced by using a subset of all possible arrays. In addition, not every possible electrical resistivity array need be used to determine tissue wetness.

For example, described herein are methods of determining which subset of electrical resistivity arrays from a plurality of electrodes in a sensor to use to determine a relative spatial change in subsurface resistivities across frequencies. The method may include: placing the sensor on a subject so that at least some of the electrodes are in contact with the subject's skin; scoring (e.g., ranking, rating, etc.) a plurality of electrical resistivity arrays, wherein each electrical resistivity array comprises a pair of current-injecting electrodes and a pair of voltage detection electrodes; applying current and recording voltages from a subject using only those electrical resistivity arrays meeting a selection criterion based upon their scores.

In general, scoring may comprise determining a score for an electrical resistivity array by estimating signal error for the electrodes in the electrical resistivity array and estimating a depth of investigation for the electrical resistivity array. For example, scoring may comprise determining a score for an electrical resistivity array by estimating one or more of signal error and depth of investigation for the electrical resistivity array. Scoring may comprise determining a score for one or more of error due to placement, voltage error, and current error, and depth of investigation for the electrical resistivity array. In some variations, scoring comprises combining two or more estimations to form a score for the electrical resistivity array, wherein the estimations are selected from the group consisting of: error due to placement, voltage error, and current error, and depth of investigation for the electrical resistivity array. In some variations, scoring comprises weighting each of the two or more estimations prior to combining them.

Applying current and recording voltages from a subject using only those electrical resistivity arrays meeting a selection criterion based upon their scores may include comparing scores between the electrical resistivity arrays and using only those whose scores are within a predetermined range of values. In some variations, applying current and recording voltages from a subject using only those electrical resistivity arrays meeting a selection criterion based upon their scores comprises ranking scores of the electrical resistivity arrays and using a predetermined number of the electrical resistivity arrays having the highest score values. Applying current and recording voltages from a subject using only those electrical resistivity arrays meeting a selection criterion based upon their scores may comprise ranking scores of the electrical resistivity arrays and using a predetermined number of the electrical resistivity arrays having the lowest score values.

In another variation, a method of determining which subset of electrical resistivity arrays from a plurality of electrodes in a sensor to use to determine a relative spatial change in subsurface resistivities across frequencies may include: positioning the electrodes on a subject; scoring a plurality of electrical resistivity arrays, wherein each electrical resistivity array comprises a pair of current-injecting electrodes and a pair of voltage detection electrodes, wherein the score comprises an estimation of signal error for the electrodes in the electrical resistivity array and an estimation of a depth of investigation for the electrical resistivity array; applying current and recording voltages from a subject using only those electrical resistivity arrays meeting a selection criterion based upon their scores; and determining a relative spatial change in subsurface resistivities across frequencies using applied currents and resulting voltages only from those electrical resistivity arrays meeting the selection criterion.

Also described are systems for determining a subject's tissue hydration using a subset of electrical resistivity arrays from a plurality of electrodes in a sensor to determine a relative spatial change in subsurface resistivities across frequencies. Such a system may include: an electrical resistivity array selector configured to score an electrical resistivity array, wherein each electrical resistivity array comprises a pair of current-injecting electrodes and a pair of voltage detection electrodes; a controller configured to apply currents at a plurality of different frequencies between current-injecting electrode pairs to concurrently receive resulting voltage information from pairs of voltage detection electrodes of from those electrical resistivity arrays meeting a selection criterion based upon their scores; a processing unit in communication with the controller that is configured to determine a relative spatial change in subsurface resistivities across frequencies based on stimulation parameters of the applied currents and the resulting voltages; and an output for outputting a representation of water content for a volume of the subject's tissue from the relative spatial change in subsurface resistivities.

BRIEF DESCRIPTION OF THE DRAWINGS

FIG. 1F is a table for a Wenner array of electrodes, modeled from preliminary data showing that values can be predicted to within a reasonable measurement error.

FIG. 3A shows one example of an array of electrodes as described herein.

FIG. 4 is a schematic of one variation of a system as described herein.

FIG. 9B shows a spatial map of the apparent resistivities.

FIGS. 22A-22J show Table 2, showing DCIs that satisfy: (1) Relative % depth variance less than 3%; and (2) line charge K-factor does not vary from point charge K-factor by more than 3%.

DETAILED DESCRIPTION

The devices, systems and methods described herein allow non-invasive determination of one or more measures of soft tissue hydration which is largely indifferent to body habitus (e.g. skeletal and thoracic geometry across subjects). These methods, systems and devices utilizing the relative spatial change in subsurface resistivities across frequencies (RSCSRAF). The RSCSRAF may be taken within a subject to cancel out insulating boundary conditions presented by the outer shape of the subject's torso. Several metrics of soft tissue hydration may be determined from the RSCSRAF.

To provide a measure of soft tissue hydration across subjects of varying body habitus (e.g., skeletal and thoracic geometry), these systems, devices and methods compensate for the effects of varying anatomical geometry on the electrical apparent resistivity measurements. The outer shape of a subject's torso and non-conductive tissue typically presents an insulating boundary condition. Tissue structures such as bone appear as an insulator relative to muscle. It is well known that insulating boundary conditions influence the direction of the current lines of flux and thus the electric fields. The boundary has more influence on current lines and electric fields when an electrode is closer to a boundary.

For apparent resistivity measurements taken on the torso, with an array of electrodes (the sensor) with spacing chosen to provide sensitivity to underlying tissue, the finite boundary conditions of the torso should be considered. If the finite boundary conditions are not considered or accurate, the spatial resistivity values derived by electrical resistivity tomography will be inaccurate (also known as electrical impedance tomography).

A problem arises incorporating the torso boundary shape into calculating electrical resistivity tomography, as the geometry of the human torso varies significantly among people. Models of the human torso are constructed as an attempt to incorporate the boundary into the electrical resistivity problem. A boundary model may be an ellipsoid with principle dimensions similar to that of the human torso or, the models may be imported from other imaging modalities. However, these techniques are prone to error, require external tools, and take time to measure. Whatever the model, the imperfect fit of the model to the actual subject will generate errors on the boundary of the forward problem and propagate errors to spatial resistivities found using inverse problem techniques.

Figure 1B:
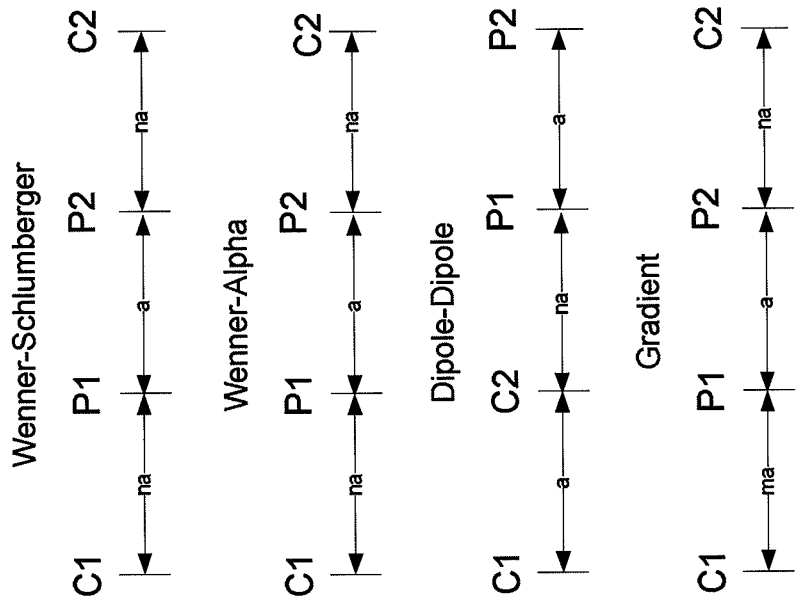
FIG. 1B illustrates four variations of electrical resistivity arrays that may be used.
Figure 1A:
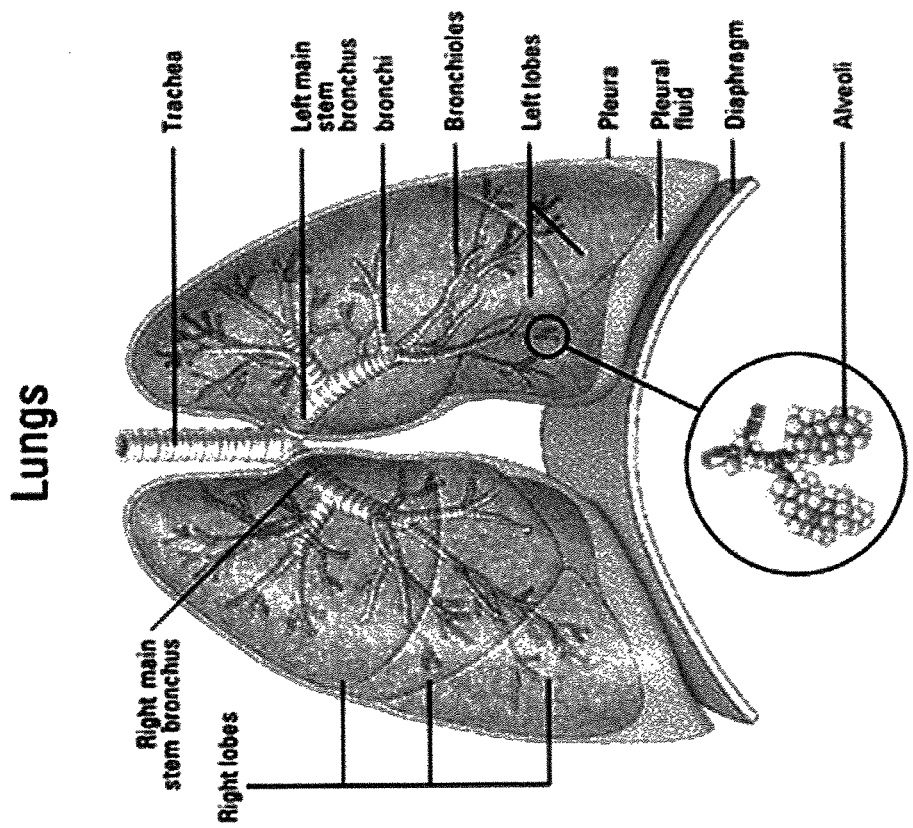
FIG. 1A shows a pair of lungs, illustrating some off the structures within and surrounding them.

As described in greater detail below, an electrode array can be configured to consist of typically four electrodes where two electrodes are used for measuring electric current and two electrodes are used to measure differential voltage. The sensor, applied to the subject, contains numerous fixed spaced electrodes of which thousands of electrode arrays can be configured. When a tetrapolar array is used to measure apparent resistivity it is referred to as an electrical resistivity array. Different electrical resistivity arrays may provide better signals for determining tissue wetness, and the quality and sensitivity of the estimates for tissue wetness may be enhanced by using a subset of all possible arrays. The electrodes may be divided into electrical resistivity array consisting of sub-sets of the electrodes that are used for application/sensing of current/voltage to estimate tissue wetness. To understand the structure and function of an appropriate sensor (and the configuration of electrical resistivity array), consider an exemplary sensor comprising an electrical resistivity array of four electrodes that may be used for measuring electric current and differential voltage. In general, common electrical resistivity array types may include Wenner-Schlumberger, Dipole-Dipole and Gradient. Electrode arrays are widely used to measure resistivity across both large and small scales, for example, ground water reservoir surveys in geophysics and wafer fabrication applications in semiconductor manufacturing, respectively. FIG. 1B illustrates three common sub-array types, where the current is driven between C1 and C2 and voltage drop is measured across P1 and P2.

In many applications in geophysics, the electrodes may be considered as ideal points, since the electrode dimensions are significantly smaller than the electrode spacing within the array, and both the electrode dimensions and electrode spacing are significantly smaller than the size of the earth. In such a case, the $$\frac{\Delta V}{I}$$

is transformed into the apparent resistivity $\rho_a$ by means of a geometric factor, k, $$\rho_a = k \frac{\Delta V}{I}, \text{ where}$$

$$k = \frac{2\pi}{\left(\frac{1}{r_{C_1P_1}} - \frac{1}{r_{C_2P_1}} - \frac{1}{r_{C_1P_2}} + \frac{1}{r_{C_2P_2}}\right)}.$$

The equations above demonstrate that when it is appropriate to model the electrical resistivity array as points, such as in geophysics applications, the geometric factors depend on electrode spacing.

However, in practice, electrodes cannot be considered simply points, as there has to be some dimension associated with the electrode and its area has to be suitably large to inject current into the body. For measuring in a subject's body, the electrodes cannot be spaced far enough apart as to consider the electrodes as points. For example, in some variations described herein, the sensor is a combined electrical resistivity array having 31 rectangular electrodes, each electrode is approximately 2 inches long and 0.15 inches wide and spaced as close as approximately 0.36 inches, to as far as approximately 10 inches. In this case, due to the size of each electrode relative to the spacing between electrodes, it is inaccurate to model the electrodes as ideal points. Instead, each rectangular electrode may be approximated by an ellipsoidal electrode, as this electrode shape can be produced by a simple line-charge, and thus, produce a compact mathematical expression that models the voltage drop across an electrical resistivity array having electrodes with finite area.

For example, the potential at some distance r away from a point-source may decay as $$\phi \propto \frac{1}{r} = \frac{1}{\sqrt{x^2 + y^2 + z^2}},$$

where x, y and z are the canonical coordinates in Euclidian three-space, and hence, a line charge of length 2e will produce voltage $$\phi \propto \int_{-e}^{+e} \frac{d\zeta}{\sqrt{x^2 + y^2 + (z-\zeta)^2}} = \frac{1}{e} \ln \left| \frac{z + e + \sqrt{x^2 + y^2 + (z+e)^2}}{z - e + \sqrt{x^2 + y^2 + (z-e)^2}} \right|.$$

This line-charge model produces a constant voltage source on the surface of an ellipsoidal electrode with foci±e and whose semi-minor axes are equal (A. Sommerfeld, "Vorlesungenüber Theoretische Physik," Band III: Elektrodynamik. Akademische Verlagsgesellschaft Geest and Portig, Leipzig, 4th Ed., pp. 48-49, (1967)). The analogous voltage potential is given by $$\phi(x, y, z) = \frac{I\rho}{4\pi e} \ln \left| \frac{z + e + \sqrt{x^2 + y^2 + (z+e)^2}}{z - e + \sqrt{x^2 + y^2 + (z-e)^2}} \right|,$$

where $$e = \sqrt{l^2 - \frac{d^2}{4}},$$

is the length and d the diameter of the electrode (J. Igel, "On the Small-Scale Variability of Electrical Soil Properties and Its Influence on Geophysical Measurements," Ph.D. Thesis, Frankfurt University, Germany (2007)). Because the electrode has geometry, the voltage contribution has to be integrated along the length l of the potential electrode, $$\phi = \frac{I\rho}{4\pi e} \int_0^l \ln \left| \frac{z + e + \sqrt{r^2 + (z+e)^2}}{z - e + \sqrt{r^2 + (z-e)^2}} \right| dz.$$

Figure 1C:
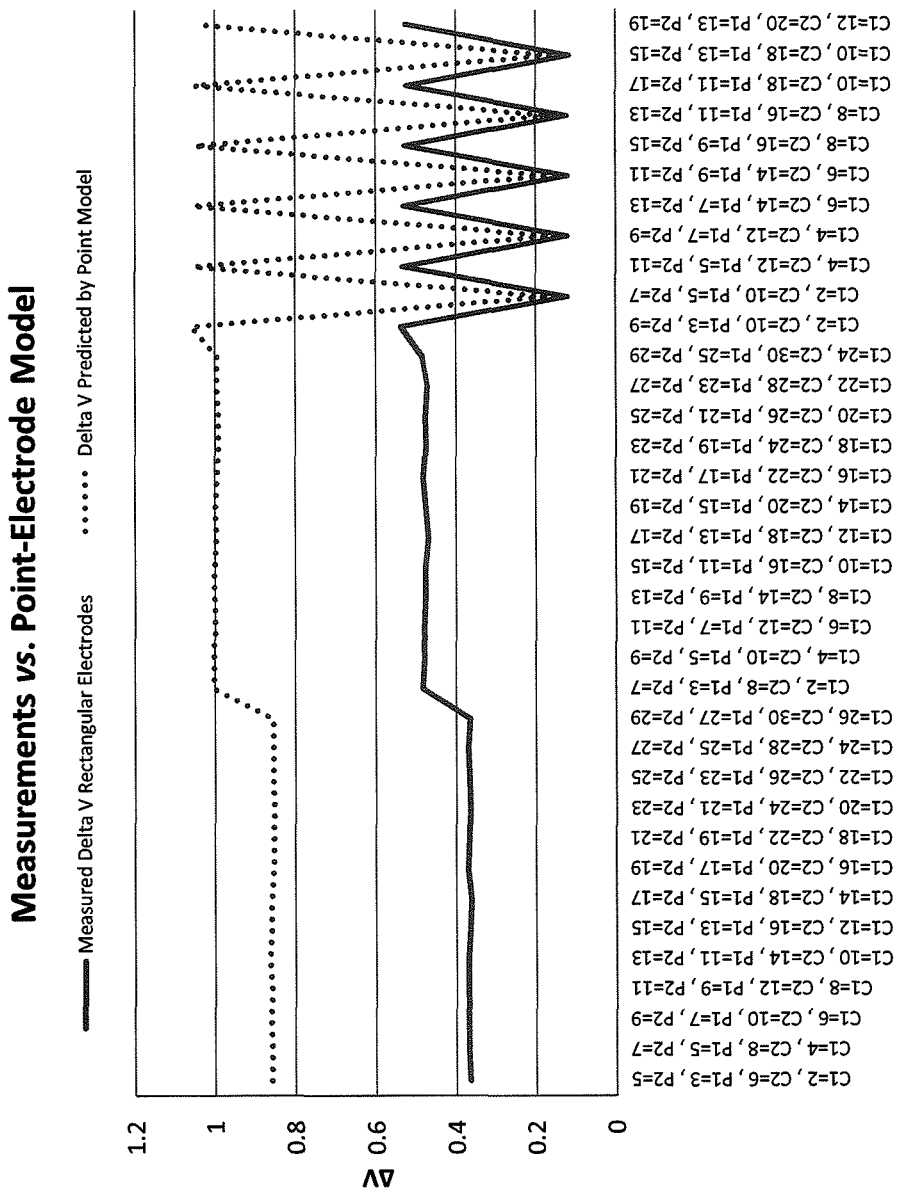
FIG. 1C is a graph comparing 36 Wenner-Schlumberger type electrical resistivity arrays using point electrodes verse measured values using rectangular electrodes
Figure 1D:
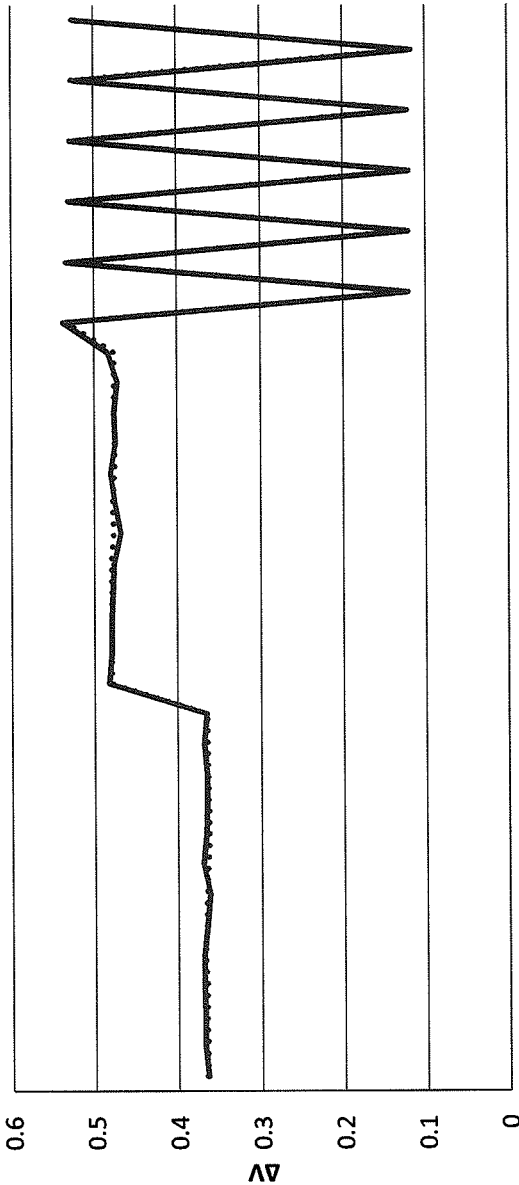
FIG. 1D is a graph comparing 36 Wenner-Schlumberger type electrical resistivity arrays using the line-charge electrode model verses the measured values using rectangular electrodes (to be contrasted with FIG. 1C).

The geometrical factor associated with an electrical resistivity array can likewise be calculated by summing the contribution from the four electrodes, $$K_{ellipse} = \int_0^l \frac{4\pi e\, dz}{\ln|f(r_{C1P1})| - \ln|f(r_{C1P2})| - \ln|f(r_{C2P1})| + \ln|f(r_{C2P2})|},$$

where $f(r) = \dfrac{z + e + \sqrt{r^2 + (z+e)^2}}{z - e + \sqrt{r^2 + (z-e)^2}}.$ To confirm that the ellipsoidal model better describes the voltage measurements taken using physical electrodes, a tank with a bottom area of 23.75×11.75 in² was filled to a height of 8.5 inches with saline (resistivity 5.44 Ωm), and a stainless steel version of the sensor was placed on its waterline. One hundred and five distinct drive pairs were used to inject current into the tank and this resulted in thousands of unique electrical resistivity arrays, each reporting back a single apparent resistivity. A small subset of these electrical resistivity arrays, those that are of the Wenner-Schlumberger type and those electrodes that are close to each other, are shown in FIGS. 1C and 1D. The first plot (FIG. 1C) compares the voltage drop across P1 and P2 (ΔV) as measured by the instrumentation using rectangular electrodes (solid line) and the voltage drop predicted by the point-electrode model (dotted line). As is evident from FIG. 1C, when the electrodes are close to each other, the point-electrode model fails to correctly predict the voltage drop across P1-P2.

The second ellipsoidal electrode model achieves good agreement with experimental values, as can be seen in FIG. 1D. In this case, even electrodes located next to each other (i.e., C1=2, C2=6, P1=3 and P2=5), which were mismatched by over 130% using a point-electrode model, match with an error of less than 1% using this line-electrode model when compared to measured data. This good agreement with experimental data implies that the line-electrode model correctly captures the size of the voltage drop, and hence, can be used to specify electrical resistivity arrays whose voltage drop can be ascertained accurately to some predefined voltage threshold given by the accuracy of the measurement device.

In the systems, devices and methods described herein, because of the relative spacing of electrodes with respect to the size of the human torso, the human torso cannot be modeled as an infinite half sphere, as with geophysical models. The outer shape of the torso, given the approximate electrode spacing of the sensor, will substantially influence the current lines and electric fields within the torso. Analytical models that translate tetrapolar apparent resistivity measurements on a finite bounded model are often difficult to derive. However, the literature provides several analytical models for simple geometric shapes. A case in point would be the analytical model of a tetrapolar apparent resistivity measurement on a flat surface of a bar shaped semiconductor provided by Hansen (E. Hansen, "On the influence of shape and variations in conductivity of the sample on four-point measurements," Applied Scientific Research, Section B, Vol. 8, No. 1, pg. 93-104, (1960)), where the electrodes are modeled as points. Hansen's analytical model is derived for a bar shaped semiconductor. Hansen derives his model from point electrodes; it does not take into account electrode geometry. However, when the distance between electrodes is sufficiently large, the voltages of rectangular electrode converge to that of a point electrode. The extension of Hansen's equation to a box model is shown below $$F_\alpha = \frac{2\pi s^2}{ah} + \frac{16\pi s}{ah} \sum_{\substack{m=0 \\ (m,n)\neq(0,0)}}^{\infty} \sum_{n=0}^{\infty} \frac{\cosh\beta\left(l - \frac{3s}{2}\right)\sinh\left(\frac{\beta s}{2}\right)}{(1+\delta_{0,m})(1+\delta_{0,m})\beta\cosh(\beta l)} +$$

$$\frac{16\pi s}{ah} \sum_{m=1}^{\infty} \sum_{n=0}^{\infty} \frac{(-1)^{m-1}\sin^2(m\pi\Delta/a)\cosh\gamma\left(l - \frac{3s}{2}\right)\sinh\left(\frac{\gamma s}{2}\right)}{(1+\delta_{a,m})\gamma\cosh(\gamma l)}, \text{where}$$

$\beta = (2\pi/a)\sqrt{m^2 + (na/2h)^2}$ and $\gamma(\pi/a)\sqrt{m^2 + (na/h)^2}$.

To mathematically model the forward problem of one of the electrical resistivity arrays, out of the thousands available from a sensor, it is possible to combine the translation constants of Summerfeld and Hansen in the following equation:

$$\Delta V_{complete} = \frac{F_\alpha \rho_\alpha I}{k_{ellipsoid}}$$

Figure 1E:
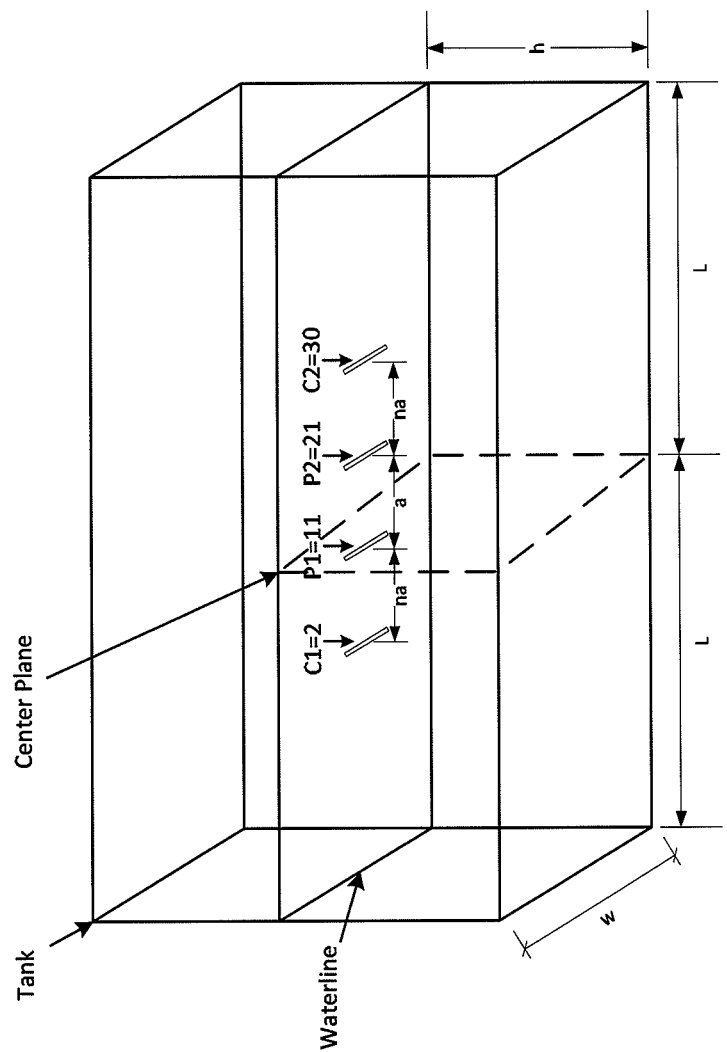
FIG. 1E is a representation of a saline tank model that may be used to test many of the devices, systems and methods described herein.

To verify the correction factor $F_\alpha$, the voltage across P1 and P1 was predicted for a Wenner-Alpha electrical resistivity array from the sensor over three homogenous saline tank models. FIG. 1E illustrates a tank model. In this example, the stainless steel electrode dimensions are: 0.0508 m×0.00381 m; the tank dimensions are: L=0.301 m, a=0.298 m; the electrode spacing is: s=0.085 m.

As shown in the table of FIG. 1F, for a Wenner resistivity array; given a current, the resistivity of the saline, the Hansen's boundary correction coefficient, Summerfeld's line charge coefficient, and the voltage drop across P1-P2 can be predicted to some measurement error. For example, a reasonable error may be error of less than 5%.

In the preceding calculations, $F_\alpha$, $k_{point}$, $k_{ellipse}$ and $\rho$ are real numbers. However, while $F_\alpha$, $k_{point}$, $k_{ellipse}$ are real numbers, for capacitive biomaterials, $\rho$ is a frequency dependent complex number $$\rho = \rho' - j\rho'' = \frac{1}{\sigma} = \frac{(\sigma' - j\sigma'')}{|\sigma|^2}, \text{ where}$$

$$\sigma \equiv \sigma' + j\sigma'',$$

$$\varepsilon \equiv \varepsilon' - j\varepsilon'' \equiv (\varepsilon_r' - j\varepsilon_r'')\varepsilon_0,$$

with the following properties listed in the table below.

| | |
|---|---|
| $\sigma = j\omega\varepsilon$ | $\sigma'' = \omega\varepsilon'$ |
| $\sigma' = \omega\varepsilon''$ | $\varepsilon'' = \dfrac{\sigma'}{\omega}$ |
| $\varepsilon' = \dfrac{\sigma''}{\omega}$ | $\rho'' = \dfrac{\sigma''}{|\sigma|^2}$ |
| $\rho' = \dfrac{\sigma'}{|\sigma|^2}$ | |

For rectangular electrodes on a sufficiently large box, the apparent resistivity is $$\rho_a = \frac{k_{ellipsoid}\Delta V_{complete}}{F_a I}.$$

Because the resistivity is complex valued and frequency dependent, the calculated spatial resistivity at two frequencies would yield a spatial resistivity for the low frequency and for the high frequency: $\rho_a^{low}$ and $\rho_a^{high}$. Note that in taking the relative percent difference (RPD which is a special case RSCSRAF) between $\rho_a^{low}$ and $\rho_a^{high}$, the boundary and geometrical factors cancel, such that $$RPD = 100 \frac{\rho_a^{low} - \rho_a^{high}}{\rho_a^{high}},$$

which can be simplified to $$RPD = 100\left(\frac{V^{low}}{V^{high}} \cdot \frac{I^{high}}{I^{low}} - 1\right),$$

and captures the change in resistivity of the subsurface without requiring geometrical information of the sensor or boundaries.

Thus, as described, a system may be built on the realization that the RSCSASRAF captures the change in resistivity of the subsurface without requiring geometrical information of electrical resistivity array or boundaries, and to expand the concept to spatial resistivity, resistivity beneath the subsurface of a sensor.

The systems described herein may use a combined electrical resistivity array, which may be referred to as a sensor, which serves as the subject-applied portion of a medical device apparatus or system that determines the spatial relationship of the RSCSARAF in soft tissue beneath the surface of the sensor. The sensor may contain tens of fixed-spaced electrodes of which thousands of four point resistivity arrays can be configured. The medical device apparatus may determine the spatial relationship of the RSCSARAF in each cell of a mathematically determined, two or three-dimensional, multi-cell, cross-sectional grid, extending horizontally and vertically beneath the sensor. The grid may span a maximum horizontal distance equal to that of sensor and may be sized in the vertical dimension to a specified depth of investigation (DOI). The dimensional may be determined for each cell in the grid by driving current and measuring voltage in a manner that is common in electrical resistivity array surveys and using mathematical inversion methods to construct a spatial image of the dimensional within the grid. The sensor and medical device apparatus have the capability of determining soft tissue hydration.

In general, the devices and systems described herein are used by first placing the sensor (e.g., an array of electrodes including electrodes arranged in a predetermined pattern) on a subject. The placement location may be chosen to optimize the sensitivity and result of the system. Thereafter, the system may use the sensor to measure one or more electrical properties (e.g., voltages, complex impedances, complex conductivities, etc.) from the subject. The system or device then typically determines the spatial relationship of resistivities (or a derived value) using the known arrangement of the electrodes in the array as well as the known applied currents and the sensed electrical properties at a plurality of the electrodes in the sensor and solving inverse problems. In general, the subsurface spatial resistivities are solved for using this information. However, because the apparent resistivities are sensitive to a geometric factor (referred to herein as k, or the k factor) that depends on the boundary conditions and arrangement of the electrodes, the systems described herein are configured and adapted to minimize or eliminate the effects of the geometric k factor. In some variations, the system therefore calculates a relative percent difference between the spatial arrangements of resistivities determined at a low frequency and at a high frequency to eliminate the geometric k factor. As described in greater detail below, this calculation of relative percent differences may allow a normalized percent difference that more accurately reflect changes in resistivity reflecting lung wetness.

Sensor/Electrode Placement

Figure 2A:
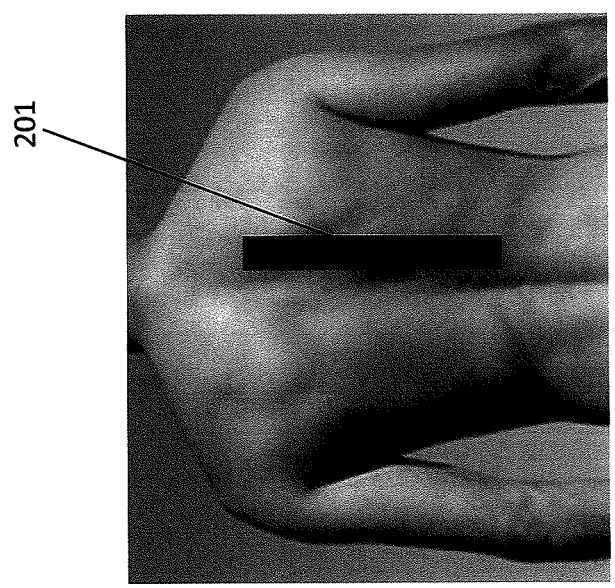
FIG. 2A illustrates a possible location for placement of electrodes or a sensor on a subject's back.
Figure 2B:
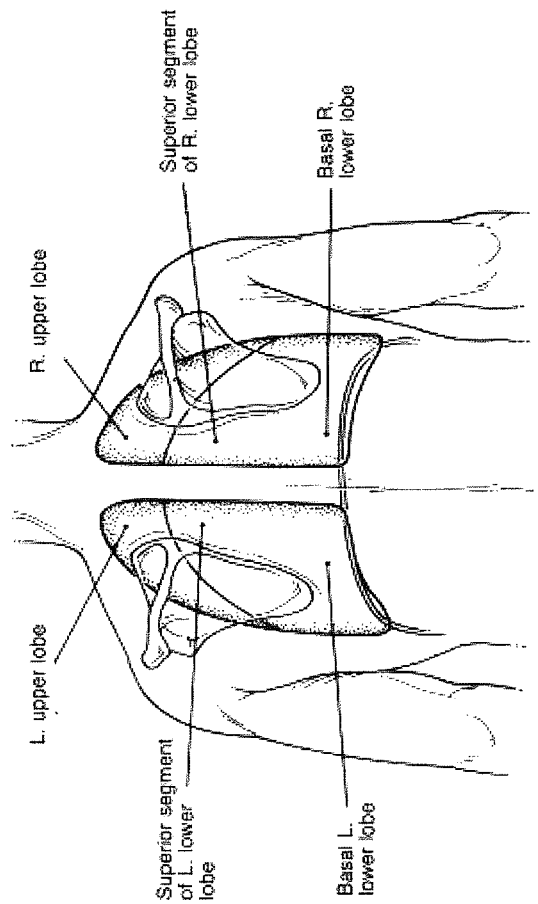
FIG. 2B shows the relationship between the scapula and lungs.

In general, a sensor defined by an array of electrodes (e.g., a strip array of electrodes) may be placed on the subject's back in a particular arrangement allowing for detection of lung wetness. For example, FIG. 2A shows one example of a sensor (configured as a strip of electrodes) positioned on a region of the subject's back (to the right or left side of the subject's midline on their back, lateral to the spine). The sensor 201 (an array of electrodes) may be applied locally in just one region of the subject's back. In FIG. 2A, the electrodes positioned in particular near the midline of the subject's back may be positioned immediately over the lung (either the right or left lung). This may be achieved by placing the top electrode in the sensor in line with the top of the subject's scapula, while extending the rest of the electrodes in the active region of the sensor down the back (cranially to caudally) as shown.

In the examples provided herein, the electrodes are adapted for placement on subject's thorax (e.g. posterior and anterior region of the body) for determining the distribution of resistivities immediately below the array of electrodes (e.g., the skin, muscle and lung tissue). The systems described herein may provide information to aid in determining the fluid content of a lung, which may be relatively deep within the body when compared with skin and muscle. In FIG. 2A, the sensors (array of electrodes) are positioned so that it may be possible to measure from the posterior region of the right lung. In this example the array of electrodes (an example of which is provided below) are positioned about 1 inch lateral of spine, as shown in FIG. 2A. This location may allow depths of investigation to reach the posterior region of the right lung.

In many of the variations of the sensor described herein, the electrodes are arranged on a strip, patch or other fixed arrangement that can be positioned on the skin of the subject. For example, the strip of the electrodes may be an adhesive strip that can be positioned to one side of the subject (e.g., one side of the subject's back). This configuration may allow for sensing a depth beneath the array of electrodes, and therefore determining the arrangement of the resistivities beneath the electrodes. In this arrangement, as opposed to a strap or band of electrodes, the arrangement of electrodes may be fixed relative to each other, so that the geometries between electrodes is fixed and known. Such local electrode positioning may have numerous advantages.

The arrangements, including the spacing, of the drive and sensing electrodes within an electrical resistivity array may be configured to allow sensing both at depth (e.g., deep within the tissue) and at more superficial regions (immediately beneath the electrodes). Part II (below) describes designing a sensor (a combined electrical resistivity array) for determining tissue wetness, as well as devices and methods for selecting which electrical resistivity arrays to be used. The measurements described herein may be made on a subject instructed to sit or lie in a particular posture. For example, when taking lung wetness measurements, the subject may be instructed to lie on his or her belly, lying prone (on his or her back), or sit reclined at an angle (e.g., 45°) when taking the measurement. In some variations the subject may be asked to assume the same position when taking measurements at different times. Typically, in heart failure the lungs get wet, and the weight of the fluid in the lungs may alter its distribution. For example, in the lungs, the weight of the fluid may partially compress or collapse the lower region of lung. Posturally, it may be desirable to have the subject lie supine or nearly supine; this may help make the lung wetness easier to measure, particularly when placing electrodes on the subject's back.

In general, a sensor may contain a plurality of electrodes, typically of both drive electrode and sensing electrode types. The drive and sensing electrodes may be identical, or may have different geometries. In some variations, the same electrodes may be used to both drive and sense (at different times or simultaneously). In general, the electrodes may be electrically connected to the rest of the system via a wired or wireless connection (not shown in FIGS. 2A and 2C).

Figure 2C:
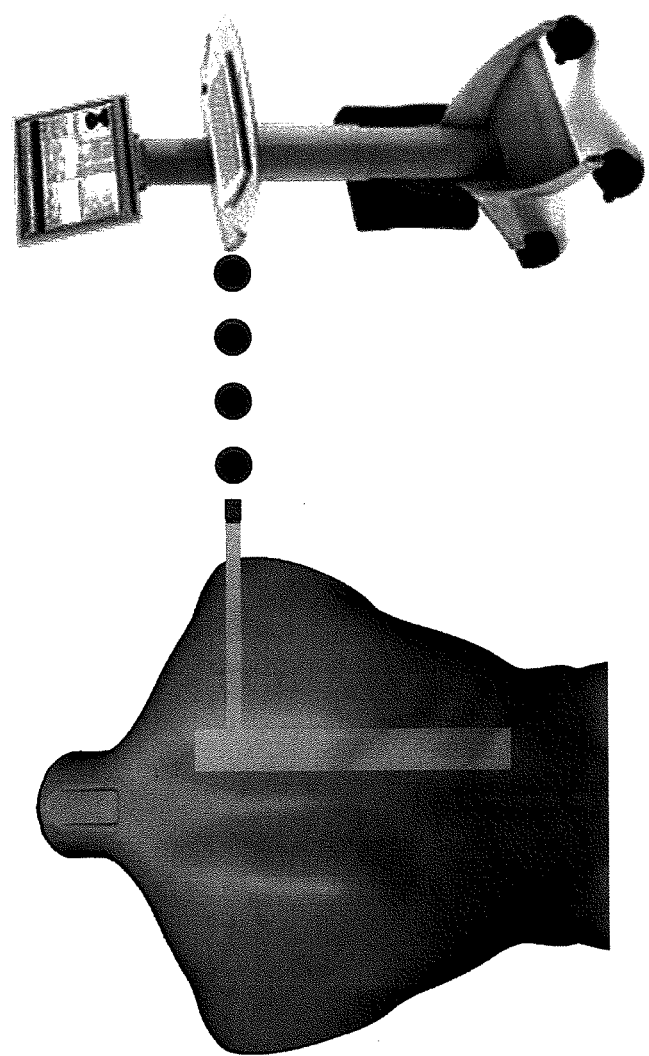
FIG. 2C is one representation of a system for measuring lung wetness as described herein.

FIG. 2C illustrates one example of a system for measuring lung wetness. In this example, the system includes a disposable sensor that is connected to a reusable monitoring/processing station. The monitoring/processing station includes a controller for regulating the application of drive current and coordinating sensing from the sensing electrodes and processing of the received signals. The system may also include one or more processors for determining a spatial representation of resistivities beneath the sensor of electrodes at different applied current frequencies. The same, or a different, processor may also determine a spatial mapping of relative spatial change in subsurface resistivity across two or more frequencies (e.g., a high frequency and low frequency) and may then determine lung wetness based on the RSCSRAF.

FIG. 3A illustrates one variation of a strip array (sensor) that may be used. For example, in FIG. 3A the electrode array 305 includes drive electrodes 303 alternating with sensing electrodes 307. In this example a total of 31 electrodes are included in the array, with the electrodes arranged down the length of the array. Each electrode in this example is rectangular in shape. The array in this example is configured as a sensor that includes a hydrogel that may be applied directly to a subject (e.g., the subject's back). In some variations the lateral edges of the electrodes extend to the edge (or almost to the edge) of the sensor. Thus, in some variations, as shown in FIG. 3A, the sensor includes a proximal 323 and distal 323' grip or holding region for grasping to apply the sensor. In some variations the patch or sensor array may include one or more indicators and/or graphics to aid in placement and/or orientation. For example, the patch or sensor may include a graphic that indicates the middle of the patch or sensor.

In one variation the patch is formed to include a plurality of electrodes attached to a polyester backing (including a titanium powder for bacteria resistance). The patch may be formed of a medical grade dielectric material that is UV cured onto the bottom. The electrodes may be connected by insulated vias (e.g., connectors, not shown). In some variations, the arrangement of the electrodes of the patch is predetermined, and matched to the processor of the system. For example, the patch may have a "standard" arrangement that is used by the system, or there may be a variety of patch electrode configurations from which the system may select to match the arrangement of the actual patch to be used. Thus, the system or device may include information describing and corresponding to the arrangement/configuration of the electrodes (including electrode numbers, sizes, etc.) in a particular type of patch, or the patch may itself provide this arrangement/configuration to the rest of the system, so that it can be passed onto the processor and used by the system in determining the distribution of RSCSRAF as described below. For example, a sensor may include a chip or other identifier that confers this information to the rest of the system.

Figure 3B:
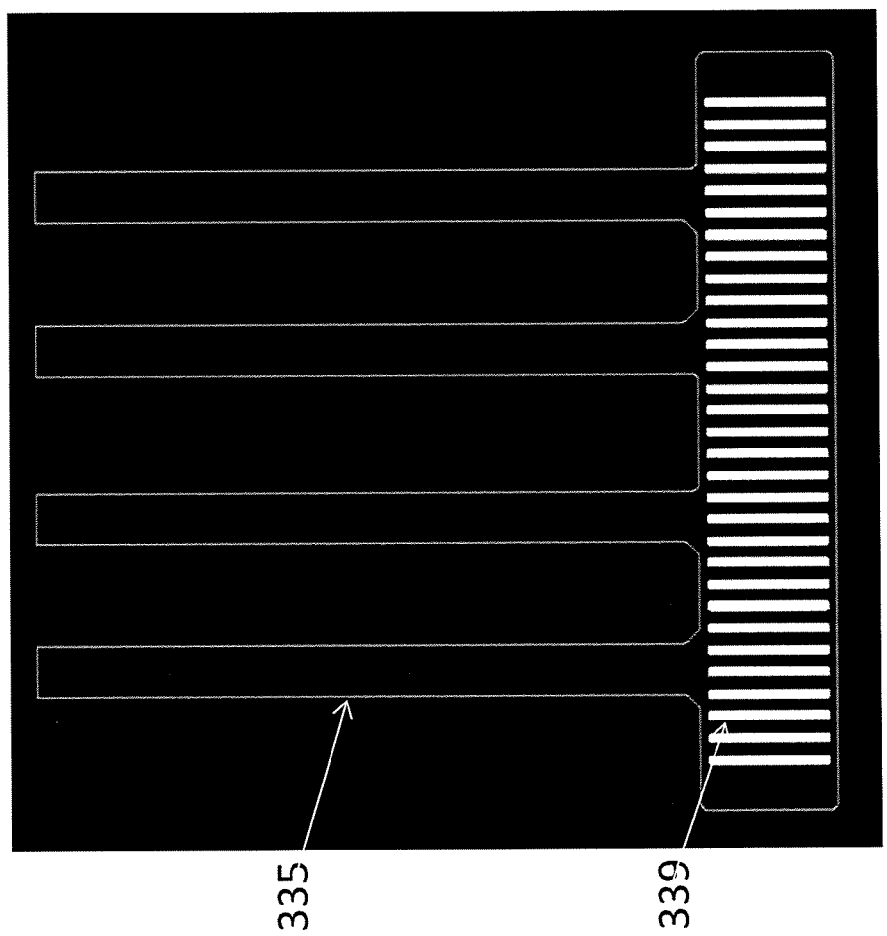
FIG. 3B is a schematic of another variation of an array of electrodes as described herein.

Another example of a patch design including a plurality of drive and sensing electrodes is shown in FIG. 3B. In this example the patch shows four regions from which the leads 335 extend from the electrodes 339. The leads are typically insulated and configured to connect with the rest of the system. Although this example shows four bundles of leads extending laterally from the patch, in some variations fewer or more bundles of leads (e.g., 1, 2, 3, etc.) may be used. The lead bundles may be fabricated as part of the fabrication processes (e.g., photolithographically, screen printing, etc.).

As mentioned above, to determine lung wetness, the sensor (e.g., patch) may be applied to the user's back in a position that is laterally offset from the spine (e.g., midline of the back) by approximately 1 inch, so that the lateral edge of the electrodes is 1 inch from the midline. The top electrode in the patch may be lined up with top of scapula, so that the remaining electrodes run parallel down the back, transverse to the midline, as shown in FIGS. 2A and 2C. In these examples, the active region of the patch extends approximately 11 (e.g., 10.8) inches, so that the electrodes span this distance down the cranial-caudal axis of the back. The electrode spacing is approximately 0.36 inches center to center in the example shown in FIG. 3B, and the electrodes are rectangular, having a width of approximately 0.15 inches and an elongate length of approximately 2 inches. Although other geometries may be used, in general, these geometries are optimized for the patch because they allow a relatively large surface area for the electrode, while making consistent and complete contact with the subject's back, which is often curved or irregularly shaped. Thus, it may be beneficial to have the active region of the patch be between about 8 and 12 (e.g., 10) inches long and between about 1.5 and about 2.5 (e.g., 2) inches wide. The lateral amount of support backing on either side of the active region may be minimized as well. Minimizing the amount of lateral material may prevent the patch from buckling, wrinkling, or puckering as it is applied/worn. The relatively narrow width of the patch may help it to conform to the contour of skin. Overall the patch is flexible, and in the examples shown in FIGS. 3A and 3B, has a thickness of less than about 3 mils, which may also help it conform to the body contour.

In some variations, the sizes and shapes of the electrodes may be selected to optimize the sensing ability of the system. For example, the area of each electrode in the sensor may be selected to allow sufficient current to be delivered so to increase the signal to noise ratio on measurements taken. The electrodes may be long and narrow to allow close spacing between the electrodes to provide sufficient resolution, while the length may be sufficiently large so that the current density can be sufficiently low. The width of the electrodes may be limited to allow detection of the tissue beneath the electrodes between the spine and the scapula, so that the electrodes may be placed over this narrow region of the body that allows a "window" to detect the lungs. The spacing may also be important to allow sufficient depth of penetration/sensing into the subject's body. The arrangement shown in FIG. 3A, for example, is configured to allow a depth of investigation of approximately 2 to 2.5 inches. The electrically conductive members (electrodes) do not contact each other, and are spaced adjacent, but sufficiently far enough apart to prevent electrical coupling while allowing the electrodes to measure the voltage seen by the current applied by the current-injecting or driving electrodes.

In practice, the systems may be configured to view the lung, and thus may be placed as illustrated in FIG. 2A, by securing them to the subject's back approximately 1 inch lateral of the spine, between the spine and scapula. The linear electrode array is placed up/down relative the subject's body (e.g., cranial to caudal, from head to feet) in parallel to the spine. The strip of electrodes may be placed as high as possible (e.g., to the level of the armpit). The electrode strip may be used with, or may include a conductive gel (e.g. hydrogel) that helps make the electrical connection with the skin. The strip could be placed either on the left or right side of the spine.

As mentioned above, the structure of the array is predetermined. Thus, the patch controls the spacing between electrodes. In this example, the patch of electrodes is approximately 2 inches wide (e.g., 50 mm wide). The example of FIG. 3A shows alternating drive and sense electrodes. In this example, there are 31 electrodes; 16 of them are voltage sensing (listen) electrodes and 15 are current drive electrodes.

Figure 3C:
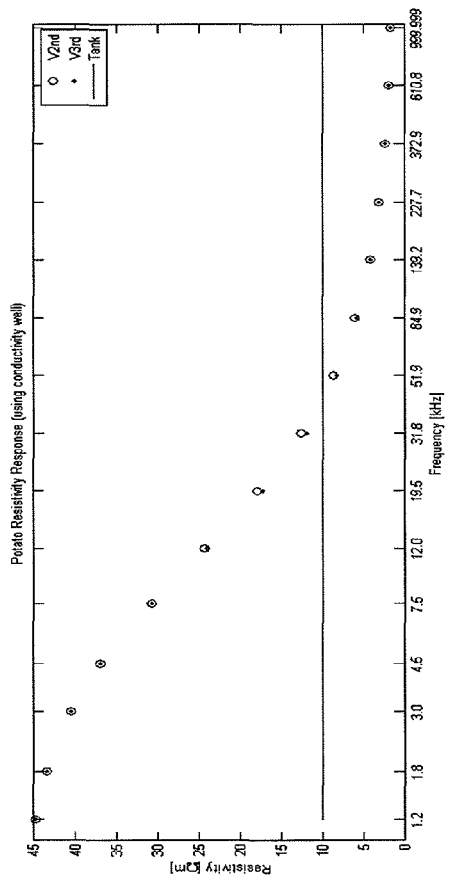
FIG. 3C shows the frequency response of the resistivity of a test object (e.g., potato).

To test the concept of RSCSRAF to detect a biological structure in the subsurface of the patch, a potato was placed in three positions a saline tank (FIGS. 3D, 3E, and 3F), with the background saline resistivity of 10 Ω·meter. The potato was placed in three positions of the tank; left, center and right. The frequency response of the resistivity of the potato is shown in FIG. 3C.

Figure 3G:
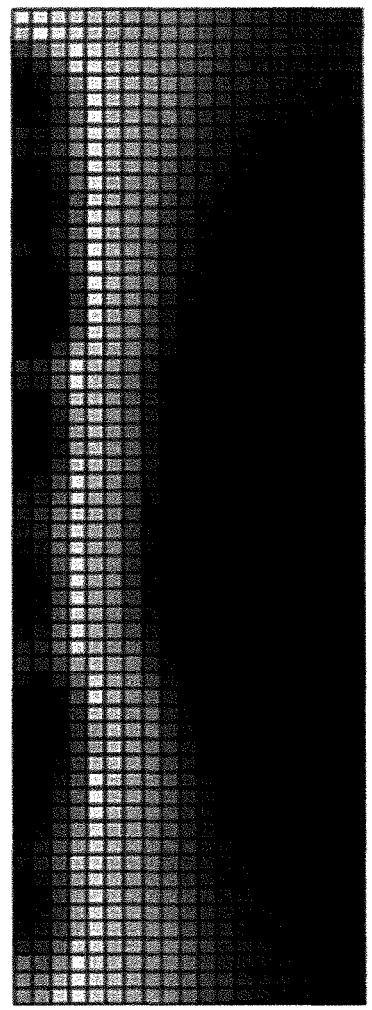
FIG. 3G show another exemplary heat map showing the RSCSRAF of another biological model ("ribs" formed of a potato and plastic).
Figure 3D:
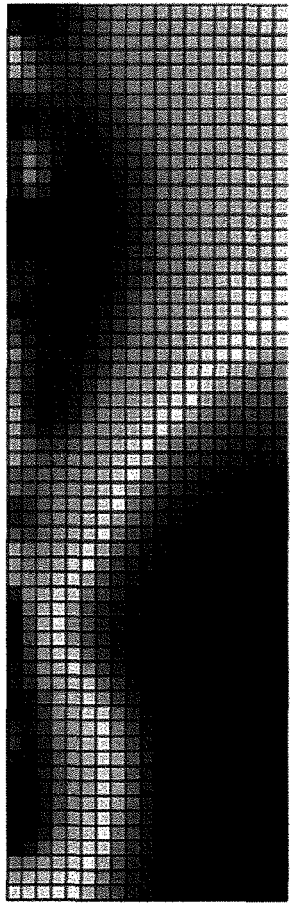
FIGS. 3D, 3E and 3F show heat maps of the RSCSRAF for the test object (potato) in a left, middle and right position within a test tank of saline.
Figure 3E:
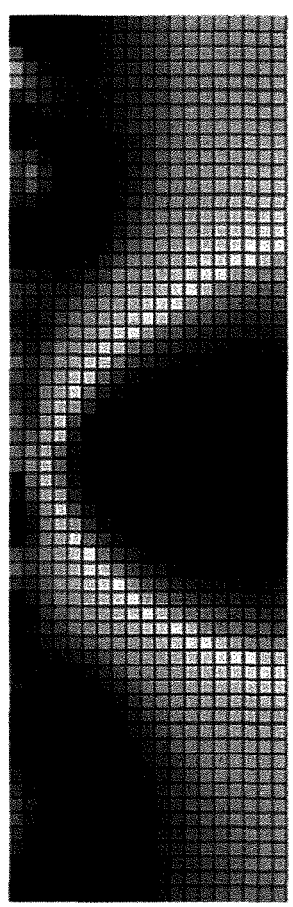
Figure 3F:
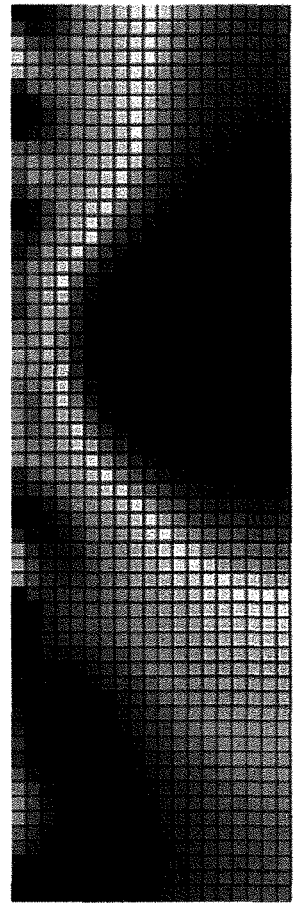

FIGS. 3D, 3E, and 3F show a heat map of the RSCSRAF for each of the three positions of the potato sample (left, center and right), clearly showing that the system can image saline as having a low percent difference in spatial resistivity between two frequencies and shows the ability to track movement of biological structures beneath the patch.

As a proof of principle, an experiment was performed to determine if the system could detect saline beneath a biological structure separated by ribs. The biological tissue was mimicked using cut potatoes, the ribs were mimicked using a plastic grid. The thickness of the potatoes and grid was approximately 1 inch. The image in FIG. 3G shows a heat map of spatial relative percent difference in resistivity between two frequencies, clearly showing that saline, a substance of low percent difference in resistivity can be detected beneath a biological structure which includes ribs.

In operation, when determining lung wetness, the array of electrodes is first placed on the subject's torso, and the electrodes are connected to a processing unit. The system (e.g., a controller) selects two electrodes at a time as a current pair. A small electrical current is then passed between each pair of electrodes. Voltages may be recorded by electrodes positioned between the drive pair; although it may be possible to use electrodes outside of the drive pair as well. In some variations, the current and voltage data may be transferred to a secondary processing unit. Thus the system may include circuitry (e.g., a first processing unit) that is configured to condition and/or enhance the received voltage. In some variations only a single processing unit is included, which may integrate the function of the electrode conditioning/driving and analysis of the current/voltage signals.

For example, FIG. 4 illustrates one variation of a system 400 including an array of electrodes 401. The array of electrodes may be part of a patch or fixed positioning system, as just described, including both drive and sensing electrodes. In this variation, the electrodes are connected to one or more first processors 403', 403", 403'" that includes active circuitry for conditioning and handing the current-injecting/detected signals. The first processors may connect to a controller and/or processor 405. The controller may be integrated with additional processors, or it may be a separate element 407.

After the array of electrodes of known geometry (e.g., spacing, size and configuration of the electrodes, relative to each other) has been applied, the system may apply currents from the drive electrodes and detect voltages using the sensing electrodes between the drive electrodes. The applied and sensed voltages and currents, along with the known spacing of the electrodes may then be used to solve for the distribution of resistivities within the tissue beneath the electrodes.

For example, using an array of electrodes such as that shown in FIG. 3A voltages may be sensed, as currents are applied, from various combinations of drive electrodes. In some variations, it may be beneficial (as described in detail below) to repeat the process for multiple driving current frequencies.

As discussed above, the devices and systems described herein may be used to determine the spatial relationship of resistivities and properties of resistivities of sub-surfaces below an electrode array when the electrode array is applied to a human body of unknown geometry, in such a manner that is least affected by errors in geometry. The geometry refers to the size and shape of the human body and the electrical internal boundaries such as the skeleton and other internal structures. In some variations, this invention may be applied to determine the likelihood of edema from skin layer to approximately 2" to 2.5" below the electrode array, where such areas of interest such as the lung are found.

In one example of the devices, systems and methods as described herein, an electrode array is applied to the body in a region of interest. The purpose of the electrode array is to provide an electro-mechanical connection to the body with predefined electrode spacing. As mentioned, the electrode array may be made up of a backing material with a printed array of electrodes, with printed metallic traces from the connector(s) to the electrodes, with a conductive hydrogel placed over the electrodes and a dielectric to protect and electrically insulate the printed traces. In one example, the backing material is made of polyester with titanium nitride; the electrode may be made of an Ag/AgCl pad measuring approximately 2"×0.150"; the electrode array spacing may be, for example, 0.36" with approximately 30 electrodes (e.g., 31 electrodes) in each array.

The system may include hardware, firmware and/or software including logic to do the following: drive current through any combination of electrodes (current drive logic); measure the complex drive current (current measure logic); and measure complex differential voltages between any combinations of electrodes (voltage measure logic). As mentioned above, the system may also include logic (hardware, software, firmware, etc.) to determine the distribution of apparent resistivities and/or derived values (such as RSCSRAF values).

The systems described herein may determine (from the applied currents and measured voltages) various data types, including particularly spatial estimates of resistivities within the volume of tissue beneath the array of electrodes, and/or relative percent differences between spatial resistivities at different (e.g., between a high and a low) frequencies.

Resistivities

The systems described herein may use either or both apparent resistivities or the logarithm of apparent resistivities. The apparent resistivities are given by the mathematical expression:

$$\rho_a = k \frac{\Delta V}{I}$$

where k is a geometric factor that depends on the boundary conditions and arrangement of electrodes, ΔV is the differential voltage of interest, and I is the current passing through a region of the body between any pair of current drive electrodes. The system may provide multiple complex valued apparent resistivities for the multiple combinations of electrode drive pairs.

Relative Percent Difference (RPD)

Relative percent difference (which, is a type of RSCSRAF and is defined as the relative percent change in the magnitudes of spatial resistivities between two separate frequencies.

$$RDP = 100 * \frac{\rho_a(\omega_L) - \rho_a(\omega_H)}{\rho_a(\omega_H)}$$

Notice, by using the RPD, the geometric factor k cancels.

Phase of Apparent Resistivities

The systems described herein may also measure ΔV and I in complex form so apparent resistivities can take the form:

$\rho_a = k(\text{real} + \text{imag})$.

The phase angle of apparent resistivity is given by:

$$\theta = \arctan \frac{k(\text{imag})}{k(\text{real})}.$$

Again, when describing the phase angle of the apparent resistivity, the geometric factor k cancels.

Sensor Configuration and Electrical Resistivity Array Selection

The combined electrical resistivity array (the sensor), operates as a subject-applied portion of the device or apparatus for determining the spatial relationship of the relative spatial change in subsurface resistivity across frequencies in soft tissue beneath the surface of the sensor, which can be a interpreted to indicate tissue wetness. As described above, a sensor typically includes many electrodes that may be used in various subsets of drive electrodes and sensing electrodes to determine tissue wetness. In general, the more electrodes ($m_{count}$) in the sensor, the more combinations are possible.

In one example, the sensor may contain tens of fixed spaced electrodes, of which thousands of four-point electrical resistivity arrays can be configured. An electrical resistivity array includes two drive electrodes and two sensing electrodes. As described, the system or device typically determines the spatial relationship of the relative spatial change in resistivity in each cell of a mathematically determined, two-dimensional, multi-cell, cross-sectional grid, extending horizontally and vertically beneath the sensor. The grid may be sized to span a horizontal distance equal to that of sensor and may be sized in the vertical dimension to a specified depth of investigation (as defined by the combined electrical resistivity array). The relative spatial change in subsurface resistivities across frequencies may be determined for each cell in the grid by driving current and measuring voltage and using mathematical inversion methods to construct a spatial image of the relative percent differences in resistivity within the grid, as described above.

In an array of $m_{count}$ electrodes thousands of four point electrical resistivity arrays are possible. Of the total possible number of electrical resistivity arrays, the system, devices and methods for determining tissue wetness typically uses a subset of said electrical resistivity arrays within the sensor. It is often desirable to include a very large number of possible electrodes (i.e., large $m_{count}$) to form the available pool of electrodes on the patch from which electrical resistivity arrays of drive/sensing electrodes may be chosen. However, not all electrical resistivity arrays provide equivalently sensitive/accurate signals for determining tissue wetness. The quality and sensitivity of a tissue wetness determination may be improved or optimized by selecting only those electrical resistivity arrays of electrodes from the available combinations in the sensor that would provide the most useful signals for determining tissue wetness. Described herein are systems, devices and methods for determining tissue wetness by selecting which subset of electrical resistivity arrays to use from an array of electrodes. In some variations this may be achieved by rating, grading, and/or scoring an electrical resistivity array and using only those that rate/grade/score sufficiently well to indicate that they would provide high quality signal information. The rate/grade/score (which may be referred to as a score, for convenience) may be compared to a threshold (e.g., a quality threshold) or range of acceptable values. In some variations the score is multidimensional, and may include multiple values. For example, the score for a particular electrical resistivity arrays may include a value (or values) for signal error (e.g., error due to placement, voltage error, current error, combined error, etc.), a value for depth of investigation (DOI), and a value for electrical resistivity array location. In some variations this score may be a combined (and/or weighted) value including one or more of these. As described in more detail below, the signal error for a particular electrical resistivity array may include more than one value (for placement error, voltage error, current error), or a combined (and/or weighted) single value.

A score within the desired threshold range (and/or above, or in some cases below a threshold) indicates that the electrical resistivity arrays should be selected. Conversely, a score could be compared to a rejection threshold/threshold range indicating that the electrical resistivity arrays should not be used. The devices and systems described may rate/grade/score individual electrical resistivity arrays of electrodes, and then use only those electrical resistivity arrays that score above a quality threshold for the tissue wetness determination.

As mentioned, an electrical resistivity array of electrodes is a subset of the total pool of electrodes and typically includes a pair of drive electrodes and a pair of sensing electrodes. Any size and configuration of electrodes forming the electrical resistivity array may be chosen. For example, an electrical resistivity array may include a pair of sensing electrodes between a pair of drive electrodes. More than two sensing and/or driving electrodes may be used.

For example, a sensor for use in determining lung wetness may support a combination of many four point electrical resistivity arrays of which many have a median depth of investigation necessary to reach the lung region in the human body when the sensor is applied either to the subject's back between the spine and scapula or applied to the subject's side along the mid-axillary line.

In operation, the system or device may grade all or a number of possible electrical resistivity arrays from the sensor and then choose which electrical resistivity array to use. In some variations the subset of electrical resistivity arrays are selected from the array after placing the sensor on the subject. The electrical resistivity arrays may be selected before applying current/sensing voltages for determining tissue wetness.

In some variations the scores may be ranked so that the electrical resistivity arrays that are likely to provide the highest quality signal may be chosen. Alternatively, in some variations the electrical resistivity arrays may be chosen on the fly, so that the score of an electrical resistivity array is determined just before using it; if it falls within the acceptable range (e.g., above/below the quality threshold) a measurement (or measurements) are taken before selecting the next electrical resistivity array to examine. The score may be stored with the results from that electrical resistivity array, for later analysis or consideration.

Thus, in general, for any given sensor of array size $m_{count}$, out of all of the possible electrical resistivity arrays on the sensor, the systems and devices described herein may select electrical resistivity arrays based on their error, location, and/or depth of investigation (DOI). Although in general all three of these criterion may be used (error, location, and DOI), in some variations only one or two these factors may be used for selection.

In general the sources of error can be attributed to the three right-hand terms in the equation below, i.e., k, ΔV and I. Each source of error has a threshold in which it cannot exceed if we were to select it. Each electrical resistivity array measures one apparent resistivity. For example, where ΔV is the voltage measured across P1 and P2, I is the current measured on C1 or C2 and k is the "geometric factor", a value that is derived by the electrode geometry, boundary of the body and spatial relationship between electrodes. As discussed above:

$$\rho_a = k \frac{\Delta V}{I}.$$

Errors may occur on the k, ΔV, and I.

For example, an error on k may occur by "mislaying" an electrode, since k is derived from the spacing of the four electrodes in relationship to each other. This means that although there are fixed distances between electrodes on the patch, the patch may be on a curved portion of the body (e.g., the back) or the subject's skin may be slightly wrinkled, and therefore the spacing between electrodes may not be as expected when applied to the subject. This may happen to some extent on any subject, so the systems, devices and methods may include a criteria to verify the k is fairly robust for small changes in spacing of the electrodes within an electrical resistivity array. To find out which electrical resistivity arrays have robust k, a "wiggle" test may be performed mathematically by varying the spacing of the four electrodes in relationship to each other by a one half electrode spacing in the calculations. If the calculated k values fall in a small range of values, it is considered robust; otherwise this electrical resistivity array may be rejected as being unstable or prone to changes with movement. The relative robustness of the electrical resistivity array may be provided with a numeric value that may be used in scoring the electrical resistivity array.

The range of k may be defined as $$\left| \frac{\delta k}{k} \right|.$$

An example of a wiggle test is provided below.

For any given electrical resistivity array, error may also be present in the voltage measurement, for example a typical voltage measurement may have a 1% to 4% error. Further, in some variations of the systems and devices described herein, a "noise floor" for measuring voltage is any voltage less than about 3 mV. Thus, electrical resistivity arrays may be chosen in which the predicted voltage is above this floor (e.g., 3 mV). In an exemplary sensor there may be many (e.g., thousands of) electrical resistivity arrays and a non-negligible percentage of these may have a predicted voltage less than 3 mV. In the equations below, we represent the error in voltage as $$\left| \frac{\delta U}{U} \right|.$$

An error may also be present in the current measurement. The term for current error in the equation below is $$\left| \frac{\delta I}{I} \right|.$$

The sign of the errors can be both positive and negative, so total allowable error is expressed as absolute value:

$$\left| \frac{\delta \rho_a}{\rho_a} \right| \leq \left| \frac{\delta k}{k} \right| + \left| \frac{\delta U}{U} \right| + \left| \frac{\delta I}{I} \right|$$

A threshold range may be provided based this error calculation. The threshold may be determined for each component (e.g., each type of error may be limited to be less than a threshold value, e.g., 5% absolute value for each), or the total error may be used. For example, if the three sources of error total to greater than 15% the electrical resistivity arrays may be rejected. The error criterion applied to determine a rank, score or grade for a particular electrical resistivity array may include each of these three categories of error, or just one or two of them. As mentioned, a threshold or weighting of these sources of error may be applied to each electrical resistivity array.

In addition to error, the location of an electrical resistivity array on the sensor and the median depth of investigation (DOI) may also be considered in determining if a particular electrical resistivity array may also be used.

Determination of the DOI is discussed and illustrated below, however, in general, electrical resistivity arrays in which the location and DOI are close to each other may be excluded, as using adjacent electrical resistivity arrays can confound the solution of the inverse problem by providing too much similar information. Thus, it may be desirable to space the shallow and mid-level electrical resistivity arrays out, but include all deep electrical resistivity arrays which typically are not as close to each other.

In one example, 252 Wenner-Schlumberger (W-S) electrical resistivity array were examined, and are listed in table 2 (FIG. 22), below. This table shows electrical resistivity arrays and lists (in the left column) the type of electrical resistivity array, as well as numbers indicating which of the electrodes correspond to C2, C2, P1 and P2. The right column indicates the calculated median depth of investigation (DOI). All of the electrical resistivity arrays in this table have a relative percent depth variance of less than 3% and a line charge K-factor that does not vary from the point-charge K-factor by more than 3%.

Median Depth of Investigation (DOI)

An electrical resistivity array may be a configuration of (typically) four electrodes used for measuring electric current and differential voltage. Common electrical resistivity arrays types include Wenner-Schlumberger, Dipole-Dipole and Gradient. Refer to FIG. 1B for illustrations of these types. Electrode electrical resistivity arrays have been used outside of the tissue wetness application described here to measure resistivity across both large and small distances, for example, ground water reservoir surveys in geophysics and wafer fabrication applications in semiconductor manufacturing use electrical resistivity arrays such as those shown in FIG. 1B. In FIG. 1B, the current is driven between C1 and C2 and voltage drop is measured across P1 and P2.

In some embodiments, a sensor contains between 28 and 32 electrodes ($m_{count}$ is between 28 and 32) providing thousands of combinations of four point electrical resistivity arrays. Each electrical resistivity array has a sensitivity pattern, where sensitivity in this context describes the degree to which a change in the resistivity in an area beneath the electrical resistivity array will influence the voltage measured between the sensing electrodes (P1 and P2). The cumulative sensitivity of multiple electrical resistivity arrays within the sensor produces the cumulative spatial sensitivity to the subsurface.

When the sensor is used as a subject-applied portion of an apparatus or system to detect the degree of wetness of the tissue, the sensor may be designed to maximize the number of electrical resistivity arrays that have a median depth of investigation (DOI) capable of penetrating to the depth of the tissue to be examined for hydration, but still provide robust responses. For example, with lung wetness, the sensor may be configured to have a DOI of roughly two inches, while still constraining the sensor so that the DOI is stable to small changes in electrode spacing and the measured signals should have a significantly high signal to noise ratio (e.g., noise is less than 5% of signal). Thus, the sensor should be configured so that there are sufficient "shallow" (e.g., closely spaced) electrical resistivity arrays to provided good coverage of the tissue around the region of interest.

Figure 21:
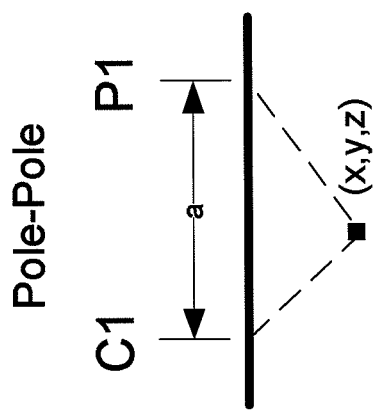
FIG. 21 illustrates a single pole-pole array.

The DOI can be determined for a four-point electrical resistivity array by first considering a single pole-pole array, as shown in FIG. 21. The change in potential, $\phi$, measured on P1 caused by a change in resistivity, $\delta\rho$, in a small volume below the surface located at (x,y,z) is determined by the following mathematical relationship (M. Loke and R. Barker, "Least-Squares Deconvolution of Apparent Resistivity Psuedosections," Goephysics, 60, pg. 1682-1690, (1995)):

$$\delta\phi = \frac{\delta\rho}{\rho^2} \int\int\int \nabla\phi \cdot \nabla\phi' d\tau.$$

Making use of this single pole-pole array, for simplicity, the potential, $\phi$, generated by the current source of magnitude, I, at C1 across a homogenous half-space is $$\phi = \frac{I\rho}{2\pi\sqrt{x^2 + y^2 + z^2}},$$

and similarly by treating P1 as a current source at some distance, a, its corresponding potential is $$\phi' = \frac{I\rho}{2\pi\sqrt{(x-a)^2 + y^2 + z^2}}.$$

Taking the gradient of $\phi$ and $\phi'$, the sensitivity function can be found explicitly in three dimensions as $$\frac{\delta\phi}{\delta\rho} = \frac{1}{4\pi^2}\int\int\int \frac{x(x-a)^2 + y^2 + z^2}{(x^2+y^2+z^2)^{3/2}((x-a)^2+y^2+z^2)^{3/2}} dxdydz.$$

The term inside the integral is known as the Frechet derivative, $$F_{3D}(x,y,z) = \frac{1}{4\pi^2}\frac{x(x-a)^2 + y^2 + z^2}{(x^2+y^2+z^2)^{3/2}((x-a)^2+y^2+z^2)^{3/2}},$$

and it defines the sensitivity for a pole-pole array (i.e., having a single drive electrode, C1, some distance, a, from the listening electrode, P1). Both electrodes are located on the x-y plane, where C1 is at the origin and P1 is displaced along x-direction a distance, a, the depth into the subsurface is given in terms of the z-coordinate.

The Frechect derivative provides a measure of the sensitivity in three dimensions, however, to estimate the depth of investigation confined to the z-direction, $F_{3D}$, is integrated along the x and y directions. The resulting integral has a simple analytical form (A. Roy and A. Apparao, "Depth of Investigation in Direct Current Methods," Geophysics, 36, pg. 943-959, (1971)):

$$F_{1D}(z) = \frac{2}{\pi}\frac{z}{(a^2+4z^2)^{3/2}}.$$

Integrating the above equation from zero to infinity gives the total sensitivity value of a pole-pole array along the z-direction, $$S_{pole} = \int_0^{+\infty} \frac{2}{\pi}\frac{z}{(a_{C1P1}^2+4z^2)^{3/2}} dz = \frac{1}{2\pi a_{C1P1}}.$$

To obtain the sensitivity for a four-point (or tetra-polar) electrical resistivity array, the contributions from the four electrodes can be written as the sum of four pole-pole arrays, $$S_{array} = \int_0^{+\infty} \frac{2}{\pi}\frac{z}{(a_{C1P1}^2+4z^2)^{3/2}} dz - \int_0^{+\infty} \frac{2}{\pi}\frac{z}{(a_{C1P2}^2+4z^2)^{3/2}} dz - \int_0^{+\infty} \frac{2}{\pi}\frac{z}{(a_{C2P1}^2+4z^2)^{3/2}} dz + \int_0^{+\infty} \frac{2}{\pi}\frac{z}{(a_{C2P2}^2+4z^2)^{3/2}} dz,$$

where $a_{C1P1}$ is the distance between electrodes C1 and P1, and likewise for $a_{C1P2}$, $a_{C2P1}$ and $a_{C2P2}$. However, the extent of the total sensitivity is infinite, what is needed is to find a finite depth at which the electrical resistivity array can sense a change in conductivity, otherwise known as the electrical resistivity array's depth of investigation.

A robust measure of depth of investigation is provided by the value at which the electrical resistivity array attains its median sensitivity value, i.e., where half of the sensitivity lies above and below this depth (Edwards L. S., 1977). It follows that the median depth of investigation, m, can be identified for any tetra-polar measurement by finding the upper limit, m, that satisfies the following equation:

$$\frac{S_{array}}{2} = \int_0^m \frac{2}{\pi} \frac{z}{(a_{C1P1}^2 + 4z^2)^{3/2}} dz - \int_0^m \frac{2}{\pi} \frac{z}{(a_{C1P2}^2 + 4z^2)^{3/2}} dz - \int_0^m \frac{2}{\pi} \frac{z}{(a_{C2P1}^2 + 4z^2)^{3/2}} dz + \int_0^m \frac{2}{\pi} \frac{z}{(a_{C2P2}^2 + 4z^2)^{3/2}} dz,$$

and which simplifies to finding, m, for the following algebraic equation:

$$\frac{1}{2a_{C1P1}} - \frac{1}{2a_{C1P2}} - \frac{1}{2a_{C2P1}} + \frac{1}{2a_{C2P2}} = \frac{1}{\sqrt{4m^2 + a_{C1P1}^2}} - \frac{1}{\sqrt{4m^2 + a_{C1P2}^2}} - \frac{1}{\sqrt{4m^2 + a_{C2P1}^2}} + \frac{1}{\sqrt{4m^2 + a_{C2P2}^2}}.$$

Once the depth of investigation is known for a general tetra-polar electrical resistivity array, the sensor can be designed as to maximize the number of electrical resistivity arrays that have a median depth of investigation capable of penetrating to some desired depth.

For example, consider a dipole-dipole array whose electrode coordinates are C1=16, C2=18, P1=19, P2=21, and hence, $a_{C1P1}$=3, $a_{C1P2}$=3, $a_{C2P1}$=5, $a_{C2P1}$=1 and $a_{C2P2}$=3. The depth of investigation as measured in electrode spaces is m=0.507, and to calculate a DOI in inches, the distance between the electrodes (0.36") is multiplied by m resulting approximately 0.18 inches. By carrying out the same procedure on a dipole-dipole array with coordinates C1=2, C2=4, P1=29, P2=31, its DOI is 2.42 inches.

The median depth of investigation must be stable to small changes in electrode spacing, in other words, the value of, m, should not change significantly when $a_{C1P1}$, $a_{C1P2}$, $a_{C2P1}$ and $a_{C2P2}$ are perturbed by some small amount. This exploration of stability can be done by prescribing some distribution for each term, $a_{C1Pj}$, with a predefine deviation (e.g., ½ electrode spacing) and solving for the resulting deviation, Δm. Arrays that have small deviations as compared to the value, m, are considered stable (e.g., Δm/m<5%). Those arrays that exceed the specified deviation tolerance are not used.

To test the robustness of the placement (a "wiggle" test of error in k), consider a depth of investigation calculated above for the two dipole-dipole arrays, where $m_1 \simeq 0.507$ for the first and $m_2$=6.736 for the second. For the sake of simplicity, we suppose the current drive electrodes remain stationary, but both listening electrode move together by ±½ electrode spacing (i.e., C1=16, C2=18, P1=19±½, P2=21±½ for the first and likewise for the second). The resulting change in the DOI are $\Delta m_1 \simeq [0.305, 0.677]$ and $\Delta m_2 \simeq [6.611, 6.862]$, and hence, their relative change are $\Delta m_1/m_1 \simeq 73\%$ and $\Delta m_2/m_2 \simeq 4\%$. This result shows that the first dipole-dipole array's DOI is susceptible to a half-electrode deviation.

In this particular example the electrodes are close together in the first dipole-dipole array so a half-electrode deviation is larger as compared to the same deviation of a second dipole-dipole array. However, the size of the deviation is not necessarily proportional to the electrode spacing. For example, consider the following array, C1=2, C2=12, P1=7, P2=25, which has an m≈6.435 and its deviation is Δm≈[0.733, 3.177]. Note that while this array's DOI is similar in depth to the second stable dipole-dipole array and its electrodes are not close together, there is a nearly nine fold increase between smallest and largest depth of investigation measure. This example shows the important of verifying the robustness of the DOI measure to small changes in the electrode position likely to be experienced in the field.

In the previous example, electrical resistivity arrays were selected based on their depth of investigation and its robustness to small changes in electrode position. However, as the depth of investigation increases, the voltage drop measured between P1 and P2 becomes smaller, so it may be necessary to verify that the resulting voltage drop can be measured accurately before selecting that electrical resistivity array. Therefore, a signal to noise level threshold may be included or used in addition. The SNR threshold may also be used as a selection criterion to identify these electrical resistivity arrays that will or will not be used. This SNR threshold may be established by considering two mathematical models for the size of the voltage drop across P1 and P2. The first model is based on point current sources, the second on a line-charge model and both suppose the current is injected into a homogeneous half-space. The voltage value, ϕ, some distance, r, away from a point source with magnitude, I, decays as $$\phi = \frac{I\rho}{2\pi r};$$

in a homogenous half-space with resistivity, ρ (Igel 2007, pg. 33-34). For the tetra-polar array, the voltage at P1 has the contribution for both the current sink at C1 some distance $r_{C1P1}$ and the current source at C2 some distance $r_{C2P1}$. By superposition and $I_{C1}=-I_{C2}$, the voltage at P1 is $$\phi_{P1} = \frac{I_{C1}\rho}{2\pi r} + \frac{I_{C2}\rho}{2\pi r} = \frac{I\rho}{2\pi}\left(\frac{1}{r_{C1P1}} - \frac{1}{r_{C2P1}}\right).$$

A similarly expression provides the voltage $\phi_2$ at P2 some distance $r_{C1P2}$ and $r_{C2P2}$ from C1 and C2, respectively. The voltage drop across P1 and P2 is given by $$\Delta\phi_{P1P2} = \phi_{P1} - \phi_{P2}$$

$$= \frac{I\rho}{2\pi}\left(\frac{1}{r_{C1P1}} - \frac{1}{r_{C2P1}} - \frac{1}{r_{C1P2}} + \frac{1}{r_{C2P2}}\right).$$

This expression captures the size of the signal, $\Delta\phi_{P1P2}$, given a tetra-polar point-electrode arrangement (i.e., C1, C2, P1, P2) and the product of the resistivity, ρ, of the homogenous medium and current, I. Moreover, note the connection between total sensitivity, $$S_{array} = \frac{1}{2\pi a_{C1P1}} - \frac{1}{2\pi a_{C2P1}} - \frac{1}{2\pi a_{C1P2}} + \frac{1}{2\pi a_{C2P2}},$$

and the voltage drop, $\Delta\phi_{P1P2}$, where $r_{C1Pj}$ plays the role of $a_{C1Pj}$. This implies that once the median depth of investigation is known, which uses the total sensitivity, the signal size is given by the product of the current, resistivity and total sensitivity (the reciprocal of total sensitivity is also known as the geometrical factor).

Using the same two dipole-dipole arrays (i.e., C1=16, C2=18, P1=19, P2=21 and C1=2, C2=4, P1=29, P2=31) and supposing the tetra-polar resistivity measurement was made using point-electrodes, the size of the voltage drops are $$\frac{4I_1\rho}{15\cdot\varepsilon\pi} \cong 0.928 \text{ V and}$$

$$\frac{4I_2\rho}{19575\cdot\varepsilon\pi} \cong 0.7 \text{ mV}$$

(i.e., supposing a 10 mA current, 10 Ωm resistivity and 0.0091 m electrode spacing). Thus, the voltage drop is approximately 1300 times smaller for the second dipole-dipole array, and a threshold must be used to guarantee the voltage signal is large enough to be accurately measured by the system. However, before establishing that threshold, the point-electrode model resulting in $\Delta\phi_{P_1P_2}$ will be expanded to an ellipsoidal electrode, as to predict the effects of the electrode's geometry on electrical resistivity arrays that are relatively close to each other.

As discussed above, electrodes cannot actually be points, as there has to be some dimension associated with the electrode and its area has to be suitably large to inject current into the body. Recall that FIG. 1C, discussed above, compares the voltage drop across P1 and P2 (ΔV) as measured by the instrumentation using rectangular electrodes (solid line) and the voltage drop predicted by the point-electrode model (dotted line). As is evident from FIG. 1C, when the electrodes are close to each other, the point-electrode model fails to correctly predict the voltage drop across P1-P2. The second ellipsoidal model was examined above in reference to FIG. 1D, showing that the second ellipsoidal electrode model achieves good agreement with experimental values.

For example, suppose that a measurement devise is capable of resolving 2 mV and a dipole-dipole arrays with an increasing gap between a fixed drive and listening electrode distances are used (refer to table 3). When the electrodes are very close (i.e., C1=2, C2=4, P1=5 and P2=7) the voltage drop is relatively a large 322 mV (assuming a 10 mA current, 10 Ωm resistivity and 0.0091 in electrode spacing), but when the listening electrodes are beyond electrode 23, the resulting voltage drop is too small to be measured accurately with a 2 mV resolution device, as illustrated in table 3:

TABLE 3

| C1 | C2 | P1 | P2 | ΔV |
|---|---|---|---|---|
| 2 | 4 | 5 | 7 | 322.2 |
| 2 | 4 | 7 | 9 | 86.3 |
| 2 | 4 | 9 | 11 | 35.2 |
| 2 | 4 | 11 | 13 | 17.5 |
| 2 | 4 | 13 | 15 | 9.8 |
| 2 | 4 | 15 | 17 | 6.1 |
| 2 | 4 | 17 | 19 | 4.0 |
| 2 | 4 | 19 | 21 | 2.8 |
| 2 | 4 | 21 | 23 | 2.0 |
| 2 | 4 | 23 | 25 | 1.5 |
| 2 | 4 | 25 | 27 | 1.1 |
| 2 | 4 | 27 | 29 | 0.9 |
| 2 | 4 | 29 | 31 | 0.7 |

Note that if we compare the size of the voltage drop of the line charge to that of the point electrode, the voltage size returned by both models agree when the spacing between the drive and listening electrode is sufficiently large. Recall that the point model returned a voltage drop of 0.7 mV (for C1=2, C2=4, P1=29, P31=7), which is equivalent to the line-charge model. However, when the electrodes are close to each other, the point electrode over estimates the voltage drop by nearly a factor of three (recall the point model returns 928 mV when C1=16, C2=18, P1=19, P2=21, which is a translated version of C1=2, C2=4, P1=5, P2=7).

Electrical Resistivity Array Selection

Figure 23:
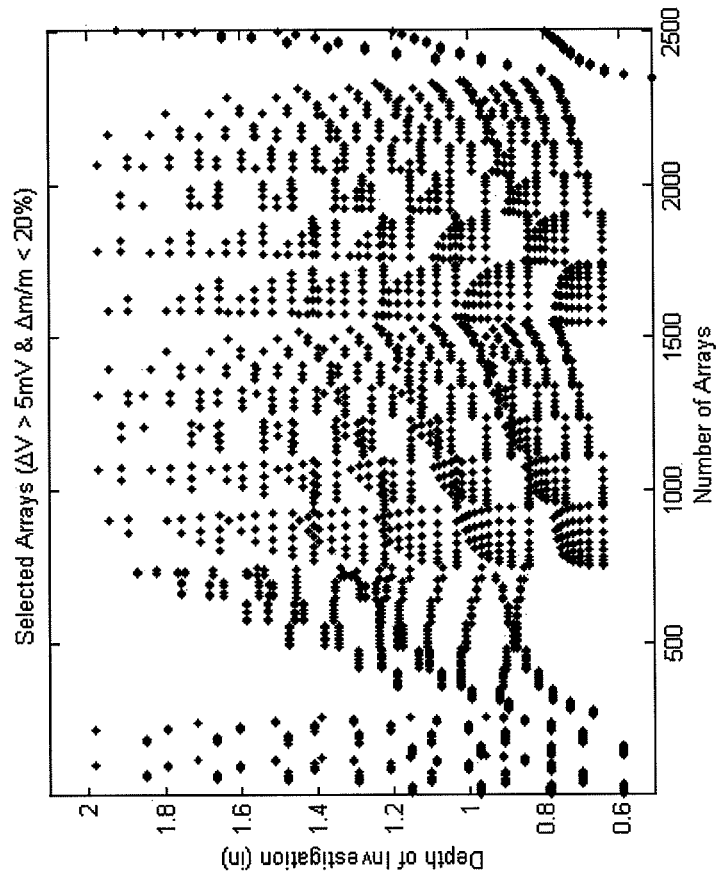
FIG. 23 illustrates a graph of the distribution of the number of sub-arrays versus the depth of investigation (DOI) for sub-arrays above the threshold of deviation of the depth of investigation ($\Delta m/m<20\%$) and threshold of voltage drop ($\Delta V>5$ mV).

There are various methods by which to select electrical resistivity arrays, for example in the previous three sections, the depth of investigation, m, its relative deviation, Δm/m, and its associated voltage size, ΔV, have been used to select arrays. Using a 31 electrode sensor in which the even electrodes drive current and the odd electrodes measure the voltage drop, there are $$\binom{16}{2} \times \binom{15}{2} = 12{,}600$$

possible combinations. Eliminating those combinations where both listening electrode are outside the drive electrodes, and ignoring the Gamma type arrays results in 5,460 arrays. Supposing the voltage drop should be larger than 5 mV and the relative deviation in the depth of investigation, Δm/m, less than 20%, there are some 2,500 arrays available (refer to FIG. 23).

However, in some variations, it might also be of interest to leave the Gamma type arrays in the selection set and instead threshold based on the relative deviation between the point voltage drop and its line-charge counterpart, and limiting the DOI deviation to less than 3%. In this case 777 arrays are selected and are explicitly listed in the table (table 2) in FIGS. 22A-J. The selection criteria can also be electrical resistivity array type dependent and chosen to return a uniform coverage across the domain by taking into account the electrical resistivity array's DOIs and listening electrode locations. Therefore once the DOI, its deviation and associated voltage drop is known, electrical resistivity arrays can be selected appropriately.

Exemplary Method of Discarding Electrical Resistivity Arrays Using Sensitivity and System Noise The median depth of investigation (DOI) may serve as a measure of the amount of sensitivity a particular tetra-polar electrical resistivity array has to resolve a change in the subsurface resistivity at some depth. This may be calculated by assuming that the resistivity array sits on a surface of infinite extent and calculating the change in the field lines as generated by the drive and listening electrode pairs as if they were both driving current into the subsurface. The change in the field lines, as measured by the Frechet derivative, changes in three dimensions. To restrict this measure as to account for only the depth component of the sensitivity of a tetra-polar array, the Frechet derivative may be integrated across the surface plane, thus only the component that changes with depth remains. This depth of investigation (DOI) associates a sensitivity number to each tetra-polar array, which can be used to rank electrical resistivity arrays in terms of sensitivity. A "good" sensor may be considered one that has sufficient resistivity arrays with different sensitivities as to map the subsurface.

The accuracy of the associated sensitivities used to rank drive pairs may be examined and/or confirmed. For example a first method to verity the sensitivity ranking involves examining the depth of investigation to confirm that it is robust (e.g., doesn't change much) for small misplacements of electrodes, which could be due to the sensor wrinkling or bending. This may be accomplished by comparing the change in the depth of investigation due to electrode misalignment, with the size of this sensitivity measure (akin to a signal to noise ratio). If the change in depth over the depth value is larger than some predefined tolerance for a resistivity array, then that array is may be ranked low, and/or rejected for use in reconstructing the subsurface, as it was deemed unstable. A second ranking confirmation may be derived when the voltage sensing electrode pair is far from the current driving pair, as this makes the signal susceptible to electronic noise. This may be determined by making repeated measurements to find a noise floor of the measurement for the system and using this noise floor as a threshold for the smallest voltage measurement allowed to be considered when calculating an array's apparent resistivity. By method such as these, the arrays may be ranked; one or more of these methods may be applied. This ranking may be include multiple parameters (e.g., thresholds) and one or more of these parameters may be as a threshold for accepting or rejecting the array in the measurement. For example, arrays that report voltages below the noise floor, and/or arrays having a depth of investigation that changes significantly (e.g., more than x, where x is 2%, 5%, 10%, 15%, 20%, etc.) with electrode misplacement may be deemed unstable and eliminated.

Thus, given a noise floor, n, an electrical resistibility array may be deemed stable if its voltage measurement is greater than this noise floor (e.g., $\Delta V > n$); alternatively or additionally, the array may be deemed stable if its depth of investigation, in, deviates by less than some threshold amount (e.g., $\Delta m/m < 5\%$), where $\Delta m$ is the change of depth as a function of electrode misplacement (as an example, approximately ½ electrode width in each direction). The remaining resistivity arrays may be considered stable and can be ranked by their depth of investigation and used in the inversion software to find the subsurface measure of interest, as discussed above.

Figure 24:
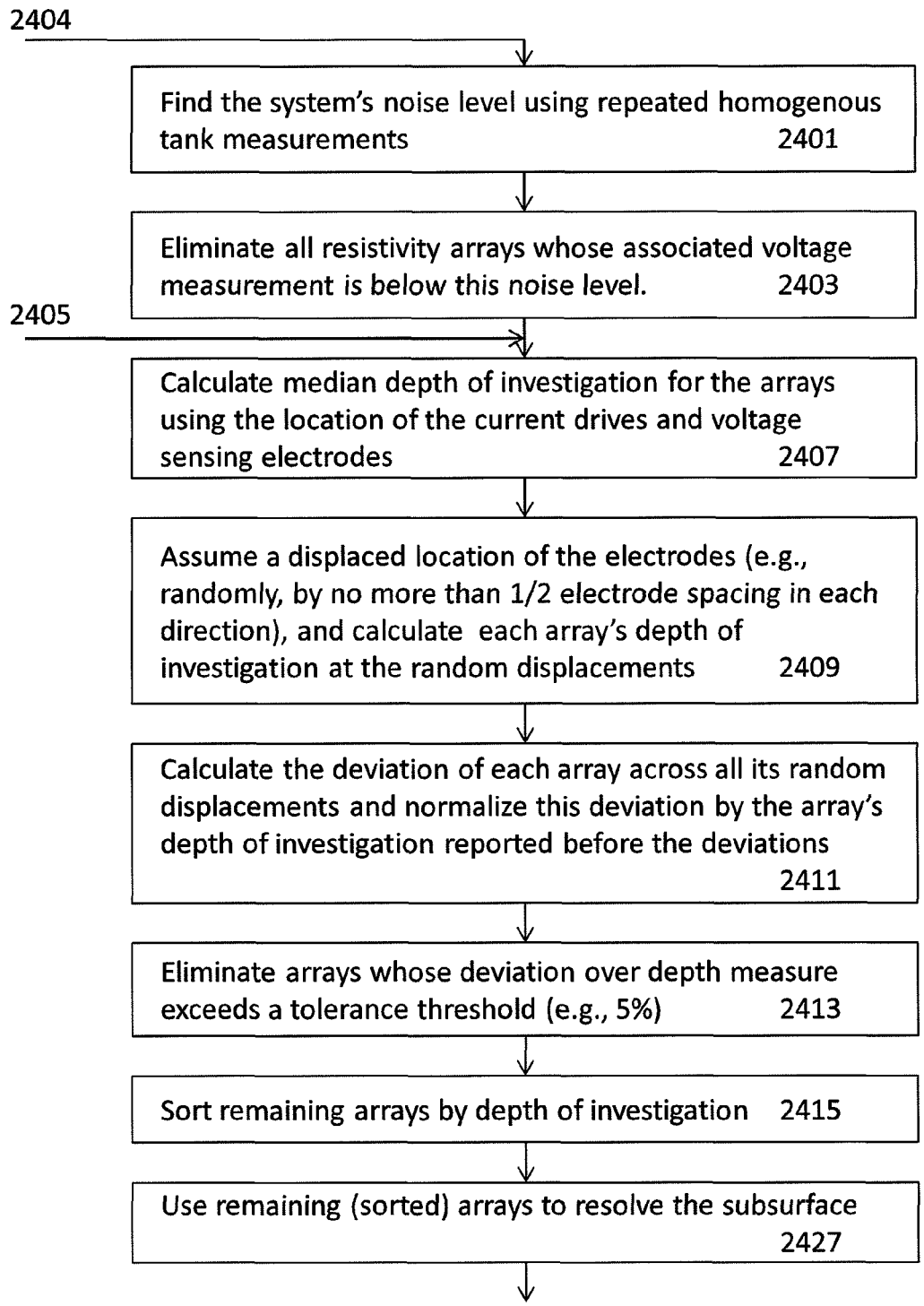
FIG. 24 illustrates one variation of a method of determining which arrays of electrodes to use from a sensor.

One variation of a method or system for determining which arrays to use from a sensor having a plurality of tetrapolar arrays is illustrated in FIG. 24. For example, in some variations, a system may be configured to first apply a noise level and classify arrays as above or below (or at) this noise level. For example, a system may first find the system's noise level using repeated homogenous tank measurements, as discussed herein 2401. Based on this noise level, the system may eliminate resistivity arrays whose associated voltage measurement is below this noise level 2403. Additionally 2404 or alternatively 2405 the system may calculate median depth of investigation for the arrays (or just for the remaining arrays after applying the noise level cutoff) using the location of the current drives and voltage sensing electrodes 2407.

The system may then calculate, by assuming a displaced location of the electrodes (randomly, by no more than ½ electrode spacing in each direction), each array's depth of investigation at the random displacements 2409. The system can then calculate the deviation of each array across all its random displacements and normalize this deviation by the array's depth of investigation reported before the deviation 2411. Any array whose deviation over depth measure exceeds some tolerance (e.g., 5%) may then be eliminated 2413. In some variations, the remaining arrays may then be sorted in teams of their depth of investigation 2415. Finally, the remaining arrays may be used to resolve the subsurface 2427 as described herein.

Any of the systems described herein may be implemented in a computer having a processor. For example, a system may include a processor configured to rank and/or eliminate the tetrapolar arrays.

In general, the sensor material and dimensions may be designed so that each electrode in the combined array (i.e. sensor) makes reliable mechanical and electrical contact to the subject's skin, where the skin curvature varies between subjects and varies with subject's position and movement.

Throughout the production of many prototypes and human subject testing, the inventors have discovered that a narrow and thin patch (sensor) makes the most reliable mechanical and electrical contact to a human subject over a range of subject motion. A thin and narrow patch was found to be less susceptible to buckling, and hence, provided better electrical contact. Excessive bucking in the patch can cause significant reduction in the spacing between the electrodes, thus changing the depth of investigation. A thin and narrow patch was also found to be more conformal to the curvature of the subject; reducing the stress, strain, tension on the hydrogel and reducing electrical impedance variability. An important finding in the development of the patch was that with the proper selection of hydrogel adhesive, the weight of the patch and it associated wire harness can be sustained on the subject's skin without the need of any additional adhesive.

As mentioned above, the support backing may comprise any appropriate material, including a polyester material and an anti-bacterial titanium oxide material (e.g., coating, etc.). Further, in some variations the patch is conformable to the contour of a subject's back and has a thickness of less than about 5 mils.

The patch length may be designed to satisfy the electrical resistivity array objectives with a constraint that the center of the patch, which has the deepest median depth of investigation, and typically should align to the region of interest. In embodiments where the lung is the region of interest, the center of the patch may be aligned with the lung, with the cranial edge of the patch extending to below the shoulder and the caudal edge of the patch extending to above the waist.

The surface dimensions of the electrodes are designed to source adequate current into the body between any two electrodes on the patch from a differential constant voltage source or differential constant current source. Adequate current may be considered the current necessary to achieve the desired signal to noise ratio in both current and voltage measurements, as measured in apparatus, for the expected conductivity of the human body. Thus, exemplary electrode dimension may be 0.15 inches by 2.00 inches.

The patch may be configured to be easily handled by the operator and positioned on the subject. A graphic layer could be printed on the patch to visually aid the operator to the proper orientation of the patch. Visual marking may include "towards head", "towards foot", "center", as mentioned above. Hydrogel may be sandwiched between the electrodes and a plastic release liner. The release liner would protect the hydrogel in storage and would easily be peeled away to expose the subject side of the hydro gel prior to application in the clinic. Tabs may be placed on the patch to handle and position the patch without interfering with the exposed hydrogel. All patch materials including the hydrogel may be biocompatible.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various examples and illustrations are provided herein, these examples are not intended to be, nor are they, limiting. Other variations, including variations in the types, shapes and sizes of electrical resistivity arrays and individual electrodes, as well as the systems described herein, are contemplated. Further, although the majority of the examples discussed above describe the use of these devices, systems and methods to determine lung wetness, many of these devices, systems and methods may be used or adapted for use to determine the wetness of other body regions, not limited to lung. Thus, these methods, devices and systems may be used to treat disorders other than those associated with lung wetness (such as congestive heart failure). For example, the methods, devices and systems may be used or adapted for use to detect and monitor lymphedema, for use during hip replacement, or for monitoring, detecting or helping treat compartment syndrome. The claims that follow may set forth the scope of the invention described herein.

Forward and Inverse Problems.

Figure 5:
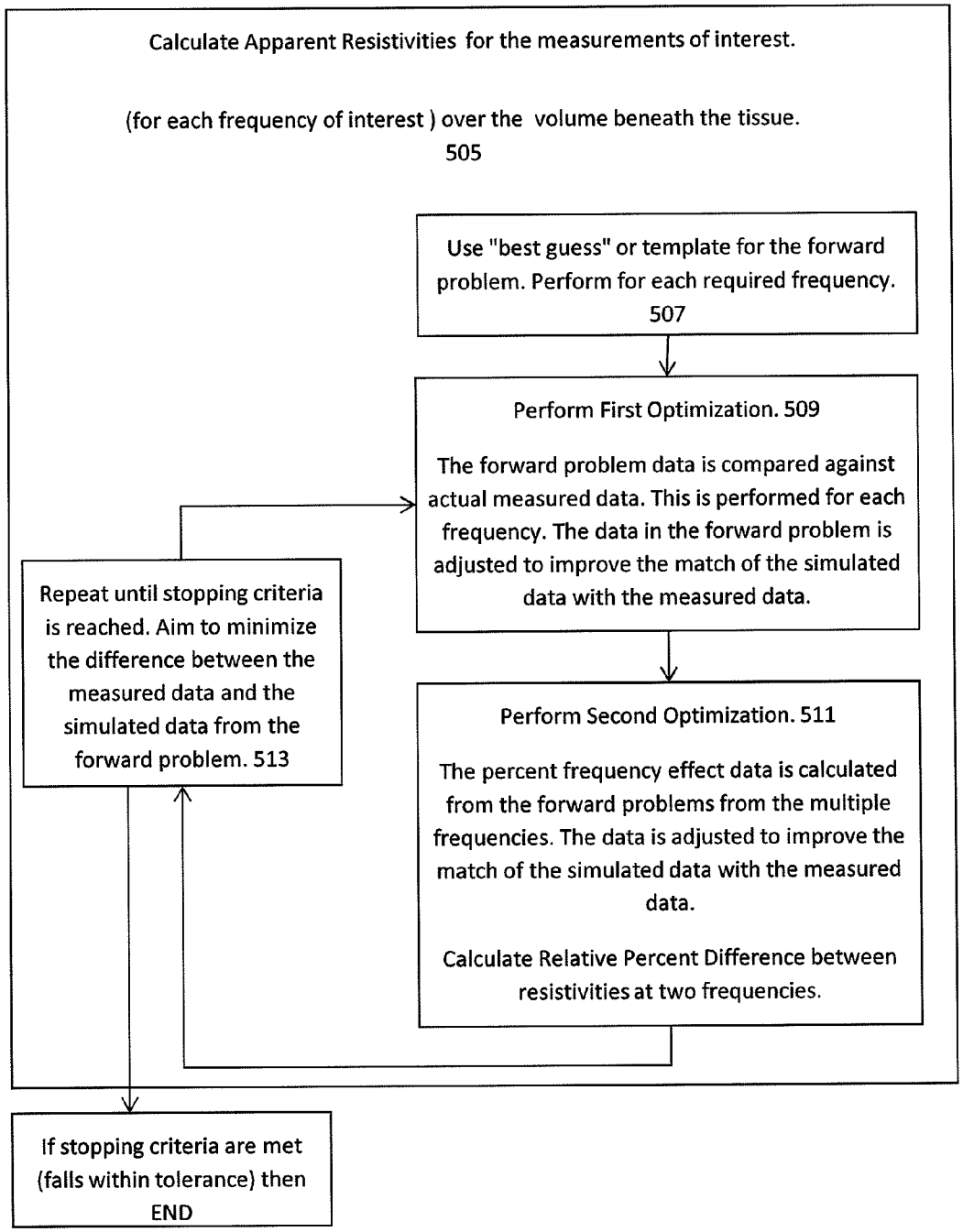
FIG. 5 is one example of a method of determining the spatial relationship of resistivities of a region of a body beneath an electrode array using the RSCSRAF.

FIG. 5 illustrates one method to determine a distribution of resistivities of a subsurface below a sensor, when the sensor is applied to a human body of unknown geometry. In FIG. 5, the processor, after receiving the applied currents and sensed voltages (complex) from the sensor of a predetermined configuration first calculates the apparent resistivities for each electrical resistivity array. The subsurface resistivities may be determined for each frequency of interest using a mathematical model of the sub-surfaces 505 (e.g., solving the forward problem).

A finite-difference or finite-element method may be used to model the subsurface and tie the spatial relationships of the resistivities and properties of resistivities of the subsurface to the measured apparent resistivities and properties of apparent resistivities from the measured values from the system. A quantitative approximation of depth may be derived for the model using the Frechet derivative or sensitivity function and is used to adjust the size of the blocks within the model. The "median depth of investigation" (DOI) may be used as a robust approximation to depth. The median depth of investigation is the depth in which from the sensitivity function, the depth above the DOI, has the same influence on the measured potential as the depths below the DOI.

Once the forward problem has been initially "solved," 507, 509 it may be optimized in conjunction with the inverse problem 511. In some variations, the methods and systems described herein run two optimization problems jointly, either consecutively or sequentially, to determine the spatial relationships of resistivities and properties of resistivities of the subsurface below a sensor on a human with unknown geometry. In this optimization problem, the initial model (forward problem result) is modified in a smoothness-constrained iterative manner 513 so that the difference between the model response (forward problem) and the observed data values (measured values from the system) is reduced to within acceptable limits.

This inverse problem is described in terms of an example as applied to one variation of the systems and methods described. For example, the inverse problem may infer the makeup of the body given a sample of voltage measures on the body's surface for a given current injection location. Because the set of data given to the inverse problem is far more limited, calculating the subsurface electrical properties from a few surface measurements cannot be calculated directly by plugging them into an equation. Thus, a set of "guesses" of the body's internal properties may be made and using the forward problem; each of their resultant voltages may be compared to the voltage measurements taken on the subject's body (an optimization process selects how to change the guesses). The forward model whose resultant voltages most closely resemble the measured voltage is selected as the most likely representation of the subject's internal properties.

In the first optimization, multiple apparent resistivity measurements taken with the sensor at one frequency serve as the observed or measured data. Reference geometry may be used to determine the geometric factors to calculate each apparent resistivity measurement. The reference geometry may be a rectangular volume approximation of the human thorax. The geometric factors can be empirically determined by using our system to measure each $(\Delta V)/I$ for each apparent resistivity position in the array when the sensor is placed just below the waterline of a saline tank with known resistivity and volume proportions similar to that of a human torso. Each geometric factor is determined by the following equation:

$$k = \frac{I * \rho_{saline}}{\Delta V}$$

The first optimization runs a set of forward problems, using a smoothness constraint to determine the spatial resistivities in the model such that the error in the model response to the measured values is minimized to within acceptable limits. This provides a spatial resistivity map at one frequency; however, an error has been introduced by the mismatch of the human geometry to that of the saline tank, which will be corrected by the methods described below.

The first optimization problem runs jointly (or separately) with a second optimization problem to seek a solution to the second optimization model in terms of the RPD or phase. Thus, in some variations the relative percent difference may be optimized within the process described in block 501 of FIG. 5. One or both may prove useful. There are two choices in setting up the second optimization problem; either to determine the spatial change in resistivities between two frequencies beneath the sensor or to determine the relationship of the phase of resistivities beneath the sensor. Either choice reduces the influence of the human geometry by the canceling out effect of the geometric factors.

Figure 6A:
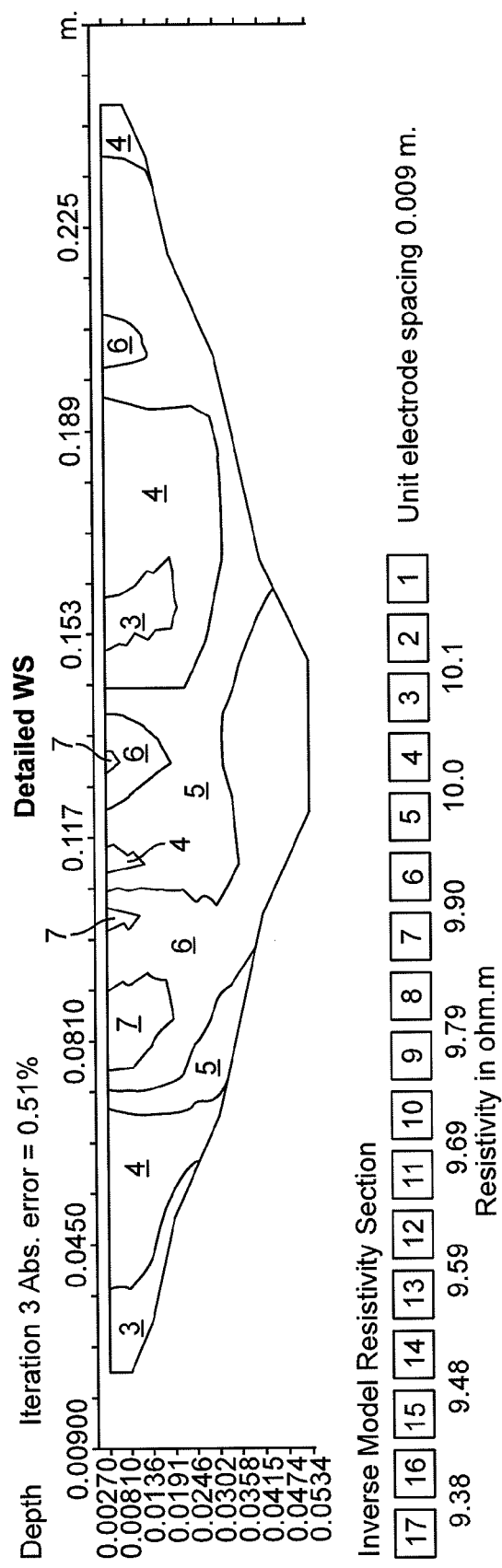
FIG. 6A shows a spatial map of resistivities in the control case, using a tank of saline.

In some variations, two images are produced, which may be depicted as "heat maps" showing relative intensity values. The first heat map image may be produced by the first optimization problem and shows the spatial resistivity mapping at a single frequency in terms of reference geometry. The mismatch between the reference geometry and the human geometry propagates an error in the solution. Yet, this image may contain some useful information because the reference geometry is of the general scale as a human. An example of this may be seen in FIGS. 6A and 7A, described below. The second image is produced by the solution from the second optimization problem. The second optimization problem is mathematically linked to the first optimization problem and therefore in some variations, may not be run on its own. The two optimization problems can be run jointly or sequentially. Examples of the second image are shown in FIGS. 6B and 7B.

The value in the second image lies in that the heat map produced is the RPD of the resistivities of the subsurface which has less influence from human geometry. In one application, e.g., the detection of lung wetness, we expect edema to present in the second image as either lower RPD values or as lower phase angles in the regions of interest; whichever method for the second optimization is chosen. It may be that two second images should be generated, one of the RPD type and one of the phase type. These two images together may provide more information about the subsurface.

Thus, for example, in one embodiment, when driving from 15 drive electrodes at each of four frequencies, a total of 252 times 4 (or 1008) measurements may be recorded and processed as indicated above. The measurements may be sorted by pseudo depth resulting in a triangular shaped profile sorted by spacing of the regions. Solving for the homogenous case, when all of the regions and sub-regions have approximately the same apparent resistivity (e.g., in a saline test bath), the k factors for this arrangement can be easily calculated. This is illustrated in FIGS. 6A and 6B, which shows a tank of saline to which the sensor has been placed in contact. For example, FIG. 6A shows an image representing the inverse model resistivities through a reconstructed pseudo-section from the tank filled with saline. The image in FIG. 6A is a resistivity image generated at 50 kHz. In a perfect system the image would be completely uniform (e.g., having a resistivity of 10 Ohm meters); in the experimental result shown in FIG. 6A, the values vary from approximately 9.77 to 10.31.

Figure 6B:
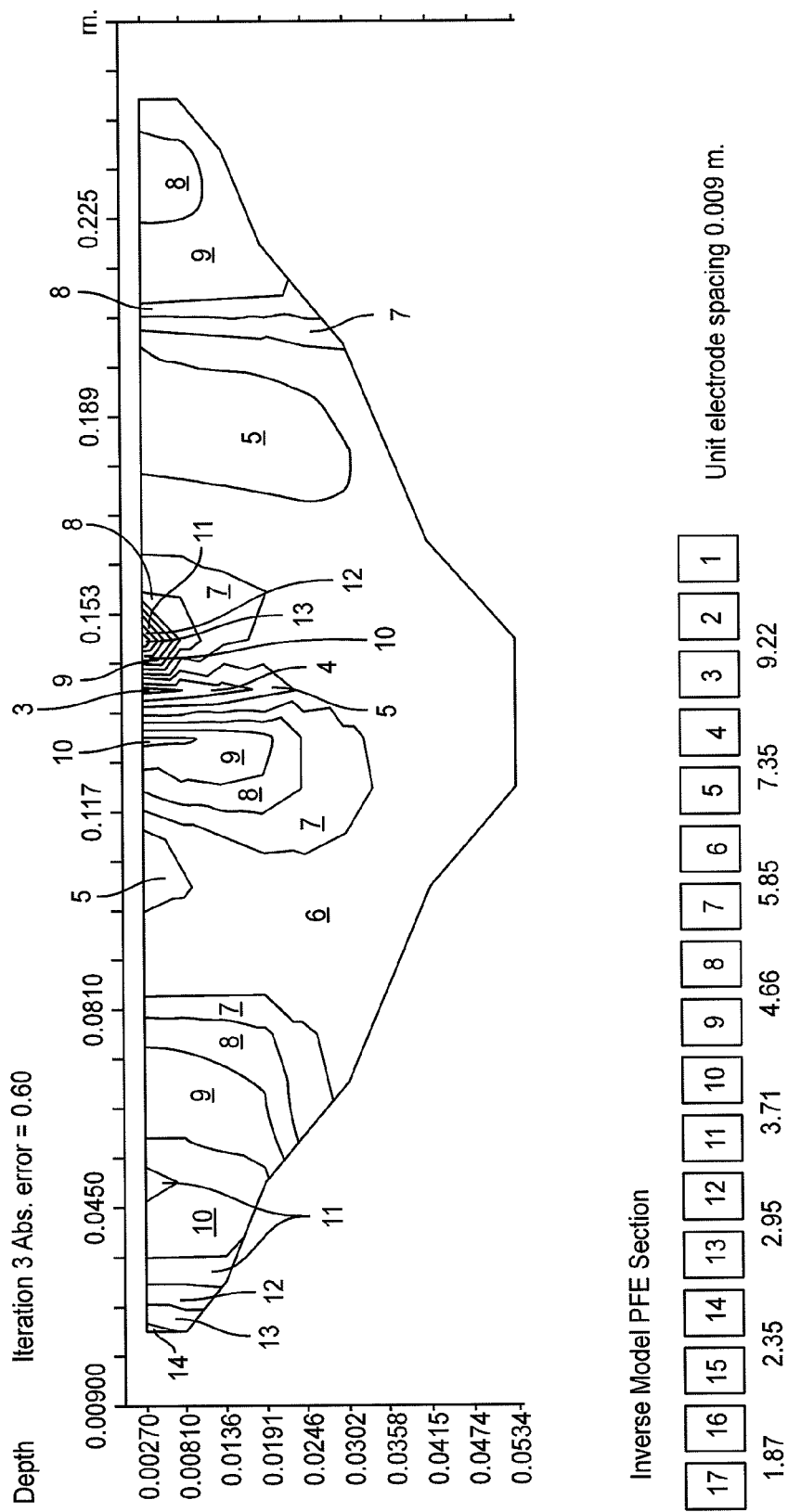
FIG. 6B shows a spatial map of RPD in the control case, using a tank of saline.

FIG. 6B shows a heat map of the same pseudo-section region of FIG. 6A, showing a RPD image of the frequency response between 50 k Hz and 200 kHz. As above, in an ideal system the values would be all zeroes; as shown, the values vary between 1.22 and 10.50 with the majority of the region being approximately 1.22.

Figure 7A:
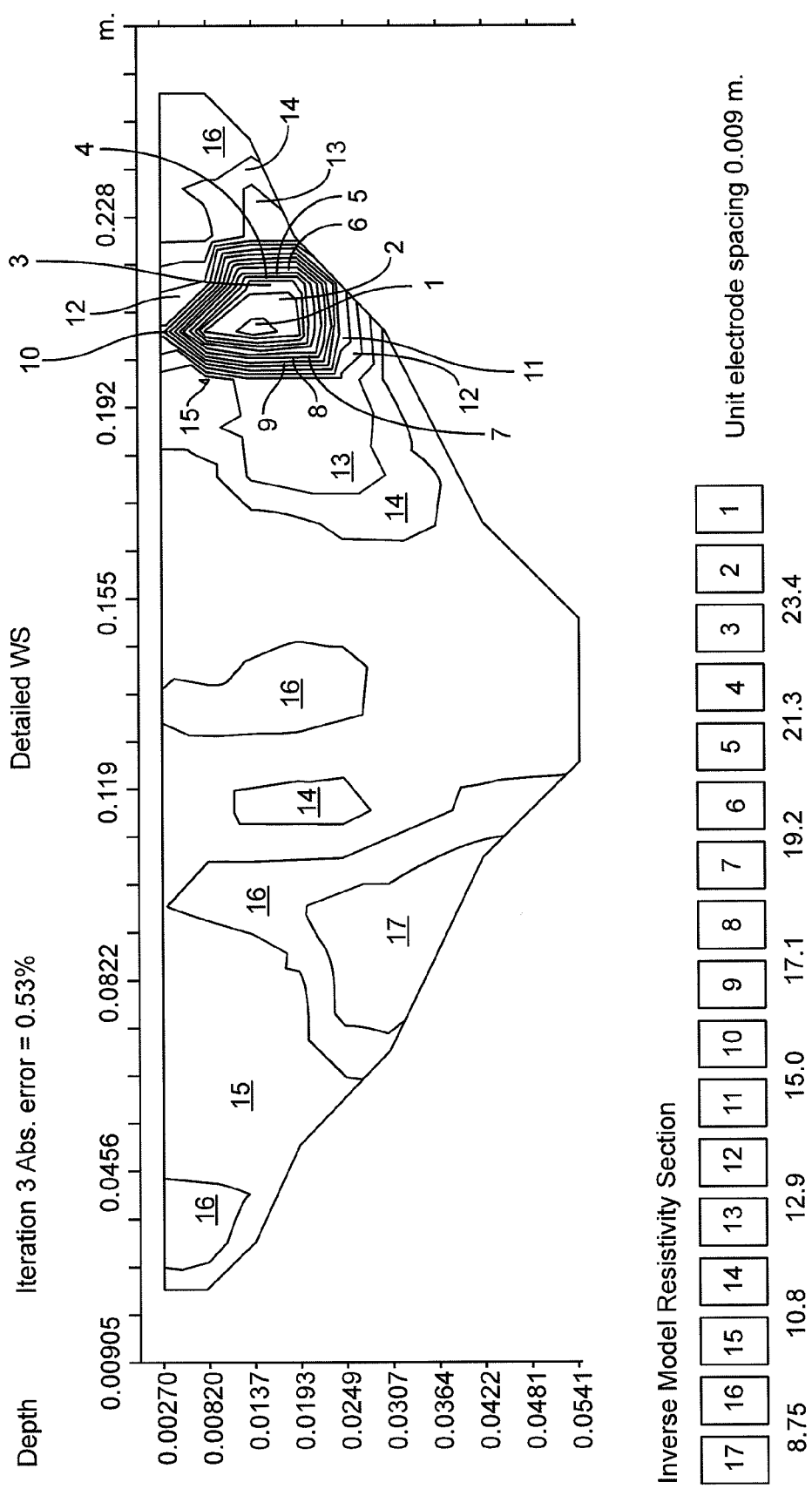
FIGS. 7A and 7B shows a spatial map of resistivities and RPD, respectively, of a test case using a test object held in a saline tank.
Figure 7B:
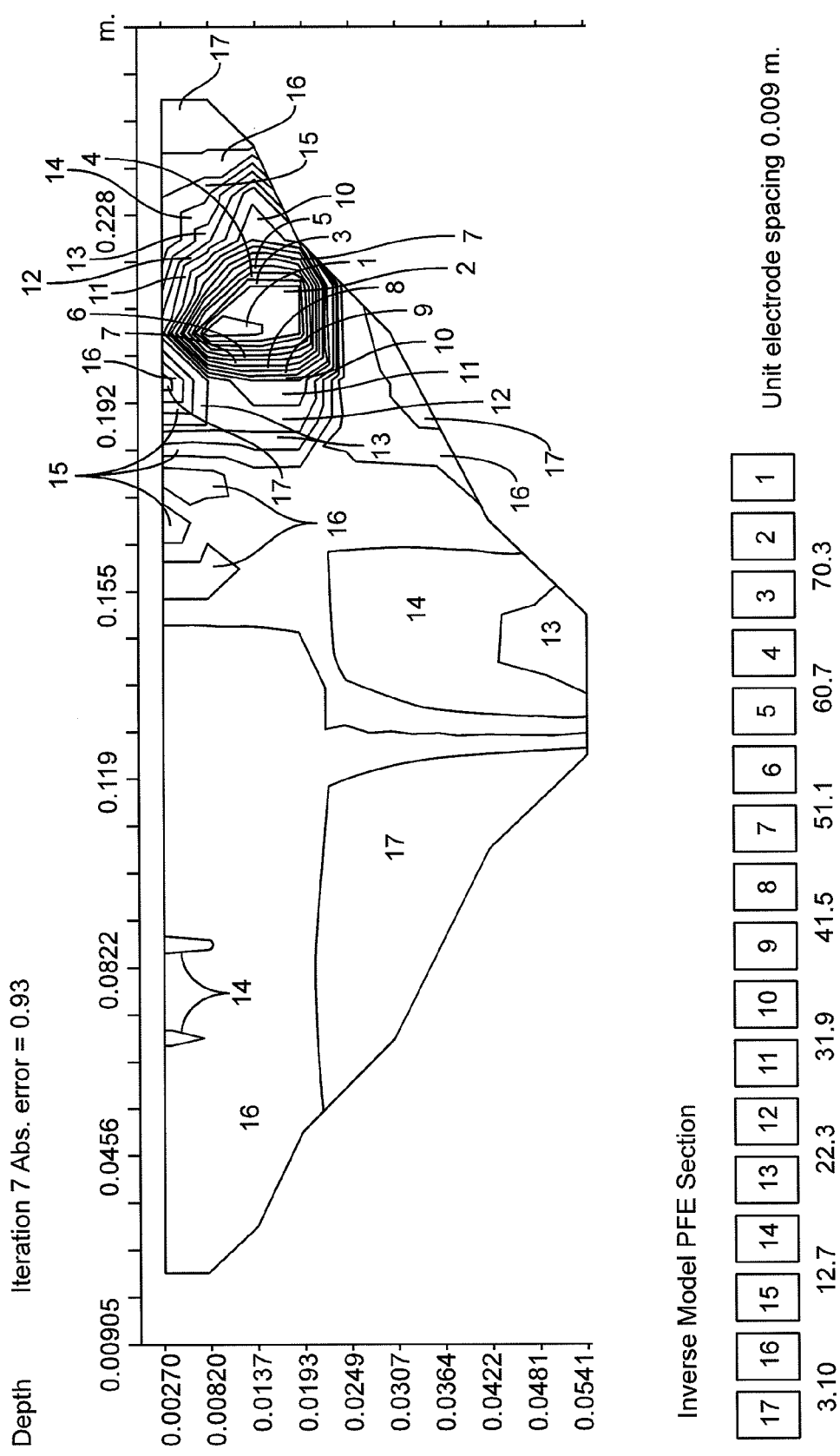

As a proof of principle of the method illustrated above, when an object, including biological material, is positioned beneath the sensor, the system may provide the distribution of resistivities. For example, the saline tank setup used for FIGS. 6A and 6B may be used as a proof of principle by adding various materials into the tank. FIGS. 7A and 7B illustrate one variation in which the sensor is used to determine the arrangement of resistivities of a test material (a yam) added to the saline tank. In this example, a yam has been added to the upper right side of the tank beneath the sensor, as can be seen in the images of FIGS. 7A and 7B. Similar to FIGS. 6A and 6B, the upper image (FIG. 7A) is a resistivity image from data taken at 50 kHz. The yam can clearly be identified in the upper right quadrant. The lower image (FIG. 7B) shows the RPD, the change in resistivity as a function of frequency between 50 kHz and 200 kHz. The saline has a low value of approximately 1.79 or less in the image. The yam value is in the 40's.

For example, taking multiple frequencies may allow the determination of high-contrast differences in resistivities. Experimentally data such as that shown in FIGS. 6A-7B illustrate that the system may be able to interpret differences between electrically conductive and insulative regions with high contrast. This is also illustrated in FIG. 8A-9B.

In determine the spacing of the electrodes for the array, which may affect the sensitivity of the resulting heat map, the spacing may be based on the sensitivity function (e.g., the Frechet derivative). The system may also change the cell (voxel) size and/or shape. In the figures illustrated here, the size/shape is assumed to be square; however other sizes and shapes may be used.

Figure 8A:
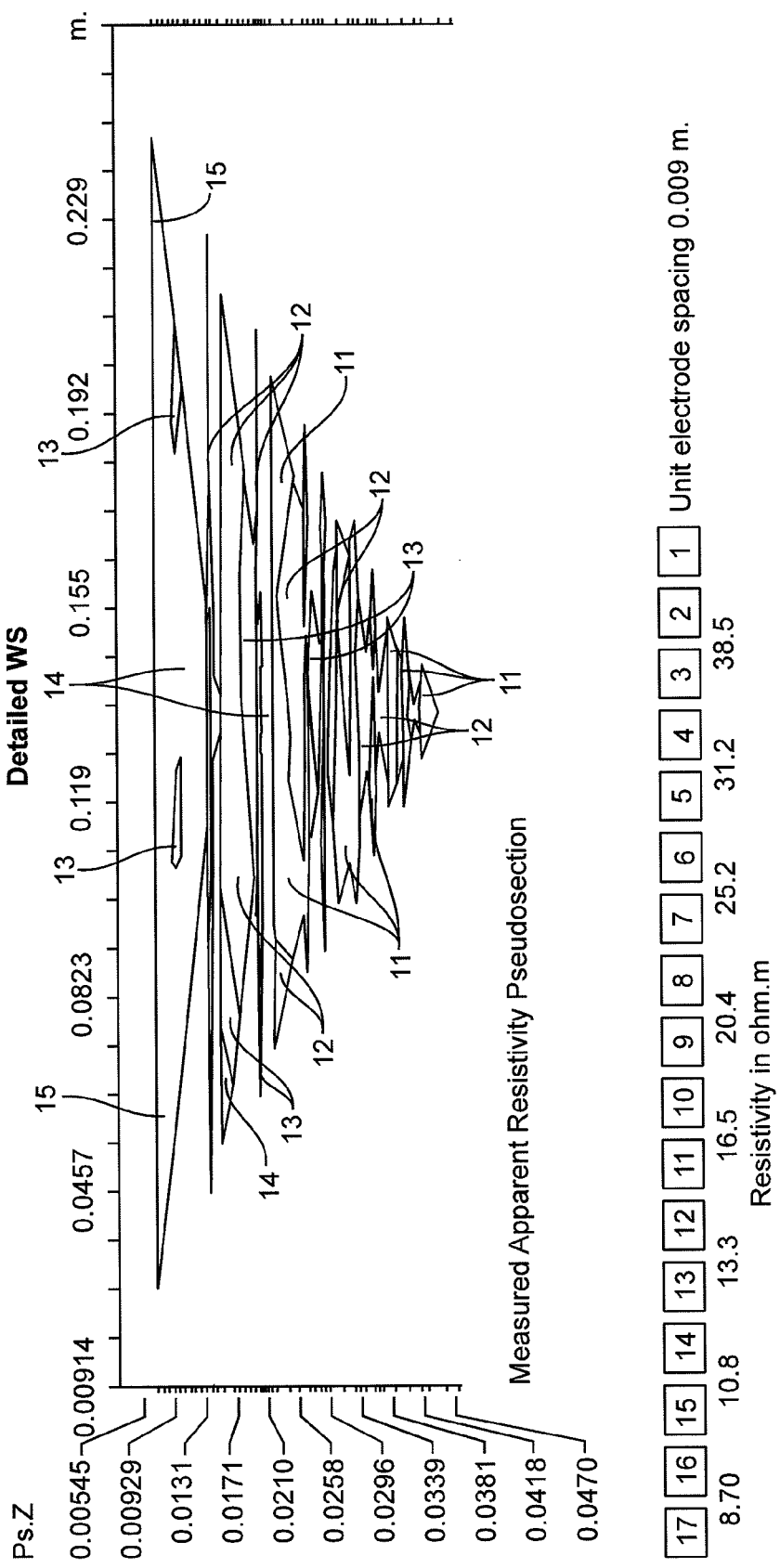
FIGS. 8A and 8B illustrate calculated apparent resistivity (FIG. 8A) in a pseudo-section beneath the electrode array used in a test tank containing a test object. This data is generated and used to solve the forward and inverse problem to generate a spatial map of resistivity as shown in FIG. 8C and the graphical representation of apparent resistivities illustrated in FIG. 8B. The resistivity map (in FIG. 8C) may be combined with a second map at a different frequency to produce a RPD map.
Figure 8B:
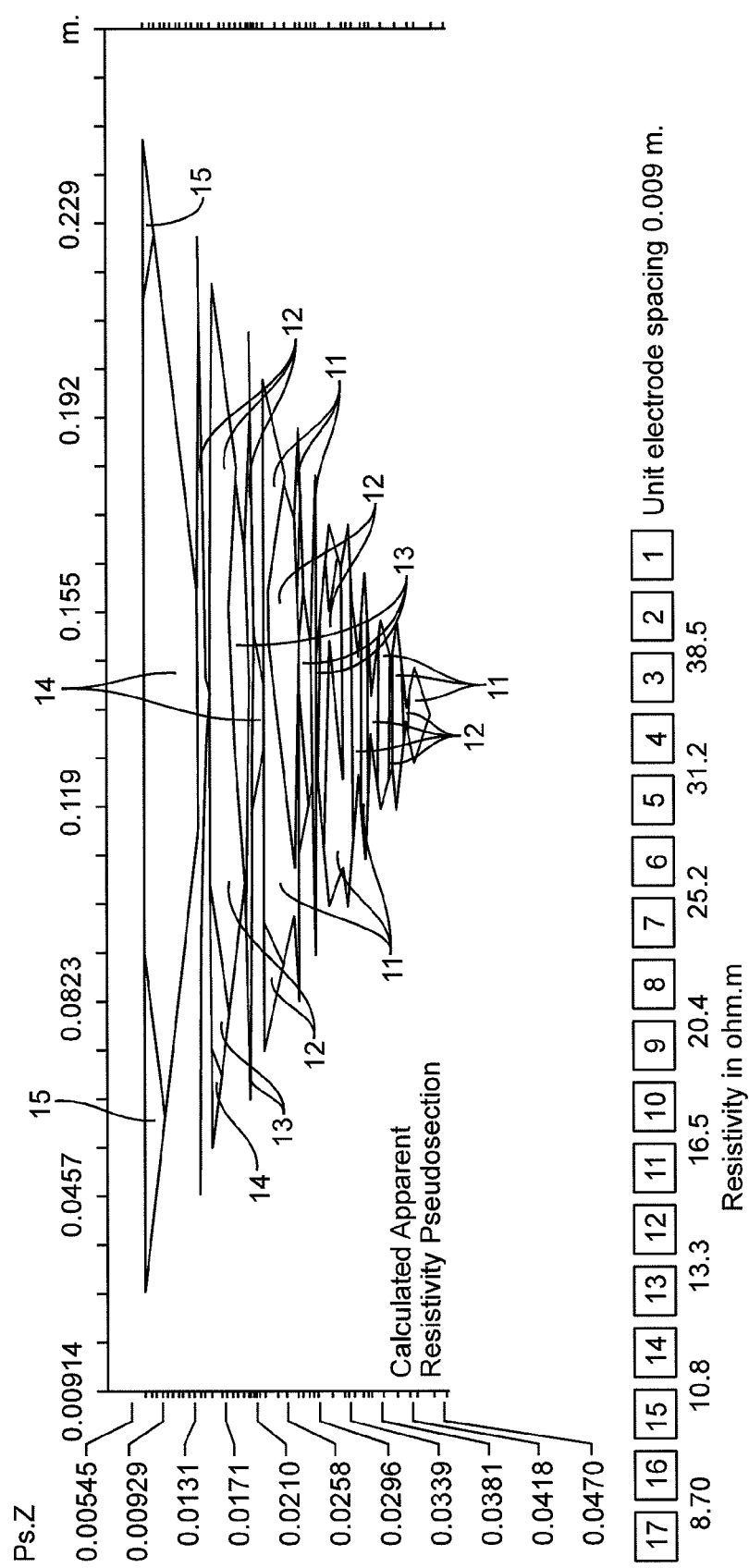

FIG. 8A illustrates apparent resistivities. In this example, the test object is a glass beaker. The data is generated and used to solve the forward and inverse problem to generate a spatial map of resistivities as illustrated in FIG. 8C.

Figure 9A:
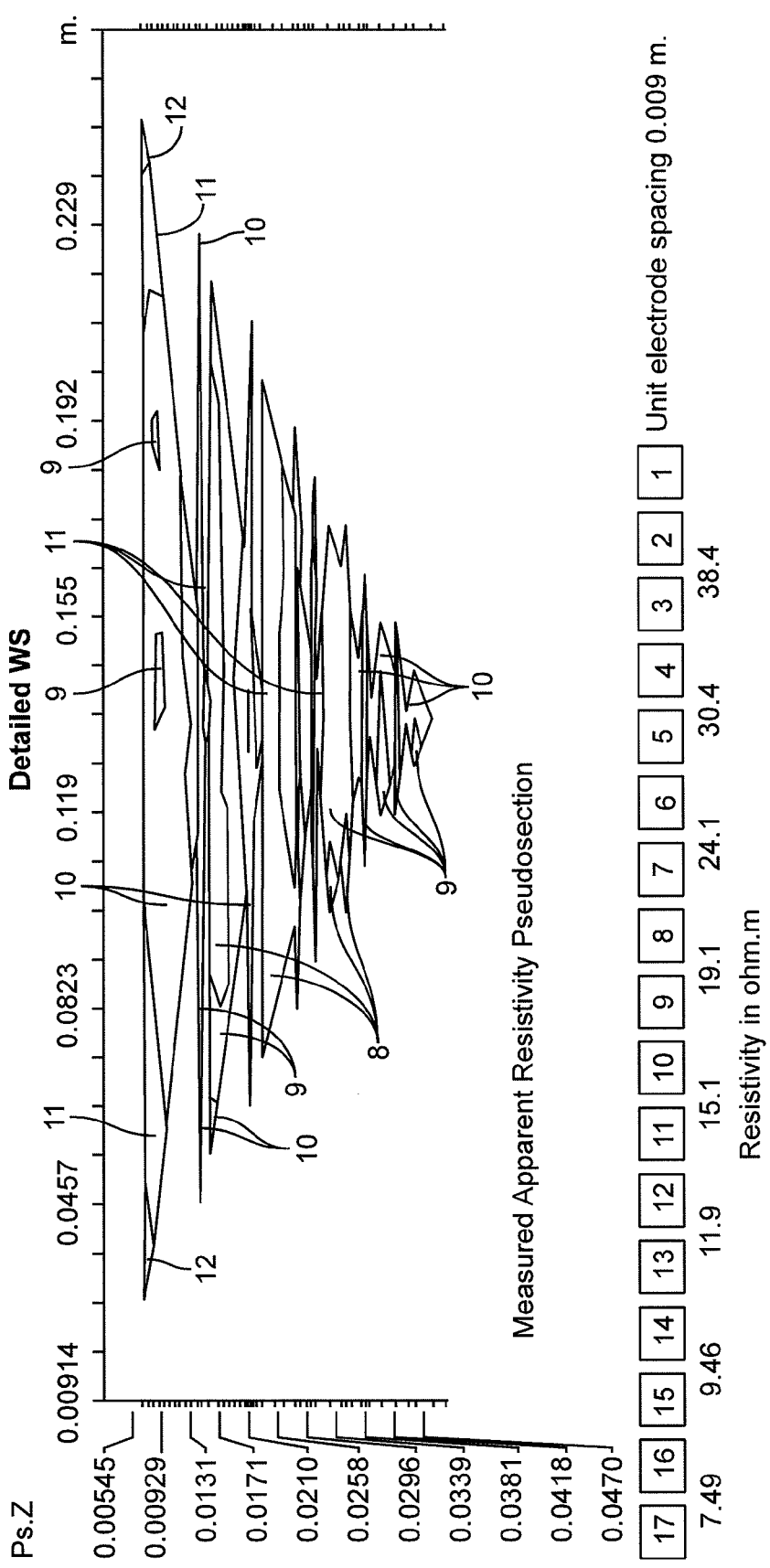
FIGS. 9A and 9B illustrate another calculated apparent resistivity (FIG. 9A) in a pseudo-section beneath the electrode array and RPD. The test object include the same test object of FIGS. 8A-8B but separated from the electrode array by a second (organic) test material.
Figure 9B:
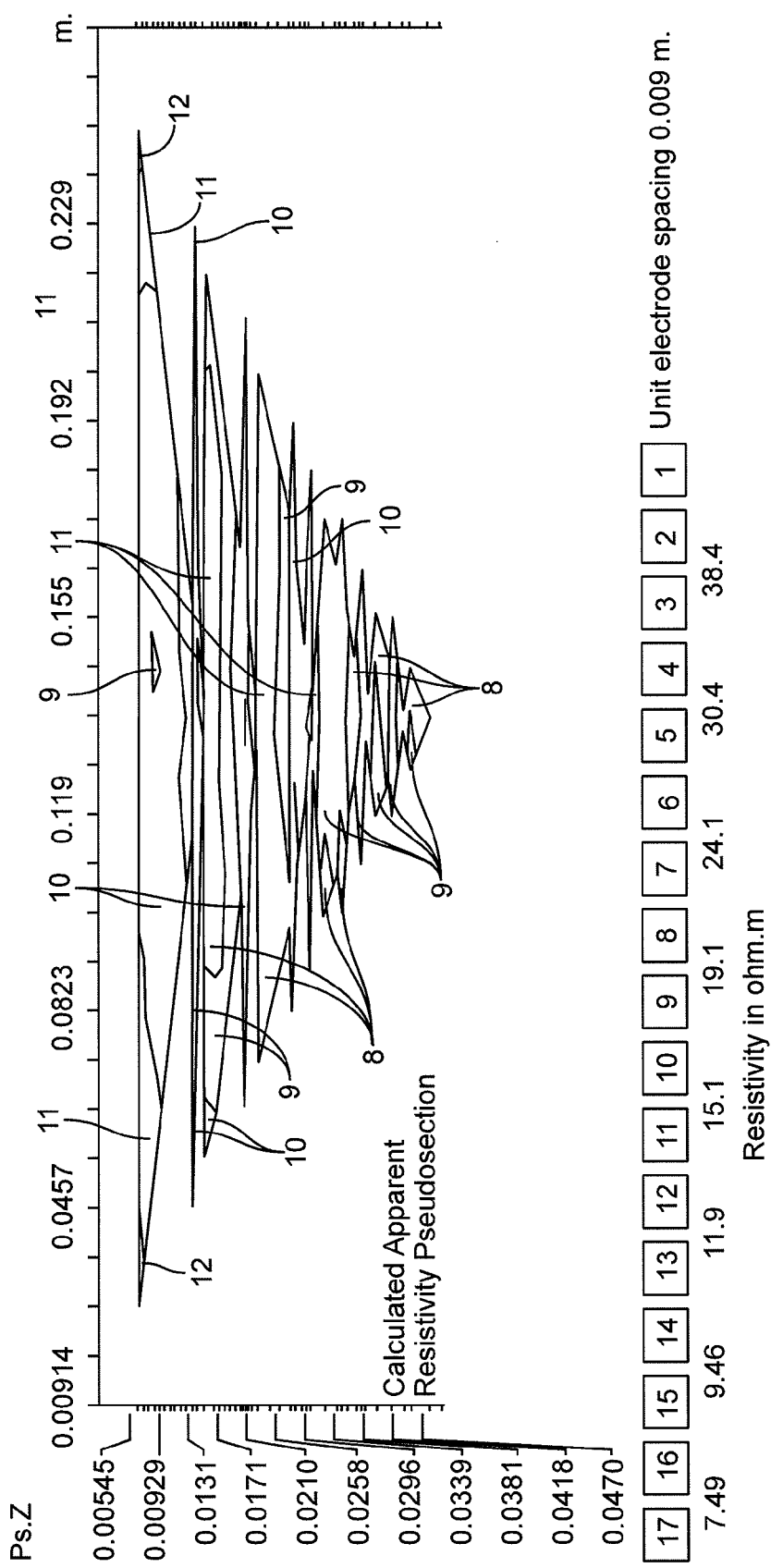
Figure 9C:
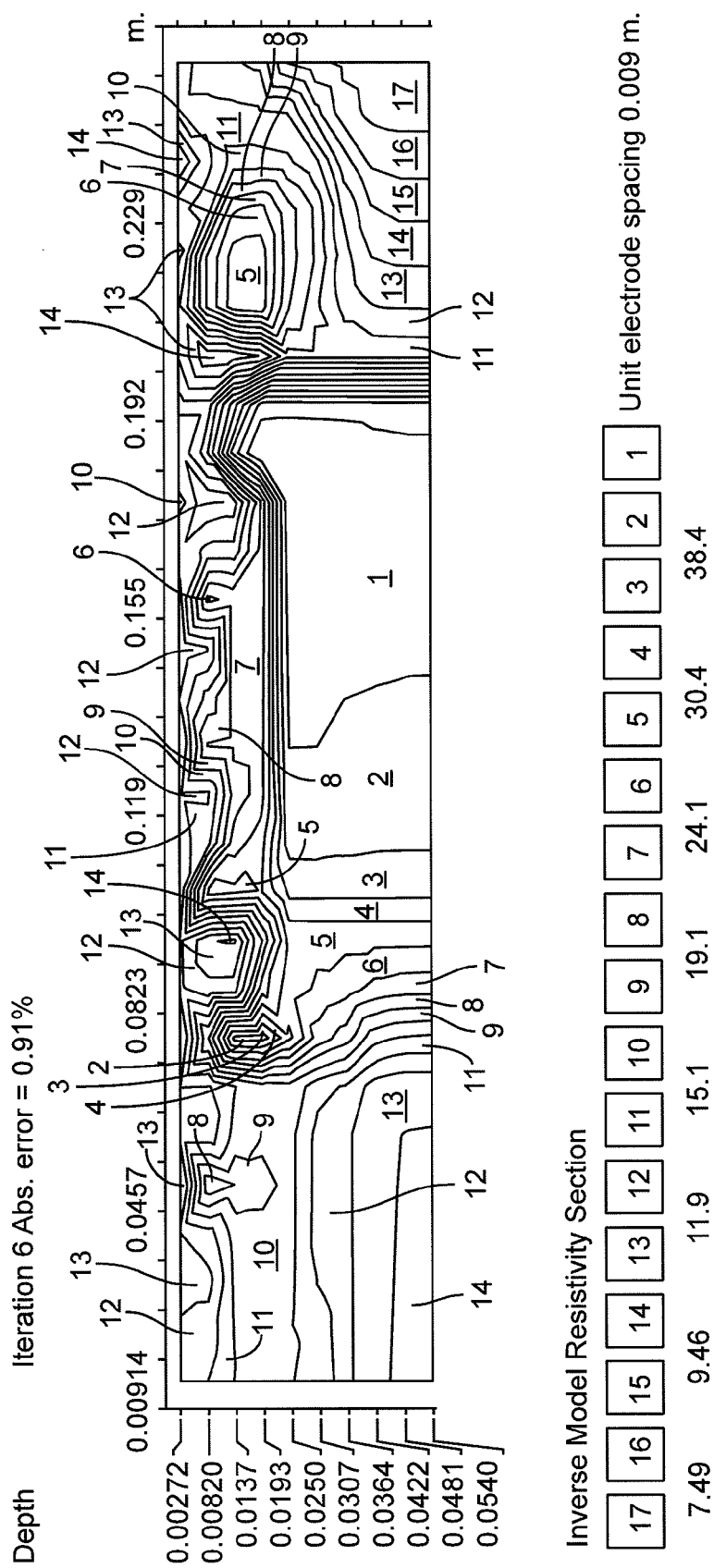
FIG. 9C shows a resistivity map similar to the map shown in FIG. 8C.

The same set-up may be used to image through a tissue similar to the tissue found in the subject's body (e.g., skin, muscle, bone) in order to image lung tissue. FIGS. 9A and 9B illustrate another example of computed spatial resistivity. The test object is the same beaker used in FIGS. 8A-8C, but also includes a second (organic) test material near the electrode surface. In this example, the second test material is muscle and bone (ribs) corresponding to (uncooked) pork tissue. As shown in FIG. 9C, the system was able to distinguish the flask (insulative material) beneath the layer of muscle and bone, based on resistivity of the different regions. When RPD is used to examine the bath, the beaker is not visible in the image as it has no frequency response.

The system may be adapted to apply a multi-frequency current (e.g., from a drive electrode) to a subject's skin and to sense voltage (from a sensing electrode) on the subject's skin at a plurality of frequencies. For example, the system can receive a multi-frequency current signal from a DAC, as described below, and, when the relay circuit is closed, apply a multi-frequency current to a subject's skin through the sensor. A current signal may be applied simultaneously to the subject at a plurality of different frequencies, or at only one frequency at a time (sequentially). When a relay circuit is open, the electrode interface can sense or measure voltage across the subject's skin at a plurality of frequencies. Simultaneously sensing voltage at multiple frequencies can be achieved by including a plurality of correlators in the system, where each correlator corresponds to a different frequency of measurement. Each correlator can act as a narrow band filter that allows the system to extract a complex voltage at a particular frequency of measurement. For example, one embodiment includes 20 correlators in the system corresponding to 20 different frequencies of measurement. Each correlator in the system can provide, as an output, a complex voltage having an in-phase component and a quadrature component for a particular frequency of measurement. It can be appreciated that the correlators can be implemented in a number of ways, as known in the art. In practice, a system may include only one correlator, or more than one.

In some variations the sensor may include active circuitry components that eliminate or reduce capacitance on the electrode interface. For example, when a multi-frequency current is applied to the electrode surface, an input capacitance can result at the electrode surface. To neutralize this capacitance, a capacitance neutralization circuit can be implemented. The capacitance neutralization circuit can feed the input capacitance back into an input of the electrode interface to effectively eliminate the input capacitance from the interface. The operation of a relay circuit, as described above, can also add a capacitance to the electrode interface. The capacitive effect of the relay circuit can be neutralized by adding an electrostatic shield around the relay circuit and driving the electrostatic shield when the relay circuit is closed.

Thus, in some variations the sensor may include active circuitry to enhance collection and processing of data. In other variations the processing of collected and/or applied signals may be done by the controller upstream from the sensor. By placing the active circuitry near to the electrode surface, the system can apply a multi-frequency signal to a subject, sense voltage on the subject, process the voltage to extract a complex voltage at each of the measured frequencies, and output the signals for further processing and analysis. It should be appreciated that the application of current, sensing of voltage, and data processing may all be done by the active circuitry on the sensor. Placing the active circuitry near the electrode surface may also reduce the capacitance at the electrode surface and minimizing the amount of any additional noise added to the applied and measured signals. Thus, the system of the present invention may eliminate excess capacitance and noise allows accurate measurement of the biological parameters of a subject, instead of measuring the effects of the electrode interface itself and noise.

Figure 10:
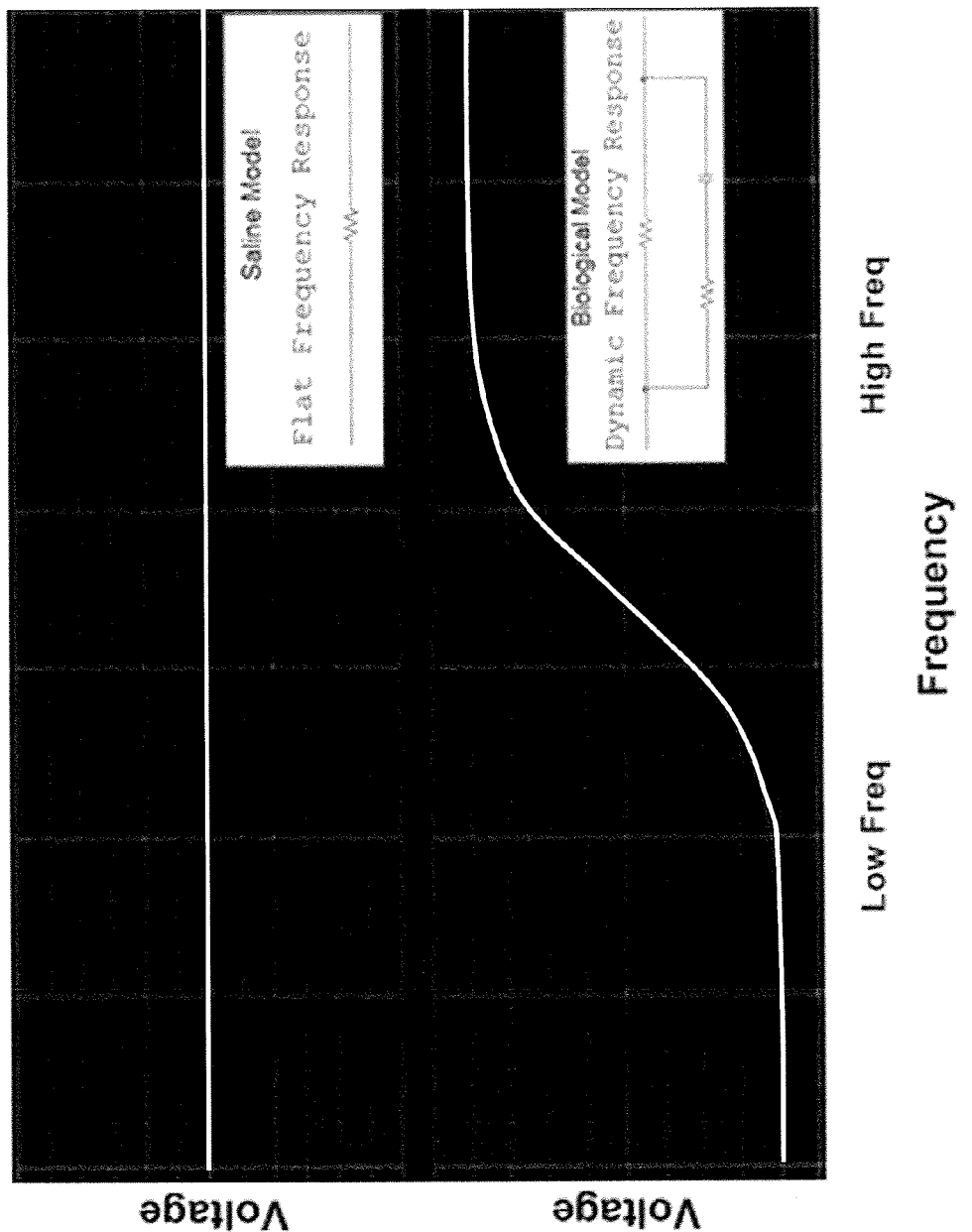
FIG. 10 illustrates the frequency response of water (top trace) compared to a biological material (bottom trace) from low to high frequencies of applied current.

Water, as opposed to most biological materials such as tissue, can be modeled electrically as nearly purely resistive, and has a relatively flat frequency response, as shown in the top of FIG. 10. By comparison, biological tissue has a dynamic frequency response, and may be modeled as an RC circuit, as shown in the bottom of FIG. 10. In FIG. 10, it is generally true that as frequency increases from low (e.g., <100 Hz) to high (e.g., <100 Hz), the frequency response of biological tissue increases, while the frequency response of water remains constant. Thus, it may be expected that when looking at lung wetness, the more that the frequency response of the sampled region behaves like water (e.g., has a relatively flatter frequency response) the more wetter that the region may be. Although this is a very simplified model, the use of the relative percent difference may take advantage of this simple relationship by comparing the apparent resistivities at low frequency versus high frequency. Wetter tissues may be expected to have a flatter frequency response, which may be seen by examining the relative percent differences between apparent resistivities at low versus high test frequencies.

In the examples described herein, the range of low frequency applied is approximately 80 kHz or less (e.g., 50 kHz or less, 30 kHz or less, than 20 kHz or less, 10 kHz or less, etc.). For example, 20 kHz is used in the examples shown in FIGS. 16A and 16B, described below. The high frequency range is typically about 100 kHz or greater (e.g., 200 kHz or more, etc.).

Figure 11:
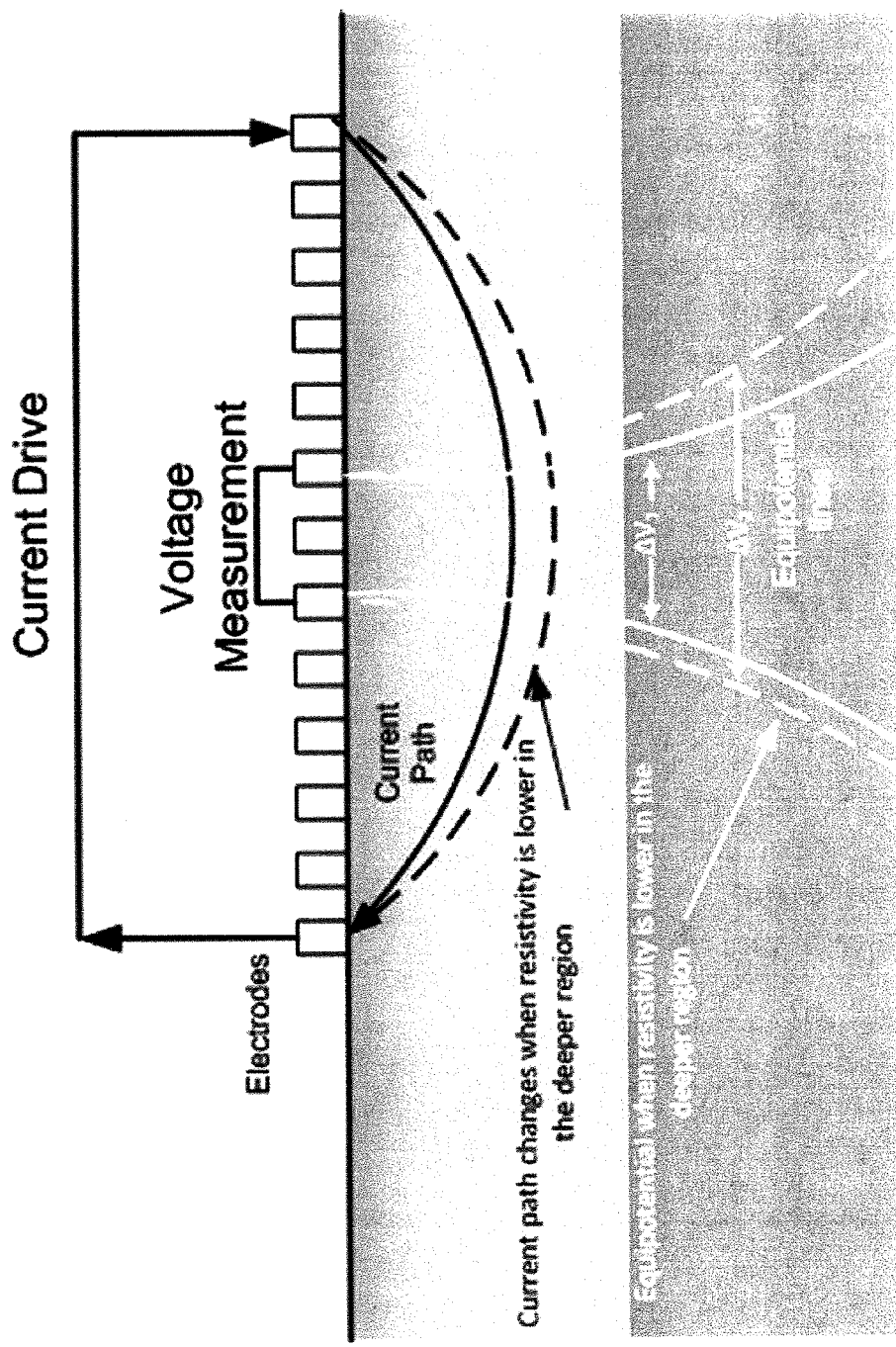
FIG. 11 illustrates a theoretical model showing the distribution of equipotential lines and current paths for an exemplary patch electrode on a surface having varying resistivities with depth. The amount of current used to make the measurements is imperceptible to the subject/patient.
Figure 12:
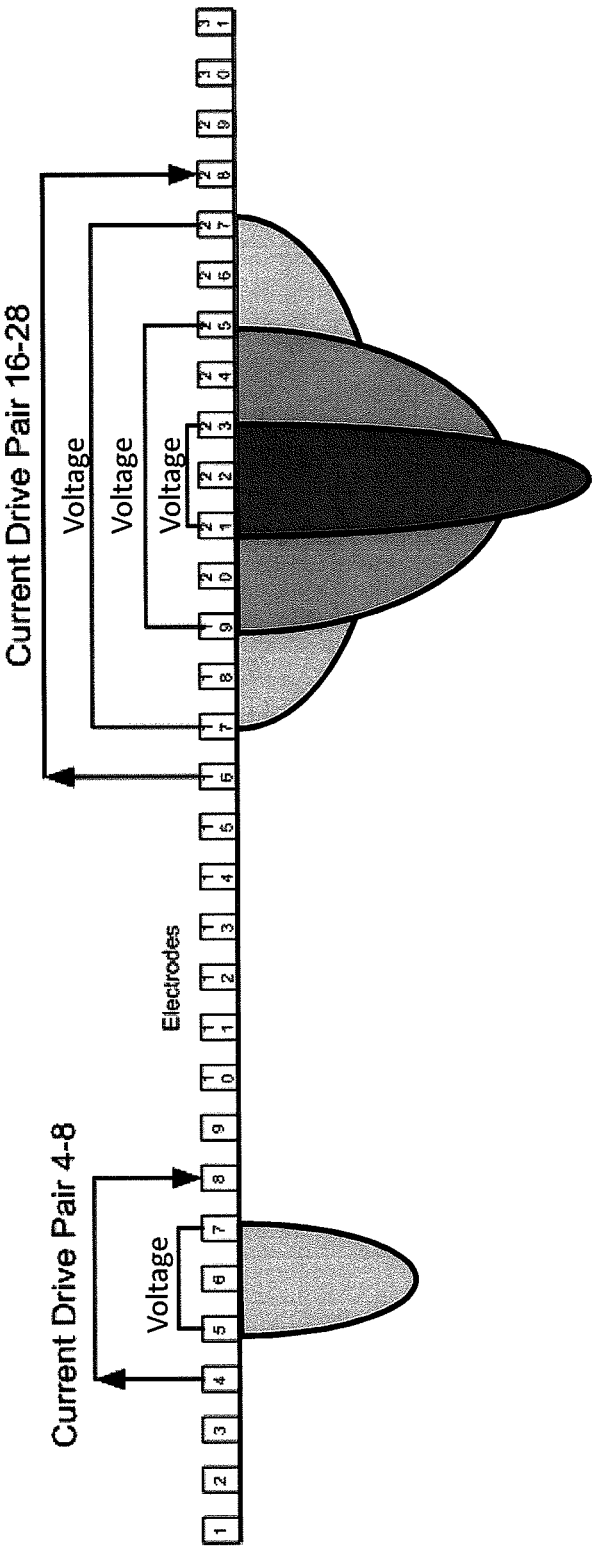
FIG. 12 schematically illustrates one variation of a method for applying a drive current and detecting (sensing) voltages to detect resistivities at different depths. In this example there are approximately 100 current drive pairs (current-injecting) and 250 voltage sensing measurements. By combining shallow and deep sensitivity measurements we can infer depth of objects. Shallow sensitivity may be achieved when voltages are measured close to the current drive pairs. Deep sensitivity may be achieved when voltages are measured away from the current drive electrodes. Approximately 100 current-injecting pairs and 250 voltage sensing measurements are used in this example. By combining shallow and deep sensitivity measurements, the depth of objects can be inferred.

FIG. 11 illustrates an example of an electrical resistivity array positioned over tissue to examine apparent resistivities indicating different tissue regions. In FIG. 11, the surface of the body includes an array of electrodes arranged so that the current is driven between outer electrodes and voltage is measured across pairs of inner electrodes. The current path between the drive electrodes changes from the solid line current path to the dashed line current path when resistivity is lower in deeper regions of the body. Similarly, the orthogonal equipotential lines between pairs of sensing electrodes separate further (larger delta-V) when the resistivity is lower in the deeper regions. Thus, changes in resistivity in the region beneath the tissue at various depths may be detected as changes in the voltage measured at various sensing pairs. On this basis, given a known array configuration, known applied current and measured voltages, the system may be optimized to solve for the resistivities in various depths beneath the electrodes. The depth that can be detected may depend on the arrangement of the electrodes on the surface, as illustrated in FIG. 12.

For the systems and methods to determine lung wetness as described herein, it is particularly of interest that the applied current and detected voltage allows sensing at sufficient depth to reach the lung. Thus, the application of the electrodes in the appropriate position is important, as is the manner in which the drive currents and sense voltages are applied and received. For example, in FIG. 12, an exemplary device having 31 electrdoes (drive electrodes alternating with sensing electrodes) is used to illustrate the depth sensitivity that can be achieved depending on the arrangement of the drive and sensing pairs. The combination of both shallow and deep measurements may therefore allow a reconstruction of the distribution of the spatial arrangement of resistivities. In the examples provided herein, voltage is measured between drive electrodes, and the combinations of drive and sensing electrodes may be varied to achieve some spatial arrangement shown in the figures (e.g., FIGS. 16A and 16B). For ease in the examples, the voltages are sensed from the odd numbered electrodes (e.g., FIG. 12) while current is driven from the even electrodes. For example, in FIG. 16, 252 electrical resistivity arrays where used. Although we describe the use of driving electrodes and driving currents herein, it should be apparent that the applied current may also be measured. For example, the current may be measured across a region in-line with the electrode (e.g., through the electrode). The complex current may be measured.

Figure 13:
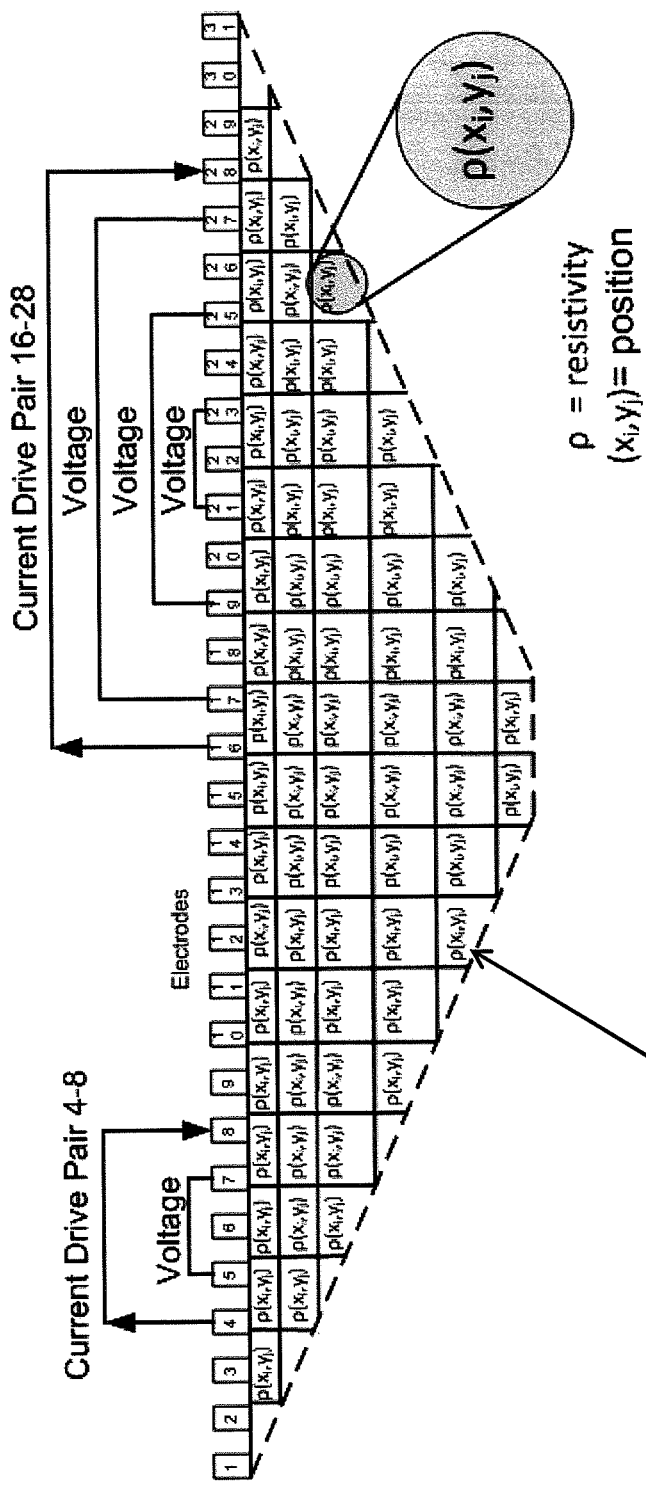
FIG. 13 schematically illustrates determining a spatial distribution of resistivities for subsurface regions beneath an array of electrodes ("imaging subsurface"). Knowing the resistivity of the subsurface allows the calculation of the voltages on the surface. An image may be produced by optimizing the resistivity in the subsurface to match the voltage measurements at the surface. The volume beneath the sensor may be divided up into various subsurface layers/volumes and represented by the mesh elements (grid) beneath the electrodes in the sensor.

FIG. 13 shows another example of the construction of a distribution of resistivities based on a multitude of electrical resistivity arrays. As mentioned above, when internal resistivities are known, it is possible to solve for the surface voltage; the inverse relationship may also be used (as here), to solve for internal resistivities given surface voltages. Thus, a heat map representing the distribution of the resistivities may be generated by optimizing to fit the sensed voltages given the drive current and the known geometry of the array 1309. In general, solving for the internal resistivities from surface voltages may be performed by solving a combination of forward and inverse problems. The relationship between sensed voltage, applied current and internal resistivities may be expressed as a Poisson equation. Although the geometry beneath the tissue surface is initially unknown, the measured voltage and known currents at different frequencies may be used to optimize within acceptable error tolerances to determine the resistivity of the sub-surfaces. This inverse problem may be iteratively solved and the results fed back into the forward problem to minimize the misfit error between the measured and computed resistivity values on the surface.

Figure 14:
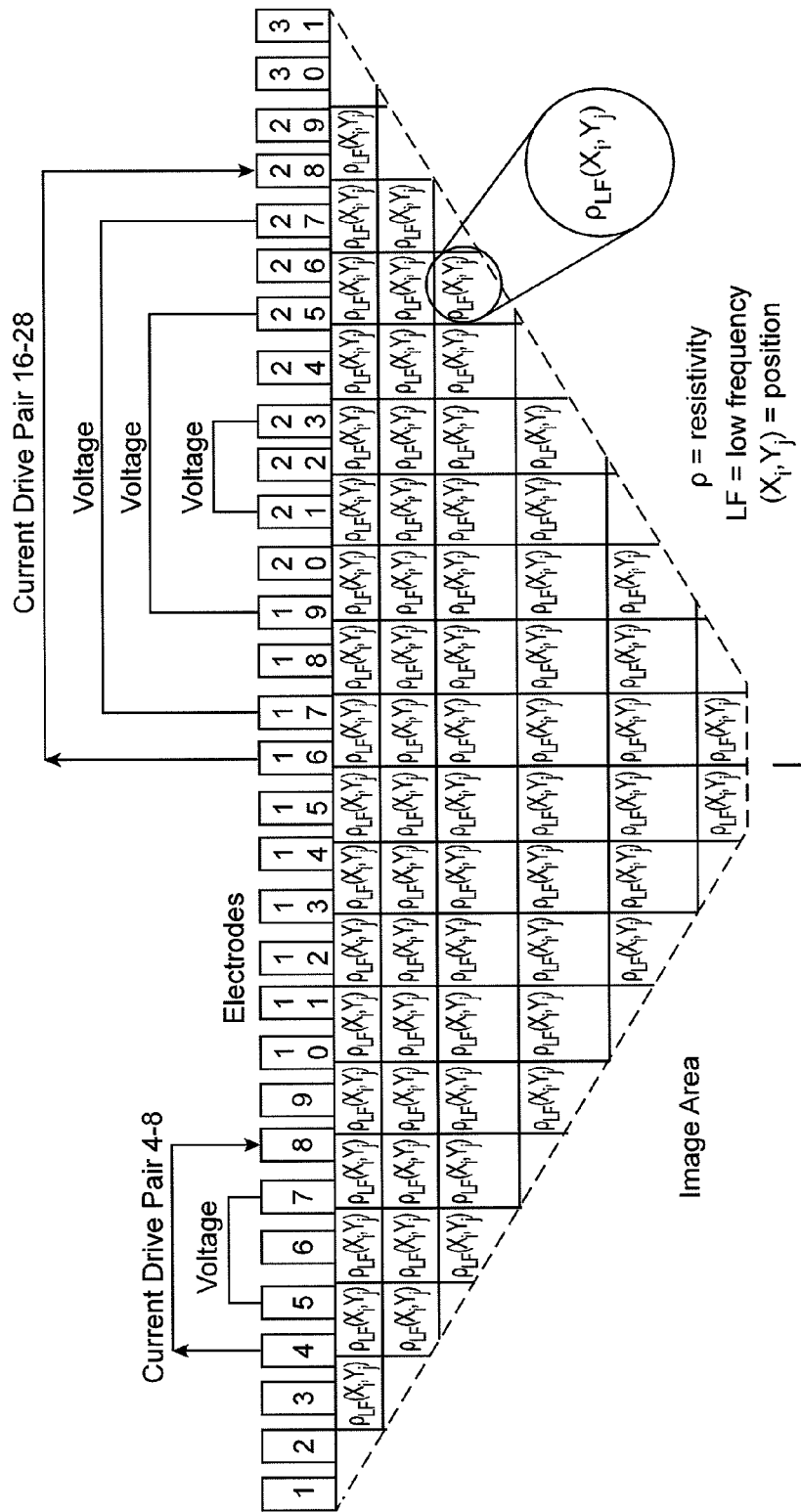
FIG. 14 illustrates one method of normalizing the resistivities determine as illustrated in FIG. 13 by determining a relative percent difference.

FIG. 14 illustrates one method of determining a distribution of relative percent differences in order to determine lung wetness. For example, in FIG. 14, the distribution of resistivities at a first (e.g., lowest) frequency is performed in step 1. In step 2, the distribution of resistivities at a second (e.g., highest) frequency is performed for the same volume. Finally, at step 3, the relative percent differences are calculated between the two frequencies (using the information of step 2 and step 3).

Figure 15:
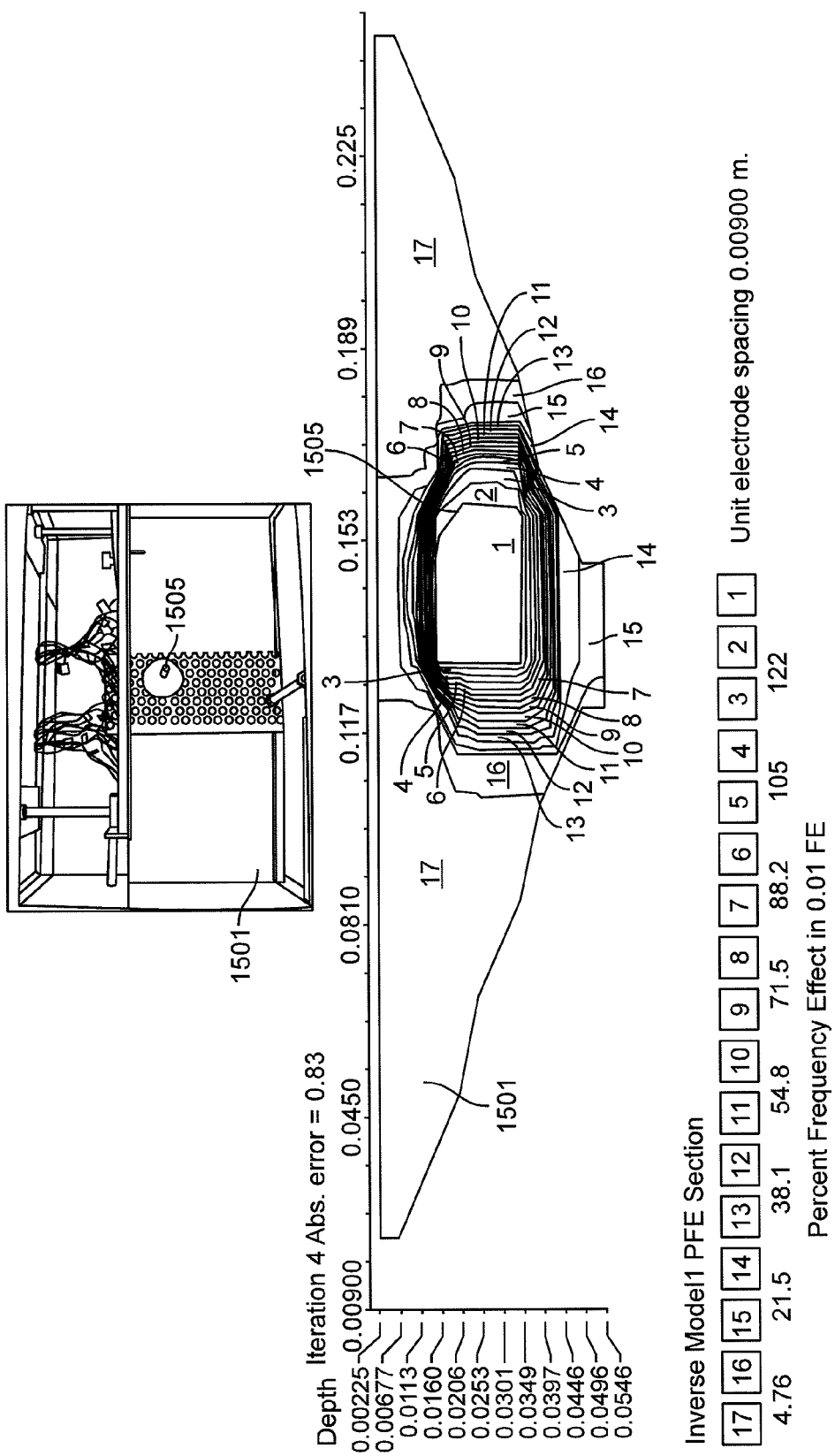
FIG. 15 is a schematic and resulting spatial distribution for an exemplary system determining the relative percent difference of a test biological material in a saline environment (biological inclusion in a saline tank). Saline has a low relative percent difference in resistivity between two frequencies 1501. An inclusion with cellular structure has a high relative percent difference in resistivity between two frequencies 1505.

An example of this method performed as a proof of principle is shown in FIG. 15. In this example, a saline tank 1501 holding a submerged biological tissue (yam 1505) is used with an array of electrodes near the top of the tank to confirm that the change in resistivity between the water and the biological tissue can be visualized. The distribution shown in the bottom of FIG. 15 illustrates the relative percent differences between a high (200 kHz) and low (20 kHz) kHz frequency for the yam in saline. The image is pseudo-colored, and shows that the boundary of the yam and water is readily distinguished, and as predicted, the biological tissue (yam) has a much larger relative percent difference than the water (which, as discussed above, is virtually flat).

Figure 16A:
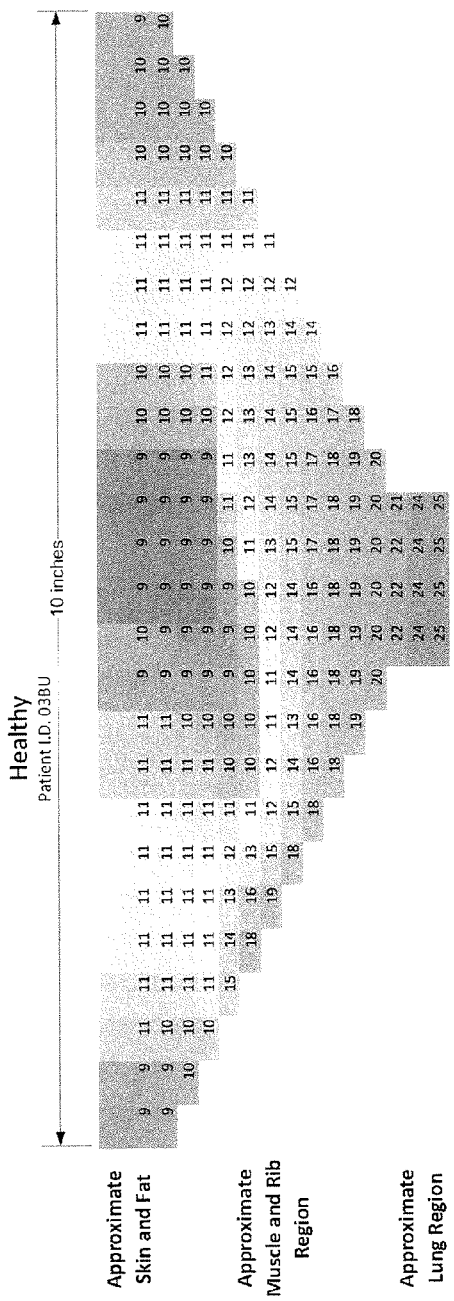
FIG. 16A shows one example of a spatial distribution of relative percent differences of resistivities between a low frequency (e.g., 20 kHz) and high frequency (e.g., 200 kHz) resistivity determination for a region of a healthy subject beneath a patch electrode array.
Figure 16B:
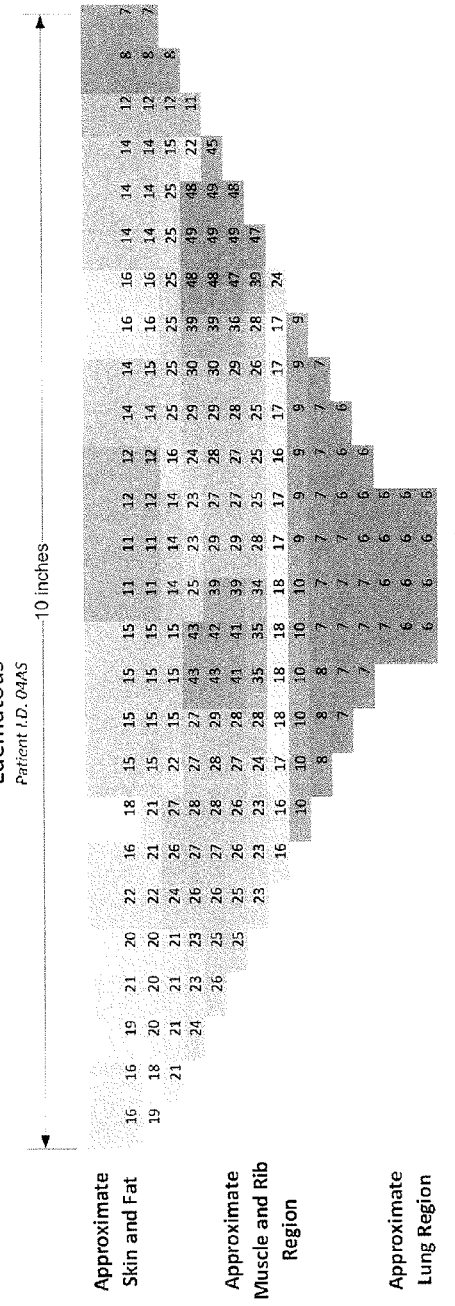
FIG. 16B shows an example of a spatial distribution of relative percent differences similar to that shown in FIG. 16A, only taken from an edematous subject.

FIGS. 16A and 16B illustrate one example of the application of the methods and systems described herein for detection of lung wetness. FIG. 16A shows a distribution of the relative percent differences of the resistivities between a high frequency and low frequency for a healthy ("dry" lung) subject. For comparison, FIG. 16B shows the distribution of relative percent differences of the resistivities between a high frequency and a low frequency for a wet (edematous) subject. The images may be analyzed to illustrate how to identify lung wetness.

A variety of tests may be used to interpret the distribution of resistivities, and particularly the distribution of relative percent differences of resistivities, to indicate or track lung wetness in a subject. For example, in some variations a series of tests or analyses of the distribution of relative percent differences may be performed in order to determine if a lung is wet or dry.

Figure 18A:
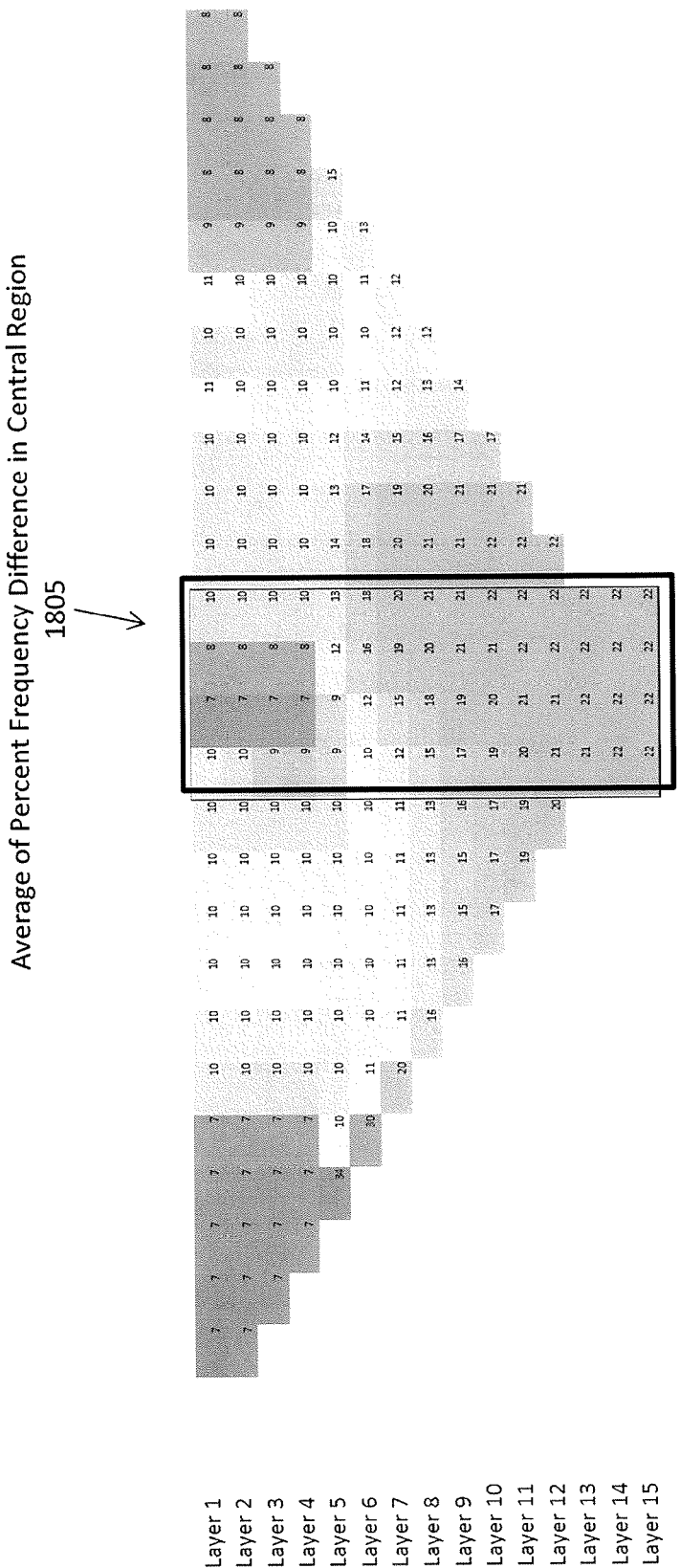
FIG. 18A illustrates another example of a spatial distribution of relative percent differences from a subject that does not have wet lung (showing a central region and gradient method of extracting information from the spatial distribution of relative subsurface resistivities).
Figure 18B:
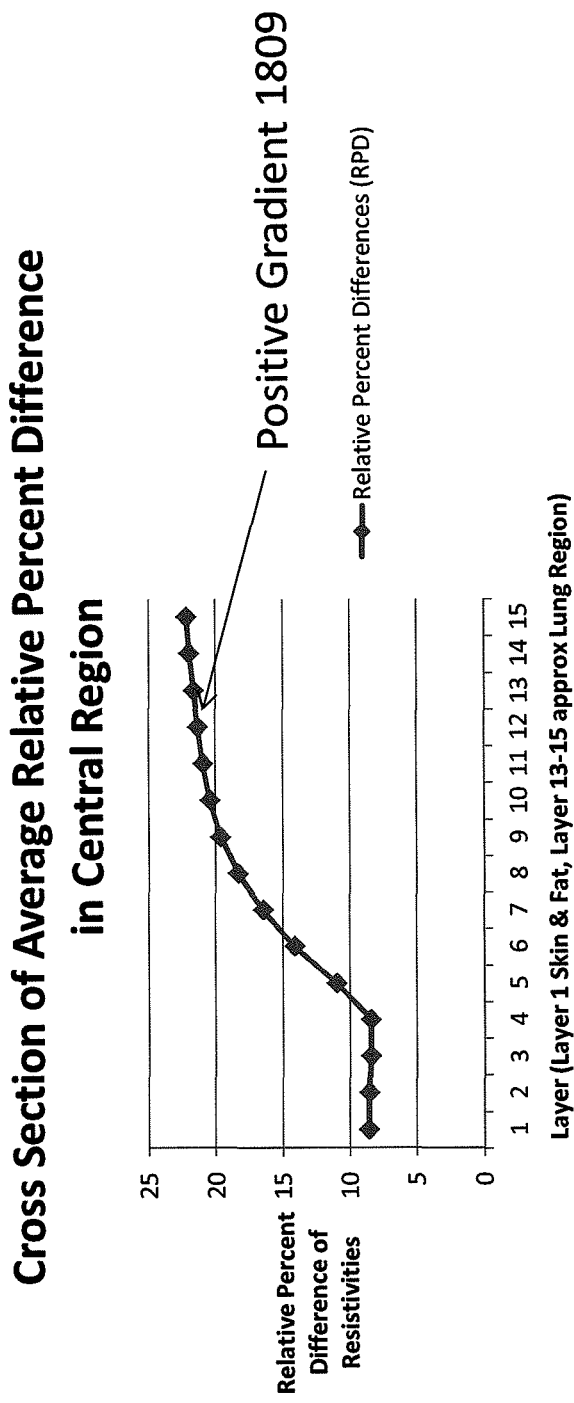
FIG. 18B illustrates on test for determining if the lung is wet or dry using the exemplary data shown in FIG. 18A.

For example, in one variation, the change in relative percent differences in the distribution with increasing depth into the tissue (e.g., from the outer skin surface, through the muscle and into the lung) may be examined to determine lung wetness. In this test of analysis, if the change in relative percent difference is increasing (e.g., if the slope of the lung wetness is positive) as the depth increases towards the lung, it is likely that the subject is dry (e.g., has a "dry" lung). This is illustrated in FIGS. 18A and 18B. In FIG. 18A, a central region of the distribution (shown by the central rectangle 1805 showing a 4×15 box) is examined. For each layer (roughly corresponding to depths of penetration into the tissue) an average value (the average of the four shown for that layer) of the relative percent differences is taken, and this average is plotted 1809 as shown in FIG. 18B. The resulting graph has a positive slope.

Figure 19:
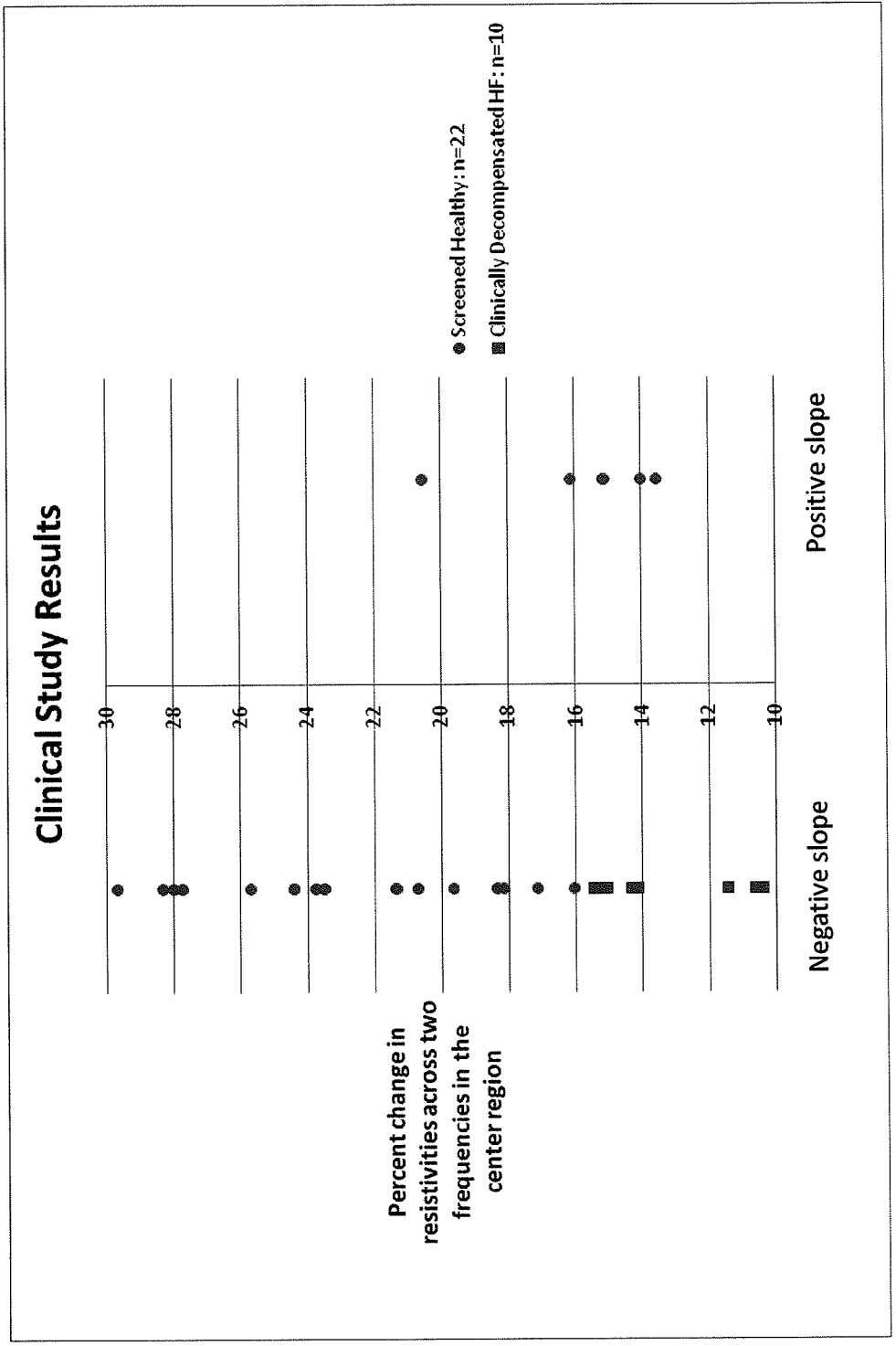
FIG. 19 illustrates 2 metrics that provide examples of methods for determining if a lung is wet or dry applied to screened healthy subjects (circles) with dry lungs, and edematous subjects (squares) having wet lungs, using an average of a central region of the spatial distribution of relative percent differences for each subject.

Another test that may be applied is shown in FIG. 19, in which an overall average value is extracted from the distribution of relative percent differences. In this example, an average of the central region (e.g., the boxed region shown in FIG. 18A) is taken and compared to a threshold value. If the average is above the threshold value, it is likely that the lung is dry; if the value is below the threshold value, the lung may be wet (although additional tests may be applied). In FIG. 19, average percent changes in resistivities between a high and low frequency taken from the central region of the distribution were plotted for both healthy (dry) subjects and edematous (wet) subjects. In the example shown in FIG. 19, the wet subjects all fell below a threshold of under 16, whereas all of the healthy (dry) subjects that had non-positive (e.g., negative, flat) slopes (for the change in relative percent difference from the central region) fell above this threshold. It should be appreciated that the threshold shown here is merely exemplary. The appropriate threshold value may vary depending on various factors, such as the manner in which the average value is determined, the configuration of the array, the high and low frequencies used to generate the RPD, and the like, the general principle of a threshold value remains. The actual numeric value of the threshold may therefore be empirically determined using similar parameters across a variety of dry and wet subjects. In some variations, the threshold value is not a strict cut-off, but may include a range of values; if the average (or in some variations the sum) value of the RPD is within this range; the lung may be wet or may be indeterminate.

Figure 17A:
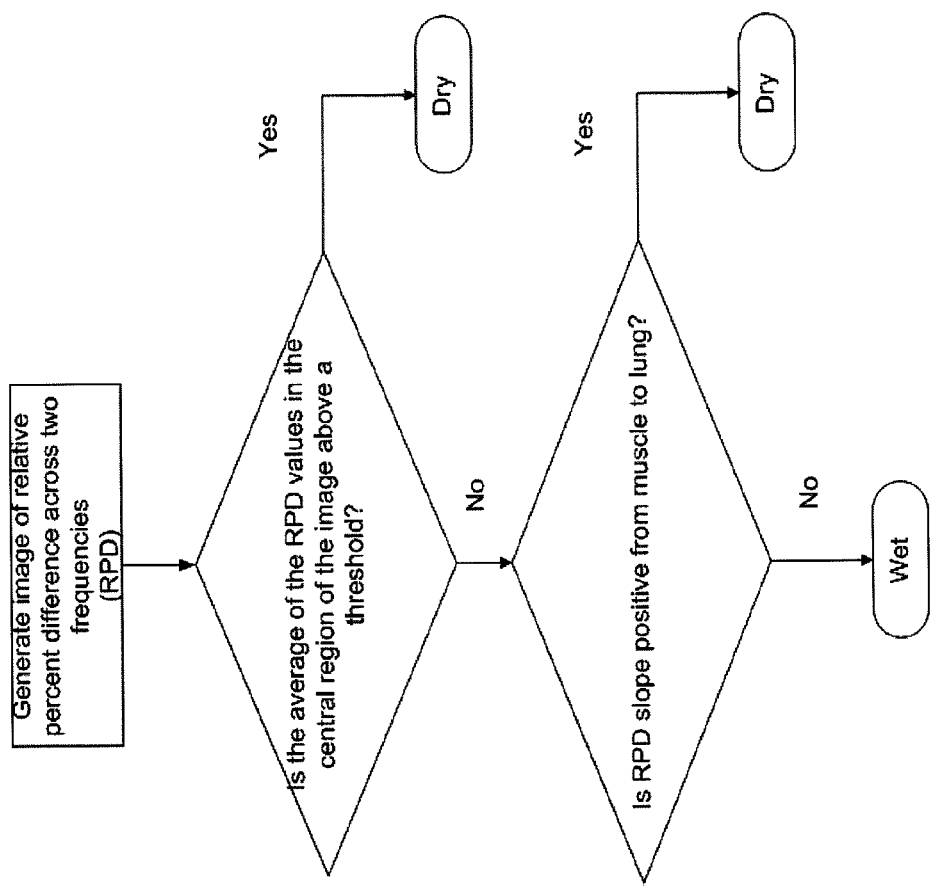
FIGS. 17A and 17B illustrate various methods of determining if a lung is wet or dry using a spatial distribution of relative percent differences (a subset of the relative spatial change in subsurface resistivities across frequencies) such as those shown in FIGS. 16A and 16B.
Figure 17B:
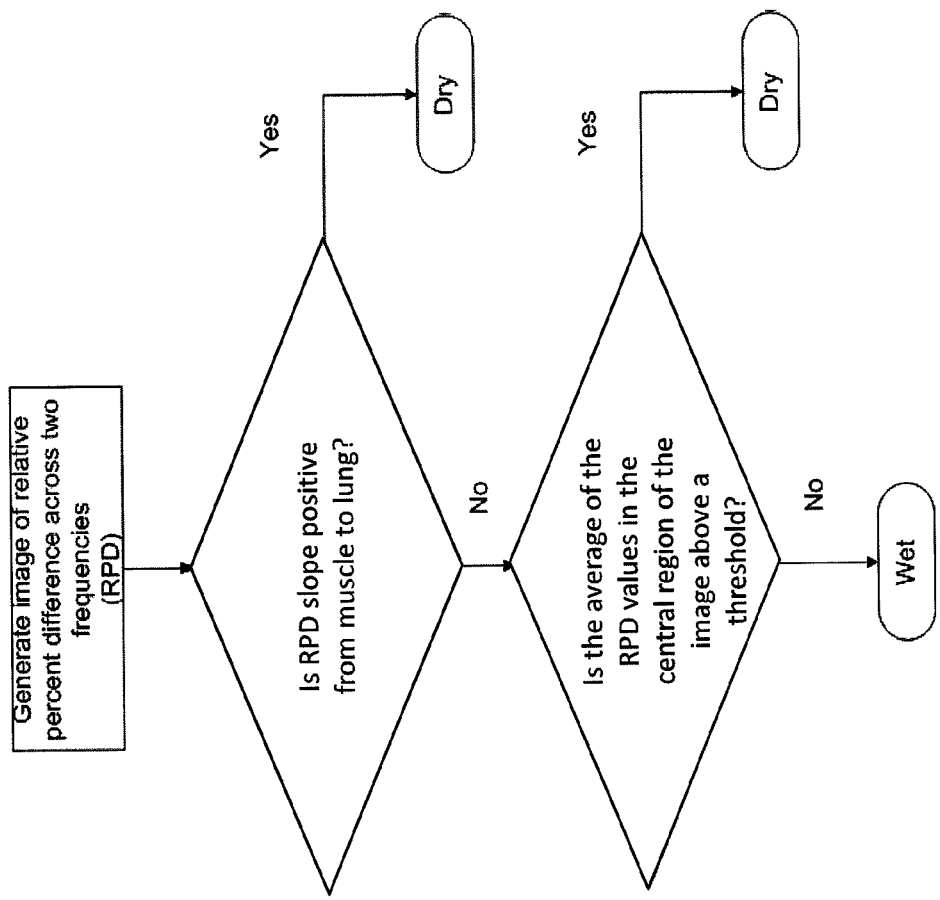

As mentioned above, a combination of different tests may be used to determine lung wetness. For example, in some variations an individual test alone is not conclusive, but different tests may be performed sequentially or in parallel to provide a higher degree of confidence of lung wetness. For example, FIGS. 17A and 17B illustrate variation of methods for testing to determine lung wetness using the individual tests described above. For example, in FIG. 17A, a distribution of relative percent differences between high and low frequencies may be serially examined to determine lung wetness. In this example, the first test performed is the comparison of the average RPD from the center of the distribution (including the "deepest" region). If the average RPD value is above the threshold (e.g., >about 16), then the subject's lung is considered "dry;" if the average RPD value is below the threshold (e.g., <about 16), then the second test (looking at the slope as illustrated in FIGS. 18A and 18B) is performed. The order of these tests may be switched in some variations, as shown in FIG. 17B.

Figure 20:
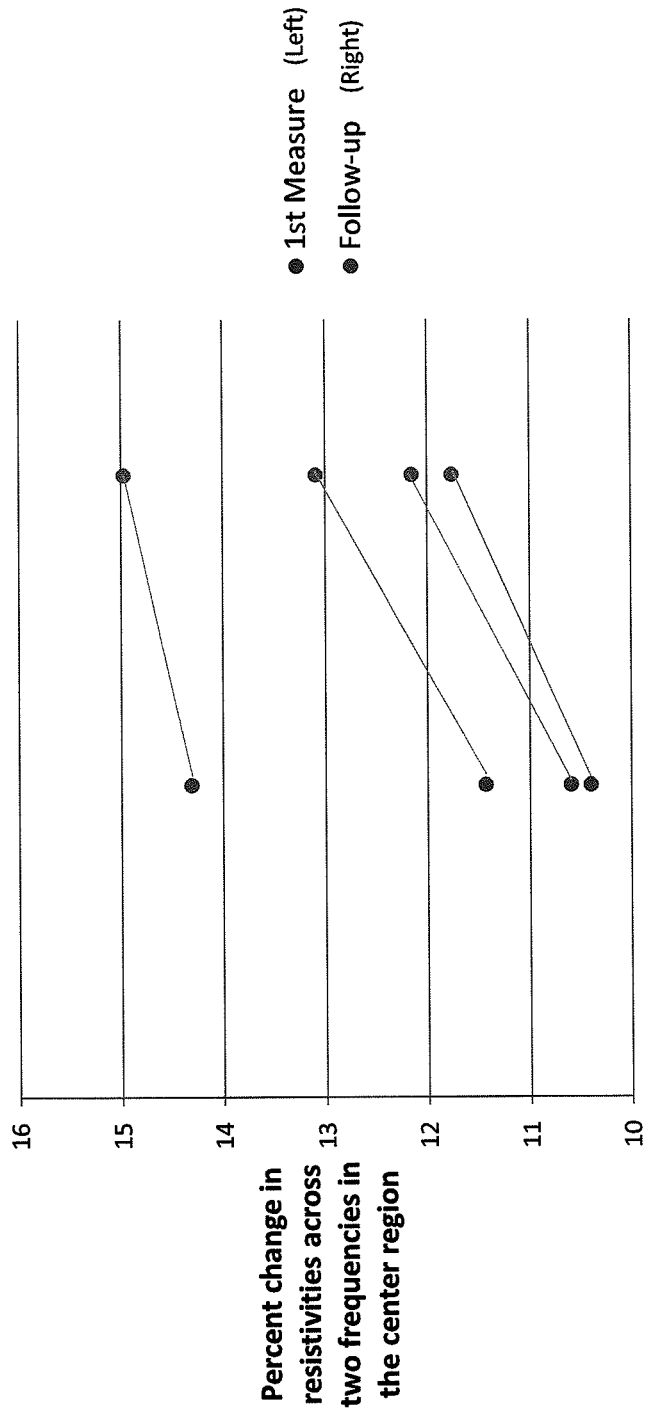
FIG. 20 shows a measure of clinical progression for four subjects monitored as described herein using an average of a central region of the spatial distribution of relative percent differences for each subject.

Any of the methods and systems described herein may also be used to examine the clinical progression of lung wetness, including monitoring of treatments for lung wetness (e.g., diuretic treatments, etc.). An example of this is illustrated in FIG. 20. In this example, four subjects having lung wetness were monitored over treatment. Lung wetness by assessed by the techniques described herein (including the generation of a distribution of RPD), and was configured by classical diagnostic methods, including listening (auscultation) for rales or characteristic "crackling" sound linked to excessive fluid in the airways. All four subjects initially had average RPD's from the central region of the distribution that were below the threshold, indicating lung wetness. During the course of treatment, as shown in the "follow up" column on the right side of FIG. 20, this average value increased in all subjects, however, all of these subjects remained below the threshold. Interestingly, these subjects also showed an improvement in their lung wetness and in some cases no longer displayed some of the more classical characteristics of lung wetness such as rales during respiration. Although these subjects showed some improvements, other measures of overall lung wetness (such as swollen ankles, etc.) remained. This may indicate the relative sensitivity of the present systems and methods, particularly in tracking the treatment of lung wetness, compared to more traditional methods.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

It should be understood that features and sub-combinations of the inventions described herein may have utility alone or in combinations not explicitly described herein. Further the inventions described herein may be employed without reference to other features and subcombinations. Many possible embodiments may be made without departing from the scope, and it is to be understood that all of the subject matter herein set forth or shown in the accompanying drawings is to be interpreted as illustrative, and not limiting.

What is claimed is:

1. A method of non-invasively determining lung wetness, the method comprising:
   placing a sensor comprising a plurality of electrodes arranged in a proximal to distal active region on the subject's back so that the proximal to distal axis of the sensor extends cranially to caudally along the subject's back, and wherein the active region of the sensor is positioned lateral to the subject's spine;
   using the sensor to determine a relative spatial change in subsurface resistivities across frequencies (RSCSRAF) based on applied currents and detected voltages, wherein determining the RSCSRAF comprises normalizing a resistivity at a first frequency within a first subsurface region by a resistivity at a second frequency within the first subsurface region; and
   indicating if the lung is wet based on the relative spatial change in subsurface resistivities across frequencies, wherein the relative spatial change in subsurface resistivities across frequencies is determined using an inverse problem to solve for the spatial distribution of subsurface resistivities by minimizing the error between detected values and those produced by a forward model calculating a change in subsurface resistivities.

2. The method of claim 1, wherein placing the sensor comprises positioning the active region of the sensor offset from the midline of the subject's back lateral to the spine.

3. The method of claim 1, wherein the sensor comprises a plurality of elongate electrodes arranged in parallel and oriented transverse to the proximal to distal axis of the sensor to form the active region.

4. The method of claim 1, wherein placing comprises placing the proximal portion of the active region of the sensor in line with the top of the subject's scapula.

5. The method of claim 1, wherein placing comprises placing a middle portion of the sensor in line with the subject's lung.

6. The method of claim 1, further comprising applying a plurality of currents between pairs of at least some of the electrodes, wherein current is applied to pairs of electrodes while detecting voltage with other pairs of electrodes, further wherein a plurality of current frequencies are applied.

7. The method of claim 1, wherein using the sensor to determine a relative spatial change in subsurface resistivities across frequencies comprises determining a spatial distribution of relative percent differences of apparent resistivities at a low frequency of 20 kHz or lower and a higher second frequency.

8. The method of claim 1, further comprising presenting a representation of lung wetness based on the relative spatial change in subsurface resistivities across frequencies.

9. The method of claim 1, wherein placing the sensor comprises placing the active region of the sensor offset from the midline of the subject's back lateral to the subject's spine by an inch +/−10% of an inch.

10. The method of claim 1, wherein placing the sensor comprises placing the active region of the sensor along the subject's back from a region in line with the top of the subject's scapula and extending caudally for 8 or more inches.

11. The method of claim 1, wherein placing the sensor comprises placing the center of the active region of the sensor along the subject's back from a region in line with the subject's lung.

12. The method of claim 1, wherein placing the sensor comprises positioning a lateral edge of the active region of the sensor offset by an inch +/−10% of an inch from the midline of the subject's back.

13. The method of claim 1, wherein placing the sensor comprises placing the sensor so that the active region of the sensor extends laterally from an inch +/−10% of an inch from the midline of the subject's back to 3 inches +/−10% of 3 inches from the midline of the subject's back.

14. The method of claim 1, wherein each electrode of the active region extends laterally from an inch +/−10% of an inch from the midline of the subject's back to 3 inches +/−10% of 3 inches from the midline of the subject's back.

15. The method of claim 1, further comprising conforming the sensor the subject's skin as it extends along the length of the back.

16. A method of non-invasively determining lung wetness, the method comprising:

applying currents at a plurality of frequencies from a sensor on a region of a subject's back;

determining a spatial distribution of relative spatial change in subsurface resistivities (RSCSRAF) across frequencies across the region of the subject's back, wherein the RSCSRAF is determined at last in part by normalizing a resistivity at a first frequency within a first subsurface region by a resistivity at a second frequency within the first subsurface region; and comparing an average of at least some of the values from the relative spatial change in subsurface resistivities across frequencies to a threshold value, and indicating if the lung is dry or wet based on this comparison, wherein the relative spatial change in subsurface resistivities across frequencies is determined using an inverse problem to solve for the spatial distribution of subsurface resistivities by minimizing the error between detected values and those produced by a forward model calculating a change in subsurface resistivities.

17. The method of claim 16, wherein comparing an average comprises comparing an average of values from the relative spatial change in subsurface resistivities across frequencies from a central subsurface region beneath the sensor to the threshold value.

18. The method of claim 16, wherein comparing comprises indicating if the lung is dry or wet based on the comparison and based on a depth of a peak relative spatial change in subsurface resistivities across frequencies value.

19. The method of claim 1, wherein indicating if the lung is wet comprises indicating without producing an image.

* * * * *